US012509438B2

(12) United States Patent
Lee et al.

(10) Patent No.: US 12,509,438 B2
(45) Date of Patent: Dec. 30, 2025

(54) PYRAZOLE DERIVATIVE

(71) Applicant: Aptabio Therapeutics Inc., Yongin-si (KR)

(72) Inventors: Soo Jin Lee, Suwon-si (KR); Sung Hwan Moon, Suwon-si (KR); Soo Ho Ban, Suwon-si (KR); Eun Sil Lee, Suwon-si (KR); Eun Jung Shin, Suwon-si (KR); Yoo-Kyung Goh, Suwon-si (KR); Sung Chan Lee, Suwon-si (KR); Hyun Kyung Yu, Suwon-si (KR)

(73) Assignee: APTABIO THERAPEUTICS INC., Yongin-si (KR)

( * ) Notice: Subject to any disclaimer, the term of this patent is extended or adjusted under 35 U.S.C. 154(b) by 737 days.

(21) Appl. No.: 17/791,983

(22) PCT Filed: Jan. 12, 2021

(86) PCT No.: PCT/KR2021/000425
§ 371 (c)(1),
(2) Date: Jul. 11, 2022

(87) PCT Pub. No.: WO2021/145655
PCT Pub. Date: Jul. 22, 2021

(65) Prior Publication Data

US 2023/0067461 A1 Mar. 2, 2023

(30) Foreign Application Priority Data

Jan. 13, 2020 (KR) ........................ 10-2020-0004471

(51) Int. Cl.

| | |
|---|---|
| ***C07D 471/04*** | (2006.01) |
| ***A61K 31/437*** | (2006.01) |
| ***C07D 401/04*** | (2006.01) |
| ***C07D 519/00*** | (2006.01) |

(52) U.S. Cl.
CPC ......... *C07D 401/04* (2013.01); *C07D 471/04* (2013.01); *C07D 519/00* (2013.01)

(58) Field of Classification Search
CPC ..... C07D 471/04; A61K 31/437; A61P 25/16; A61P 29/00; A61P 11/00; A61P 35/00
USPC .......................................... 546/119; 514/303
See application file for complete search history.

(56) References Cited

U.S. PATENT DOCUMENTS

| | | | |
|---|---|---|---|
| 6,239,076 | B1 | 5/2001 | Ryu et al. |
| 8,748,456 | B2 | 6/2014 | Page et al. |
| 2008/0234327 | A1 | 9/2008 | Cadieux et al. |
| 2012/0196880 | A1 | 8/2012 | Anderson et al. |
| 2014/0275015 | A1 | 9/2014 | Alcazar Vaca et al. |

FOREIGN PATENT DOCUMENTS

| | | |
|---|---|---|
| CN | 102762562 | 10/2012 |
| CN | 103492375 | 1/2014 |
| DE | 2701467 | 7/1977 |
| DE | 3832348 | 9/1989 |
| DE | 3917469 | 12/1990 |
| DE | 4023488 | 1/1992 |
| GB | 1539846 | 2/1979 |
| IN | 288865 | 7/2007 |
| JP | 2010-511698 | 4/2010 |
| JP | 2012-502023 | 1/2012 |
| JP | 2013-520407 | 6/2013 |
| KR | 10-2006-0054291 | 5/2006 |
| KR | 10-2014-0015156 | 2/2014 |
| RU | 2659220 | 6/2018 |
| WO | 1993-007138 | 4/1993 |
| WO | 2005-040169 | 5/2005 |
| WO | 2008-118790 | 10/2008 |
| WO | 2010-015657 | 2/2010 |
| WO | 2011-101804 | 8/2011 |
| WO | 2015-144801 | 10/2015 |
| WO | 2015-164520 | 10/2015 |
| WO | 2016-207785 | 12/2016 |
| WO | 2019-079596 | 4/2019 |
| WO | 2019-079607 | 4/2019 |
| WO | 2019-141957 | 7/2019 |

OTHER PUBLICATIONS

Amira A.M Adly, "Oxidative stress and disease: an updated review." Research Journal of Immunology 3.2 (Oct. 8, 2010): 129-45.
GD Calderon et al. "Oxidative stress and diabetic retinopathy: development and treatment." Eye 31.8 (Apr. 28, 2017): 1122-1130.
Day, Christopher P., et al. "Steatohepatitis: a tale of two "hits"?" Gastroenterology 114, No. 4 (Apr. 1998): 842-845.
Toren Finkel, "Signal transduction by reactive oxygen species." Journal of Cell Biology 194.1 (Jul. 11, 2011): 7-15.
Francesco Galli et al. "Oxidative stress and reactive oxygen species." Cardiovascular disorders in Hemodialysis 149 (May 3, 2005): 240-260.
Geon Ha Kim et al. "The role of oxidative stress in neurodegenerative diseases." Experimental neurobiology 24.4 (Oct. 12, 2015): 325.
Geou-Yarh Liou et al. "Reactive oxygen species in cancer." Free radical research 44.5 (May 2010): 479-496.
Shyamal K. Goswami et al., "Ischemia-reperfusion and cardioprotection: a delicate balance between reactive oxygen species generation and redox homeostasis." Annals of medicine 39.4 (2007): 275-289.
Axel M. Gressner et al., "Roles of TGF-beta in hepatic fibrosis." Frontiers in Bioscience-Landmark 7.4 (Apr. 1, 2002): 793-807.
Kira M. Holmström et al., "Cellular mechanisms and physiological consequences of redox-dependent signalling." Nature reviews Molecular cell biology 15.6 (Jun. 2014): 411-421.
Joy X. Jiang et al. "Reduced nicotinamide adenine dinucleotide phosphate oxidase 2 plays a key role in stellate cell activation and liver fibrogenesis in Vivo." Gastroenterology 139.4 (Oct. 2010): 1375-1384.

(Continued)

*Primary Examiner* — Charanjit Aulakh
(74) *Attorney, Agent, or Firm* — LEX IP MEISTER, PLLC

(57) ABSTRACT

The present invention provides a novel pyrazole derivative compound represented by Chemical formula I or a salt thereof, and a pharmaceutical composition comprising the same.

10 Claims, 6 Drawing Sheets

(56) References Cited

OTHER PUBLICATIONS

N. Kashihara et al. "Oxidative stress in diabetic nephropathy." Current medicinal chemistry 17.34 (Dec. 1, 2010): 4256-4269.
Keijiro Ishikawa et al. "Molecular mechanisms of subretinal fibrosis in age-related macular degeneration." Experimental eye research 142 (Jan. 2016): 19-25.
Yong-Han Paik et al. "The nicotinamide adenine dinucleotide phosphate oxidase (NOX) homologues NOX1 and NOX2/gp91phox mediate hepatic fibrosis in mice." Hepatology 53.5 (May 2011): 1730-1741.
RN 1597450-14-0 Registry, ED Entered STN: May 5, 2014, CN 2H-Pyrazolo [4,3-c] pyridin-3-ol, 4,5,6,7-tetrahydro-5-methyl-2-phenyl-, hydrochloride (2:1) (CA Index Name).
Matloob Ahmad et al., "Anti-oxidant and anti-bacterial activities of novel N'-arylmethylidene-2-(3, 4-dimethyl-5, 5-dioxidopyrazolo [4, 3-c][1, 2] benzothiazin-2 (4H)-yl) acetohydrazides" European Journal of Medicinal Chemistry, 2010, v.45, No. 2, pp. 698-704, (Nov. 11, 2009).
Rospatent, Office Action & Search Report of the corresponding RU Patent Application No. 2022120028 dated Mar. 14, 2023.
KIPO, PCT Search Report & Written Opinion of PCT/KR2021/000425 dated Apr. 16, 2021.
Mengjia Song et al., "Future of anti-PD-1/PD-L1 applications: Combinations with other therapeutic regimens", Chinese Journal of Cancer Research, 2018, 30(2):157-172. https://doi.org/10.21147/j.issn.1000-9604.2018.02.01.
Tian Lan et al., "Deficiency of NOX1 or NOX4 Prevents Liver Inflammation and Fibrosis in Mice through Inhibition of Hepatic Stellate Cell Activation", PLoS One 2015;10:e0129743, Jul. 29, 2015. doi:10.1371/journal.pone.0129743.
Merry W. Ma et al., "NADPH oxidase in brain injury and neurodegenerative disorders", Molecular neurodegeneration, 12:7, 2017. DOI 10.1186/s13024-017-0150-7.
Alessandro G. Fois et al., "Evaluation of oxidative stress biomarkers in idiopathic pulmonary fibrosis and therapeutic applications: a systematic review", Respiratory Research (2018) 19:51. https://doi.org/10.1186/s12931-018-0754-7.
Rohan Samarakoon et al., "TGF-β Signaling in Tissue Fibrosis: Redox Controls, Target Genes and Therapeutic Opportunities", Cell Signal. Jan. 2013 ; 25(1): 264-268. doi:10.1016/j.cellsig.2012.10.003.
Mao, Zewei et al., "Synthesis and Biological Evaluation of Piperazine Substituted 3-Aryl-5-furanyldihydropyrazole Amide Derivatives", Chin. J. Org. Chem. 2018, 38, 2167~2173, DOI: 10.6023/cjoc201802010.
EPO, Search Report of EP 21740932.5 dated Aug. 1, 2024.
B. I. Buzykin et al., "Tautomerism of Aza Cycles: IV.1 Tautomeric Structure of 4,5-Dihydropyrazol-5-one Annelated on Bond C3—C4 with Piperidine Cycle, and Its Three Hydrochlorides", Russian Journal of General Chemistry, 2014, vol. 84, No. 3, Mar. 2014, pp. 531-544.
K. Hohenlohe-Oehringen et al., "Über zwei Δ-isomere N-Methyl-5-phenyl-piperidein-carbonsäureester-(3)", Monatshefte für Chemie 92, 313-321 (1961), Mar. 1, 1961. https://doi.org/10.1007/BF01153887.
SIC, Office Action of CO NC2022/0010431 dated May 5, 2025, total 9 pages.
EPO, supplementary partial European search report of EP 21740932.5 dated Feb. 27, 2024.
Soad A. M. El-Hawash et al., "Synthesis of some new quinoxalines and 1,2,4-triazolo[4,3-a]-quinoxalines for evaluation of in vitro antitumor and antimicrobial activities", Arch. Pharm. Chem. Life Sci. 2006, 339, 564-571, doi: 10.1002/ardp.200600061.
Matthieu Desroses et al., "A Convenient Microwave-Assisted Propylphosphonic Anhydride (T3P®) Mediated One-Pot Pyrazolone Synthesis", Eur. J. Org. Chem. 2013 (26) 5879-5885, Jul. 29, 2013.
Zhong Li et al., "2-Phenyl-5,6-dihydro-2H-thieno[3,2-c]pyrazol-3-ol Derivatives as New Inhibitors of Bacterial Cell Wall Biosynthesis", Bioorganic & Medicinal Chemistry Letters 13 (2003) 2591-2594.
Javier De Mendoza et al., "N,N'-linked biazoles. Part 7. Oxidative dimerization of N-unsubstituted tetrahydroindazolones", Tetrahedron, vol. 42, No. 8, Jan. 1986 (Jan. 1986), pp. 2377-2386, XP093132053.
John W. Lyga et al., "Synthesis, mechanism of action, and QSAR of herbicidal 3-substituted-2-aryl-4,5,6,7-tetrahydroind azoles", Pesticide Science., vol. 42, No. 1, Sep. 1994 (Sep. 1994), pp. 29-36, XP93132O52.
Indian Patent Office, the hearing notice report of IN 202247040341 dated Mar. 15, 2024.
V.G. Belikov, "Pharmaceutical Chemistry". Chapter 2.2 "The relationship between the structure of the molecules of substances and their effect on the body".—M.: Higher School, 1993, pp. 43-47.
Belikov V.G. Pharmaceutical Chemistry. Manual. Fourth edition, Moscow, "MEDpress-inform". 2007, pp. 27-29.
Dyson G., May P., "Chemistry of synthetic drugs", Moscow, 1964, pp. 12-19.
Rospatent, Office Action of RU 2022120028 dated Jan. 22, 2023.
Stephen Robert Fletcher et al., "The search for novel TRPV1-antagonists: from carboxamides to benzimidazoles and indazolones", Bioorganic & Medicinal Chemistry Letters, Jun. 1, 2006;16(11):2872-6. doi: 10.1016/j.bmcl.2006.03.004.
RN 2111557-89-0 Registry, Database Registry [Online] Retrieved from STN, Aug. 10, 2017, search date : Jul. 13, 2023 10.
RN 2110880-19-6 Registry, Database Registry [Online] Retrieved from STN, Aug. 9, 2017, search date : Jul. 13, 2023.
RN 2109736-97-0 Registry, Database Registry [Online] Retrieved from STN, Aug. 7, 2017, search date: Jul. 13, 2023.
RN 2109617-04-9 Registry, Database Registry [Online] Retrieved from STN, Aug. 7, 2017, search date: Jul. 13, 2023.
RN 2107711-43-1 Registry, Database Registry [Online] Retrieved from STN, Aug. 3, 2017, search date: Jul. 13, 2023.
RN 2107204-84-0 Registry, Database Registry [Online] Retrieved from STN, Aug. 2, 2017, search date: Jul. 13, 2023.
RN 2107018-03-9 Registry, Database Registry [Online] Retrieved from STN, Aug. 2, 2017, search date: Jul. 13, 2023.
RN 2106128-62-3 Registry, Database Registry [Online] Retrieved from STN, Aug. 1, 2017, search date: Jul. 13, 2023.
RN 2105268-91-3 Registry, Database Registry [Online] Retrieved from STN, Jul. 30, 2017, search date: Jul. 13, 2023.
RN 2105099-01-0 Registry, Database Registry [Online] Retrieved from STN, Jul. 30, 2017, search date: Jul. 13, 2023.
RN 2105095-58-5 Registry, Database Registry [Online] Retrieved from STN, Jul. 30, 2017, search date: Jul. 13, 2023.
RN 2104405-84-5 Registry, Database Registry [Online] Retrieved from STN, Jul. 28, 2017, search date: Jul. 13, 2023.
RN 1822923-13-6 Registry, Database Registry [Online] Retrieved from STN, Dec. 4, 2015, search date: Jul. 13, 2023.
RN 1822725-26-7 Registry, Database Registry [Online] Retrieved from STN, Dec. 5, 2015, search date: Jul. 13, 2023.
RN 1785580-39-3 Registry, Database Registry [Online] Retrieved from STN, Jun. 21, 2015, search date: Jul. 13, 2023.
RN 1785459-65-5 Registry, Database Registry [Online] Retrieved from STN, Jun. 21, 2015, search date: Jul. 13, 2023.
RN 1785186-32-4 Registry, Database Registry [Online] Retrieved from STN, Jun. 21, 2015, search date: Jul. 13, 2023.
RN 1784334-83-3 Registry, Database Registry [Online] Retrieved from STN, Jun. 19, 2015, search date: Jul. 13, 2023.
RN 1783974-85-5 Registry, Database Registry [Online] Retrieved from STN, Jun. 19, 2015, search date: Jul. 13, 2023.
RN 1783974-70-8 Registry, Database Registry [Online] Retrieved from STN, Jun. 19, 2015, search date: Jul. 13, 2023.
RN 1782604-87-8 Registry, Database Registry [Online] Retrieved from STN, Jun. 17, 2015, search date: Jul. 13, 2023.
RN 1781899-06-6 Registry, Database Registry [Online] Retrieved from STN, Jun. 17, 2015, search date: Jul. 13, 2023.
RN 1781791-13-6 Registry, Database Registry [Online] Retrieved from STN, Jun. 17, 2015, search date: Jul. 13, 2023.

(56) References Cited

OTHER PUBLICATIONS

RN 1781423-63-9 Registry, Database Registry [Online] Retrieved from STN, Jun. 17, 2015, search date: Jul. 13, 2023.
RN 1781385-25-8 Registry, Database Registry [Online] Retrieved from STN, Jun. 17, 2015, search date: Jul. 13, 2023.
RN 1781375-15-2 Registry, Database Registry [Online] Retrieved from STN, Jun. 17, 2015, search date: Jul. 13, 2023.
RN 1781076-85-4 Registry, Database Registry [Online] Retrieved from STN, Jun. 15, 2015, search date: Jul. 13, 2023.
RN 1780386-14-2 Registry, Database Registry [Online] Retrieved from STN, Jun. 14, 2015, search date: Jul. 13, 2023.
RN 1780385-90-1 Registry, Database Registry [Online] Retrieved from STN, Jun. 14, 2015, search date: Jul. 13, 2023.
RN 1780040-70-1 Registry, Database Registry [Online] Retrieved from STN, Jun. 14, 2015, search date: Jul. 13, 2023.
RN 1774900-23-0 Registry, Database Registry [Online] Retrieved from STN, Jun. 7, 2015, search date: Jul. 13, 2023.
RN 1215484-85-7 Registry, Database Registry [Online] Retrieved from STN, Apr. 1, 2010, search date: Jul. 13, 2023.
JPO, Office Action of JP 2022-543171 dated Aug. 29, 2023.
SIPO, Office Action of CN 202160009272.6 dated Jun. 10, 2025, total 16 pages.

【FIG. 1】
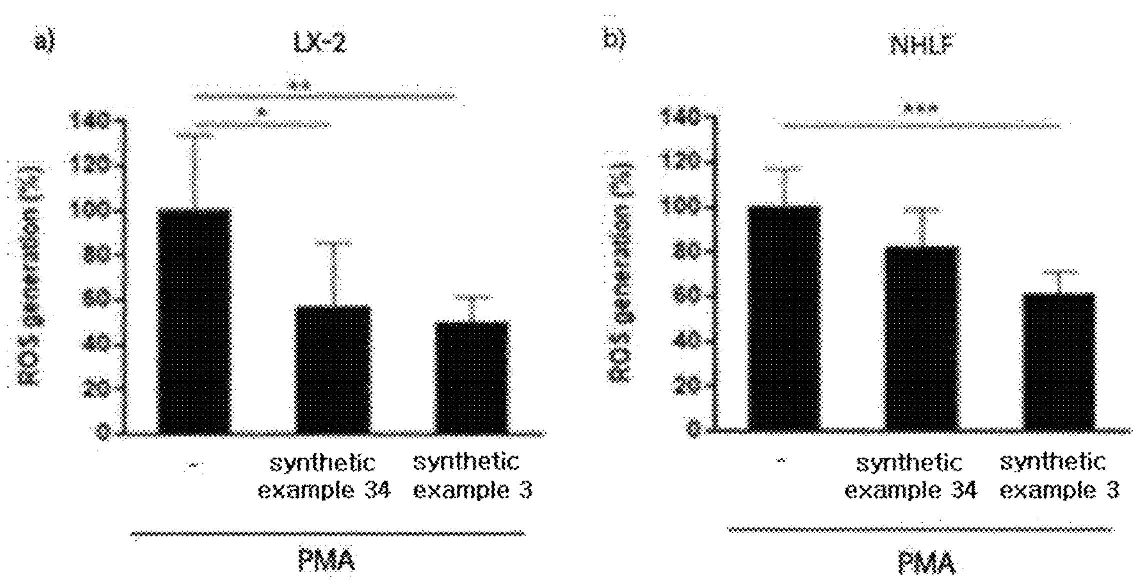

【FIG. 2】
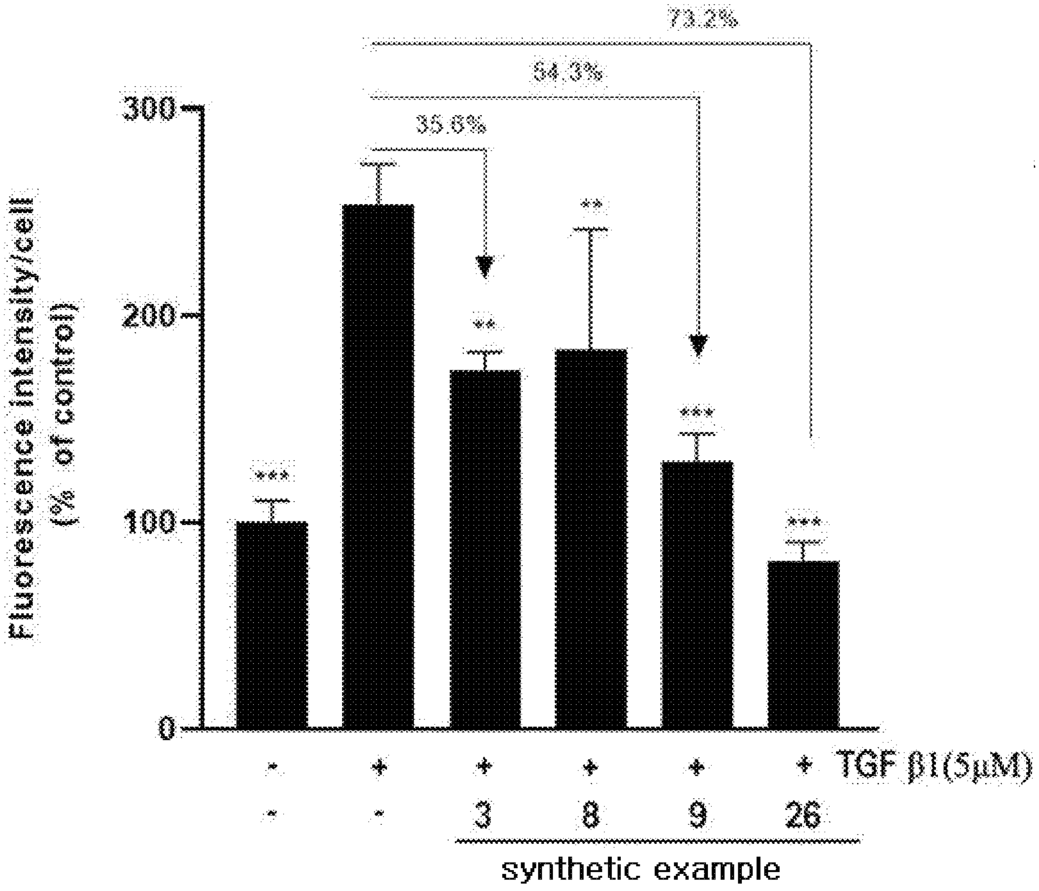

【FIG. 3】
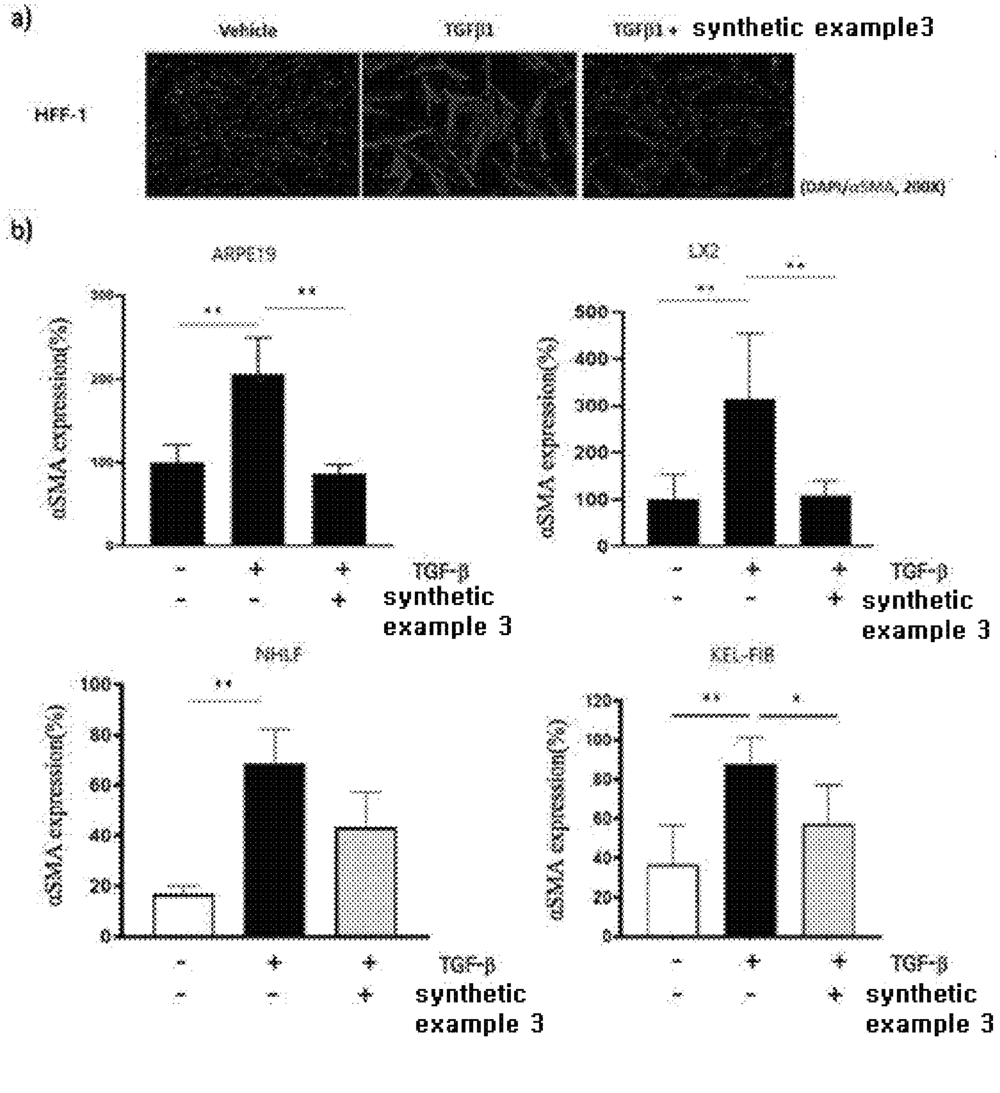

【FIG. 4】
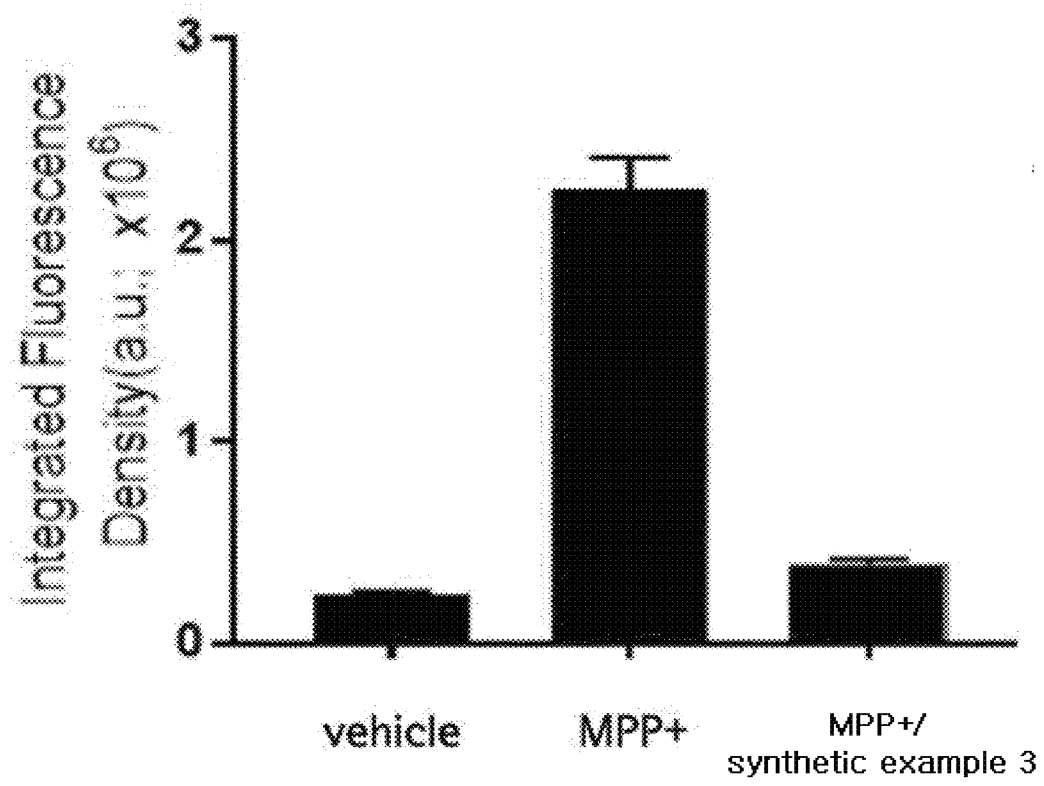

【FIG. 5】
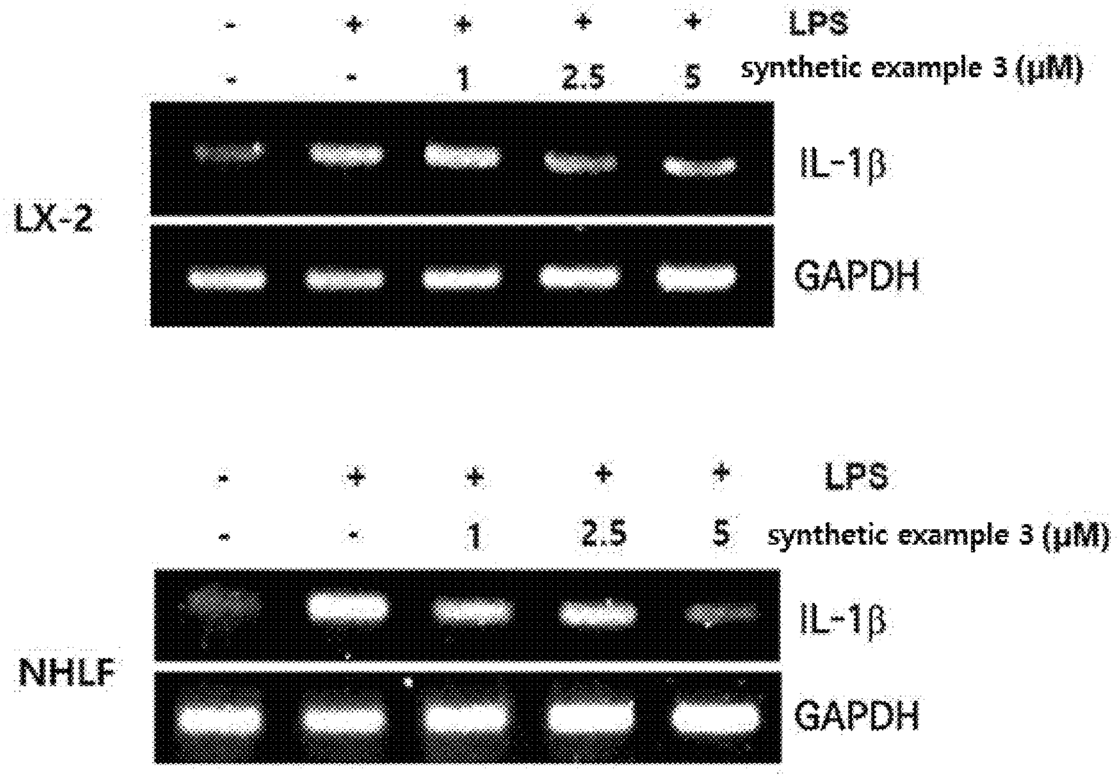

【FIG. 6】
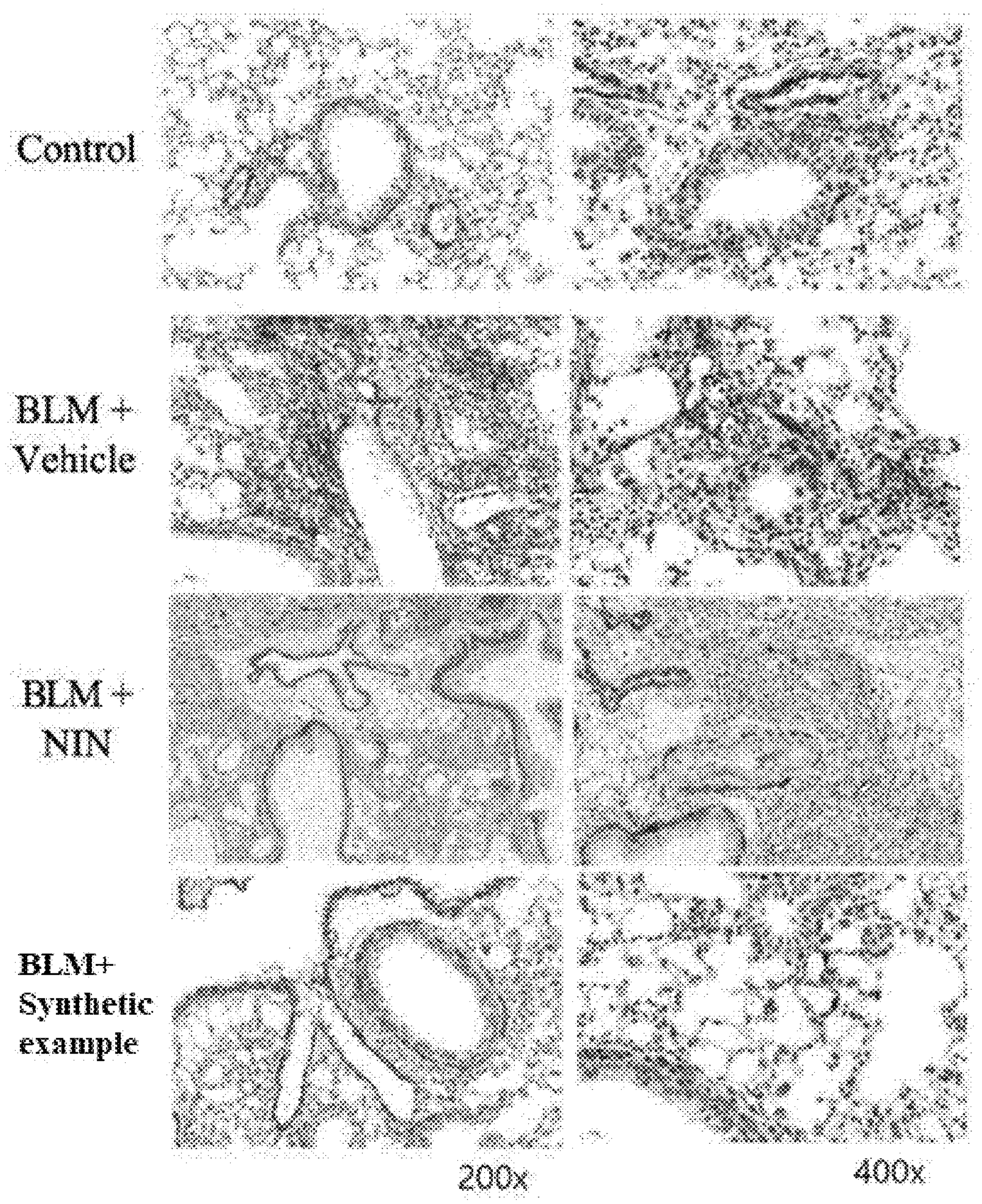

PYRAZOLE DERIVATIVE

TECHNICAL FIELD

The present application claims the benefit of the priority based on Korean Patent Application No. 10-2020-0004471 filed on Jan. 13, 2020, and the entire contents disclosed in the document of the corresponding Korean patent application are incorporated as a part of the present description.

The present invention relates to a novel pyrazole derivative with excellent inhibitory activity of oxidative stress, a method for preparing the same and a pharmaceutical composition thereof.

BACKGROUND ART

Oxidative s tress refers to a phenomenon in which production of reactive oxygen species or reactive nitrogen species and an antioxidant defense mechanism are out of balance in biomolecules, cells and tissues in vivo and the production of reactive oxygen species or reactive nitrogen species becomes relatively excessive, and in this case, tissue damage is usually caused.

Reactive oxygen species (ROS) collectively refer to oxygen free radicals produced due to chemical properties of oxygen and oxygen compounds derived therefrom, such as superoxide anion ($O_2$—.), hydogenperoxide ($H_2O_2$), a hydroxyl group (OH.), an alkoxyl group (RO.), a peroxyl group (ROO.), and the like. Reactive nitrogen species (RNS) collectively refer to highly reactive peroxinitrite ($ONOO^-$) produced by NOS (nitric oxide synthase) in vivo by nitrogen monoxide (NO.) and superoxide anion ($O_2$—.), and nitrogen dioxide (.$NO_2$), nitrosoperoxycarbonate ($ONOOCO_2^-$), carbonate radical (O═C(O.)$O^-$), and the like produced from peroxinitrite.

Since there reactive oxygen species or reactive nitrogen species are chemically very unstable and highly reactive, they induce inflammation around and act as a major factor in tissue fibrosis by causing extensive oxidative damage to enzymatic catalysis reaction, electron transfer in mitochondria, cell signaling system and gene expression, activation of transcription factors, and biomolecules, cells, tissues and the like in vivo. This oxidative damage causes various diseases in all tissues of the human body. Specifically, it is known that it is involved in development of cancer in tissue such as skin, kidney, heart, joint, lung, brain, blood vessel, intestinal tract and eye and the like and progression of the generated cancer, as well as it is known to play an important role in almost all diseases including cardiovascular disease, inflammation, fibrotic disease, diabetes and the like.

Recently, it is known that interaction between the tumor microenvironment and cancer cells plays a major role in tumor growth, metastasis and expression of anticancer agent resistance, and in this case, cancer associated fibroblast (CAF) plays an important role. It is known that the cancer associated fibroblast is activated by ROS to promote tumor immune evasion and acts on cancer malignancy and metastasis. Therefore, recently, the cancer associated fibroblast is emerging as a new target for cancer treatment.

It has been reported that in liver tissue of patients undergoing hepatic fibrosis, an increase in ROS production in hepatocytes is caused by TGF-β1 stimulation, thereby increasing expression of collagen and αSMA, which are important for fibrosis. It has been reported that ROS exacerbates pulmonary fibrosis in lung tissue of patients with idiopathic pulmonary fibrosis.

Brain is a highly metabolized tissue and therefore very vulnerable to oxidative damage. Therefore, many studies have been conducted to effectively remove ROS for treatment of various neurodegenerative diseases (Parkinson's disease, Huntington's disease, amyotrophic lateral sclerosis, Alzheimer's disease, multiple sclerosis, ischemic and traumatic brain injury, etc.), but without success. Recently, as it was found that ROS is an important factor in these brain diseases, the possibility of treatment through ROS inhibition was reported.

Keloid is a type of benign tumor disease in which connective tissue of skin proliferates pathologically, making hard bumps and the epidermis becomes thin and shiny and reddish. It has been reported that one of the reasons for occurrence and exacerbation of keloid is overexpression of connective tissue growth factor (CTGF) by ROS produced by TGF-β1 stimulation.

In case of diabetes, complications such as diabetic nephropathy and diabetic retinopathy may accompany long-term hyperglycemia, and ROS is known to play an important role in occurrence of complications. In other words, high blood sugar causes an increase in ROS production, and the ROS generated at this time may cause diabetic nephropathy and diabetic retinopathy and the like through a series of processes inducing death of kidney cells and retinal cells.

In addition, as observed in keloid disease, it has been reported that overexpression of the CTGF gene in the retina of eyes causes retinal fibrosis and macular degeneration.

Therefore, the present inventors have studied focusing on that a therapeutic agent for cancer, inflammatory disease, fibrotic disease, neurodegenerative disease, liver disease, skin disease or retinal disease caused by oxidative stress can be developed by using a molecular mechanism that inhibits production of oxidative stress, and as a result, they have found that the novel pyrazole derivative of the present invention has excellent inhibitory activity of ROS production and have confirmed that it can be used for treatment of various diseases related to oxidative stress, thereby completing the present invention.

PRIOR ART (Patent document 1) WO 2016-207785
(Patent document 2) WO 2015-144801
(Non-patent document 1) Mengjia Song, Xinfeng Chen, et al. Chinese Journal of Cancer Research, 2018, 30(2):157-172.
(Non-patent document 2) Lan T, Kisseleva T, Brenner D A. PLoS One 2015; 10:e0129743.
(Non-patent document 3) Merry W. Ma, Jin Wang, et al. Molecular neurodegeneration, 12:7, 2017.
(Non-patent document 4) Alessandro G. Fois. Panagiotis Paligiannis et al. Respir Res. 2018, 19:51.
(Non-patent document 5) Rohan Samarakoon, Jessica M. Overstreet et al. Cell Signal, 2013, Jan., 25(1), 264-268.

DISCLOSURE

Technical Problem

An object of the present invention is to provide a novel pyrazole derivative, a compound of Chemical formula I, a solvate, a stereoisomer or a pharmaceutically acceptable salt thereof.

An object of the present invention is to provide a pharmaceutical composition comprising a compound of Chemical formula I, a solvate, a stereoisomer or a pharmaceutically acceptable salt thereof and a pharmaceutically acceptable carrier.

An object of the present invention is to provide a method for regulating production of ROS using a compound of Chemical formula I, a solvate, a stereoisomer or a pharmaceutically acceptable salt thereof.

An object of the present invention is to provide a method for treating oxidative stress-related disease by administering a compound of Chemical formula I, a solvate, a stereoisomer or a pharmaceutically acceptable salt thereof into a subject.

An object of the present invention is to provide a method for preparing a compound of Chemical formula I.

An object of the present invention is to provide a use of a compound of Chemical formula I, a solvate, a stereoisomer or a pharmaceutically acceptable salt thereof, for preparation of a pharmaceutical composition for prevention or treatment of oxidative stress-related disease.

Technical Solution

In order to achieve the above objects, the present invention provides a novel pyrazole derivative, a compound represented by Chemical formula I below, a solvate, a stereoisomer or a pharmaceutically acceptable salt thereof.

<Chemical formula I>

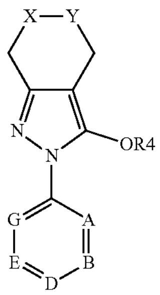

In the formula,

X, Y are CR1R2 or NR3; and

R1, R2 or R3 is same or different each other, and is each independently selected from Ra-L-, Ra-L-CO—, Ra-L-NHCO—, Ra-L-OCO—, Ra-L-$SO_2$—; and the Ra is selected from hydrogen, heavy hydrogen, cyan, halogen, nitro, haloalkyl, substituted or non-substituted C1-C10 linear or branched alkyl, substituted or non-substituted C3-C8 cycloalkyl, substituted or non-substituted C5-C20 aryl, or substituted or non-substituted C5-C20 heteroaryl, and the heteroaryl comprises 1, 2 or 3 heteroatoms among O, N and S; and the L is selected from direct boding, C1-C5 alkylene and substituted or non-substituted C5-C10 arylene; and the R4 is selected from hydrogen or substituted or non-substituted C1-C10 alkyl; and A is CR5 or N, B, and CR6 or N, D is CR7 or N, and E is CR8 or N, and G is CR9 or N; and the R5 to R9 are same or different, and are each independently selected from hydrogen, heavy hydrogen, cyan, halogen, haloalkyl, carbonyl, nitro, carboxyl, C1-C5 alkoxy, substituted or non-substituted C1-C10 linear or branched alkyl, substituted or non-substituted C3-C8 cycloalkyl, substituted or non-substituted amine, substituted or non-substituted C5-C20 aryl, or substituted or non-substituted C5-C20 heteroaryl, and two or more groups adjacent to each other may combine with each other to form a substituted or non-substituted aromatic hydrocarbon ring, wherein the aromatic hydrocarbon ring may form a C5-C10 heteroaryl ring or aryl ring comprising 0, 1, 2 or 3 heteroatoms selected from N, O and S; and the substituted C1-C10 linear or branched alkyl may be optionally partially unsaturated, and may be independently substituted to one or more substituents selected from heavy hydrogen, halogen, cyan, nitro, carboxyl, substituted or non-substituted amine, substituted or non-substituted C5-C20 aryl or C5-C20 heteroaryl, substituted or non-substituted C3-C8 cycloalkyl; and the substituted C3-C8 cycloalkyl may be substituted independently as one or more substituents selected from heavy hydrogen, halogen, cyan, nitro, carboxyl, substituted or non-substituted amine, substituted or non-substituted C5-C20 aryl or C5-C20 heteroaryl, C1-C5 alkoxy and C1-C5 haloalkyl or same or different 2 or more substituents are linked; and the substituted C5-C20 aryl or substituted C5-C20 heteroaryl may be substituted independently as one or more substituents selected from heavy hydrogen, halogen, cyan, nitro, carboxyl, substituted or non-substituted amine, C1-C5 alkoxy, C1-C5 haloalkyl, C1-C10 alkylC3-C8 cycloalkyl, C1-C10 alkyl, and C5-C20 arylC1-C10 alkyl or same or different 2 or more substituents are linked; and the substituted amine may be substituted to one or two of C1-C5 alkyl groups; and the substituted C5-C10 arylene may be substituted to one or more substituents selected from C1-C3 alkyl, halogen, cyan, amine, nitro and heavy chain or same or different 2 or more substituents are linked.

In addition, the present invention provides the compound represented by the Chemical formula I, solvate, stereoisomer or pharmaceutically acceptable salt used for treatment of oxidative stress-related disease.

Furthermore, the present invention provides a pharmaceutical composition for treating oxidative stress-related disease comprising the compound represented by the Chemical formula I, solvate, stereoisomer or pharmaceutically acceptable salt thereof and an acceptable carrier as an active ingredient.

Moreover, the present invention provides a method for treating oxidative stress-related disease comprising administering an effective dose of the compound represented by the Chemical formula I, solvate, stereoisomer or pharmaceutically acceptable salt thereof into a subject in need of treatment.

In addition, the present invention provides a use of the compound represented by the Chemical formula I, solvate, stereoisomer or pharmaceutically acceptable salt thereof, for preparation of a pharmaceutical composition for prevention or treatment of oxidative stress-related disease.

Advantageous Effects

The novel pyrazole derivative and pharmaceutical composition comprising the same of the present invention provide an excellent effect for oxidative stress-related disease.

In addition, the novel pyrazole derivative effectively inhibited oxidative stress and production of αSMA, extracellular matrix, or IL-1β in various cells, and in particular, it has an effect of effectively improving cancer, inflammatory disease, fibrous disease, neurodegenerative disease, liver disease, skin disease or retinal disease, or the like caused by oxidative stress.

BRIEF DESCRIPTION OF THE DRAWINGS

FIG. 1 shows an effect of Synthetic example compounds, inhibiting ROS production induced by PMA in LX-2 and NHLF cells.

FIG. 2 shows an effect of Synthetic example compounds, inhibiting expression of αSMA induced by TGF-β1 in ARPE19 cells.

FIG. 3*a* and FIG. 3*b* shows an effect of Synthetic example 3 compound inhibiting expression of αSMA induced by TGF-β1 in various cells.

FIG. 4 shows an effect of Synthetic example 3 compound, inhibiting production of ROS induced by MPP+ in N27 cells.

FIG. 5 shows an effect of Synthetic example 3 compound, inhibiting expression of IL-1β induced by LPS in LX-2 and NHLF cells.

FIG. 6 shows an effect of inhibiting expression of αSMA by Synthetic example compounds in lung tissue of a pulmonary fibrosis model.

BEST MODE

Hereinafter, the present invention will be described in detail by embodiments. However, they are presented as examples, and the present invention is not limited thereto, and the present invention is only defined by the scope of claims to be described later. In addition, even if it is a configuration essential for conducting the present invention, a detailed description of the configuration that can be easily implemented by those skilled in the art from known technology will be omitted.

Unless otherwise specified below, the term "compound of the present invention" or "compound of Chemical formula I" is used as a concept including all of the compound itself, solvates, stereoisomers and salts thereof.

In the present description, the term "linear or branched alkyl" means a linear, branched monovalent saturated hydrocarbon group. Unless otherwise defined, the alkyl group generally comprises 1~10, 1~8, 1~6, 1~4 or 1~3 carbon atoms. The example of the alkyl group includes methyl, ethyl, propyl (e.g. n-propyl and isopropyl), butyl (e.g. n-butyl, isobutyl, and t-butyl), pentyl (e.g. n-pentyl, isopentyl, and neopentyl), n-hexyl, n-heptyl, n-octyl, n-nonyl and n-decyl. In the present description, the alkyl group may be optionally partially unsaturated and be alkenyl or alkynyl below. In addition, the alkyl group may be further substituted by other substituents.

In the present description, the term "alkenyl" means a linear or branched monovalent unsaturated hydrocarbon group having one or more carbon-carbon double bonds. Unless otherwise defined, the alkenyl group generally comprises 2~10, 2~8, 2~6, 2~4 or 2~3 carbon atoms. The alkenyl group includes for example, ethenyl, n-prophenyl, isoprophenyl, cyclohexenyl, and the like, and may be further substituted by other substituents.

In the present description, the term "alkynyl" means a linear or branched monovalent unsaturated hydrocarbon group having 1 or more carbon-carbon triple bonds. Unless otherwise defined, the alkynyl group generally comprises 2~10, 2~8, 2~6, 2~4 or 2~3 carbon atoms. The alkynyl group includes for example, ethynyl, n-propynyl, and the like, and may be further substituted by other substituents.

In the present description, the term "alkoxy" may be a linear chain, branched chain or ring chain. The carbon number of the alkoxy group is not particularly limited, but the carbon number is preferably 1 to 5. Specifically, it may be methoxy, ethoxy, n-propoxy, isopropoxy, n-butoxy, isobutoxy, tert-butoxy, sec-butoxy, n-pentyloxy, neopentyl, isopentyl, and the like, but not limited thereto.

In the present description, the term "haloalkyl" means an alkyl group having one or more halogen substituents. The haloalkyl includes $—CF_3$, $—C_2F_5$, $—CHF_2$, $—CCl_3$, $—CHCl_2$, and $—C_2Cl_5$. Unless otherwise defined, the haloalkyl group generally comprises 1~6, 1~5, 1~4 or 1~3 carbon atoms, and may be further substituted by other substituents.

In the present description, the term "cycloalkyl" represents a non-aromatic carbon ring comprising a cyclized alkyl, alkenyl and alkynyl groups. The cycloalkyl group may comprise a monocyclic or polycyclic ring. The polycyclic ring has for example, 2, 3 or 4 fused rings. Unless otherwise defined, the cycloalkyl group generally comprises 3 to 10 or 3 to 7 cyclic carbon atoms. The cycloalkyl group includes cyclopropyl, cyclobutyl, cyclopentyl, cyclohexyl, cycloheptyl, cyclohexadienyl, cycloheptatrienyl, and the like, and may be further substituted by other substituents.

In the present description, the term "aryl" means an aromatic hydrocarbon group having a monocylic or polycyclic ring, and may be further substituted by other substituents. Herein, the polycyclic means a group in which an aryl group is directly connected to condensed with another ring group. Herein, the other ring group may be an aryl group, but may be a different kind of ring group, for example, cycloalkyl group, heteroaryl group, and the like. The polycyclic ring may have for example, 2, 3 or 4 rings. Unless otherwise defined, the aryl group generally has 5 to 20, 6 to 15, 6 to 12 or 6 to 10 carbon ring atoms. The aryl group includes for example, phenyl, naphthyl (e.g., naphthyl-1-yl and naphthyl-2-yl), non-phenyl, anthracenyl, phenanthreneyl, and the like.

In the present description, the term "heteroaryl" means a monovalent aromatic group having one or more heteroatoms selected from N, O and S as a ring member. The heteroaryl group comprises a monocylic or heterocyclic structure. The polycyclic ring may have for example, 2, 3 or 3 condensed rings. Unless otherwise defined, the heteroaryl group generally comprises 3 to 10, 3 to 7 or 3 to 5 ring atoms. The heteroaryl group may have 1, 2 or 3 heteroatoms. The heteroaryl group includes for example, furanyl, pyridyl, N-oxopyridyl, pyrimidyl, pirazinyl, piridazinyl, triazinyl, furyl, quinolyl, isoquinolyl, thienyl, imidazolyl, furanyl, thiazolyl, indolyl, pyrryl, oxazolyl, benzofuryl, benzothienyl, benzthiazolyl, isooxazolyl, pyrazolyl, triazolyl, tetrazolyl, indazolyl, 1,2,4-thiadiazolyl, isothiazolyl, benzothienyl, furinyl, benzimidazolyl, indolinyl, and the like, and may be further substituted by other substituents.

In the present description, the term "halogen" represents fluoro, chloro, bromo or iodo.

In the present description, the term "arylalkyl" represents an alkyl group substituted by an aryl group. "Aryl" and "alkyl" are as defined above.

In the present description, the term "heteroarylalkyl" represents an alkyl group substituted by a heteroaryl group. "Heteroaryl" and "alkyl" are as defined above.

In the present description, the "substituted or non-substituted amine group" may be selected from the group consisting of monoalkylamine group, —NH2, and dialkylamine group, and "alkyl" is as defined above. The specific example of the substituted or non-substituted amine group includes NH2, methylamine group, dimethylamine group, ethylamine group, diethylamine group and the like, but not limited thereto.

In the present description, the "arylene group" means that the aryl group has two boding sites, that is, a divalent group. Except that each of them is a divalent group, the description of the aforementioned aryl group may be applied.

In the present description, the term "substitution" means that a hydrogen atom bound to a carbon atom of a compound is replaced with another substituent, and the position to be substituted is not limited as long as the position at which the hydrogen atom is substituted, that is, a position where the substituent is substitutable, and when two or more substituents are substituted, two or more substituents may be same or different from each other, and two or more same or different substituents may be linked and substituted.

In the present description, the term "substituted linear or branched alkyl" is a form in which a carbon atom of C1-C10 linear or branched alkyl is substituted with the following substituent. Specifically, it is a form in which one or more substituents selected from heavy hydrogen, halogen, cyan, nitro, carboxyl, substituted or non-substituted amine, substituted or non-substituted C5-C20 aryl or C5-C20 heteroaryl, C1-C5 alkoxy, and C1-C5 haloalkyl, or same or different 2 or more substituents are linked and substituted. As an exemplary substituent, trifluoromethyl, halogen, cyan, methoxy, carboxyl, methyl, amino, nitro, dimethylamino, cyclcopropyl, substituted imidazole, and the like may be used, but not limited thereto.

The term in the present description, "substituted cycloalkyl" is a form in which one or more substituents selected from heavy hydrogen, halogen, cyan, nitro, carboxyl, substituted or non-substituted amine, substituted or non-substituted C5-C20 aryl or C5-C20 heteroaryl, C1-C5 alkoxy, and C1-C5 haloalkyl, or same or different 2 or more substituents are linked and substituted to C3-C8 cycloalkyl. As an exemplary substituent, trifluoromethyl, halogen, cyan, methoxy, carboxyl, methyl, amino, nitro, dimethylamino, cyclopropyl, substituted imidazole, and the like may be used, but not limited thereto.

The term in the present description, "substituted aryl" or "substituted heteroaryl" is a form in which one or more substituents selected from heavy hydrogen, halogen, cyan, nitro, carboxyl, substituted or non-substituted amine, C1-C5 alkoxyl, C1-C5 haloalkyl, C1-C10 alkyl, C3-C8 cycloalkyl, C1-C10 alkyl, C5-C20 aryl, and C1-C10 alkyl, or same or different 2 or more substituents are linked and substituted to C5-C20 aryl or C5-C50 heteroaryl. As an exemplary substituent, trifluoromethyl, halogen, cyan, methoxy, carboxyl, methyl, amino, nitro, dimethylamino, cyclopropyl, substituted imidazole, and the like may be used, but not limited thereto.

In the present description, the "adjacent" group may mean a substituent substituted to an atom directly connected to an atom in which the corresponding substituent is substituted, a substituent sterically closest to the corresponding substituent, or another substituent substituted to an atom in which the corresponding substituent is substituted. For example, two substituents substituted at the ortho position in a benzene ring and two substituents substituted at the same carbon in an aliphatic ring may be interpreted as an "adjacent" group to each other.

The present invention provides a compound represented by Chemical formula I below, a solvate, a stereoisomer or a pharmaceutically acceptable salt.

<Chemical formula I>

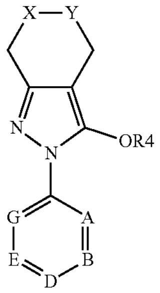

In the formula,

X, Y are CR1R2 or NR3; and

R1, R2 or R3 is same or different each other, and is each independently selected from Ra-L-, Ra-L-CO—, Ra-L-NHCO—, Ra-L-OCO—, Ra-L-$SO_2$—; and the Ra is selected from hydrogen, heavy hydrogen, cyan, halogen, nitro, haloalkyl, substituted or non-substituted C1-C10 linear or branched alkyl, substituted or non-substituted C3-C8 cycloalkyl, substituted or non-substituted C5-C20 aryl, or substituted or non-substituted C5-C20 heteroaryl, and the heteroaryl comprises 1, 2 or 3 heteroatoms among O, N and S; and the L is selected from direct boding, C1-C5 alkylene and substituted or non-substituted C5-C10 arylene; and the R4 is selected from hydrogen or substituted or non-substituted C1-C10 alkyl; and A is CR5 or N, B, and CR6 or N, D is CR7 or N, and E is CR8 or N, and G is CR9 or N; and the R5 to R9 are same or different, and are each independently selected from hydrogen, heavy hydrogen, cyan, halogen, haloalkyl, carbonyl, nitro, carboxyl, C1-C5 alkoxy, substituted or non-substituted C1-C10 linear or branched alkyl, substituted or non-substituted C3-C8 cycloalkyl, substituted or non-substituted amine, substituted or non-substituted C5-C20 aryl, or substituted or non-substituted C5-C20 heteroaryl, and two or more groups adjacent to each other may combine with each other to form a substituted or non-substituted aromatic hydrocarbon ring, wherein the aromatic hydrocarbon ring may form a C5-C10 heteroaryl ring or aryl ring comprising 0, 1, 2 or 3 heteroatoms selected from N, O and S; and the substituted C1-C10 linear or branched alkyl may be optionally partially unsaturated, and may be independently substituted to one or more substituents selected from heavy hydrogen, halogen, cyan, nitro, carboxyl, substituted or non-substituted amine, substituted or non-substituted C5-C20 aryl or C5-C20 heteroaryl, substituted or non-substituted C3-C8 cycloalkyl; and the substituted C3-C8 cycloalkyl may be substituted independently as one or more substituents selected from heavy hydrogen, halogen, cyan, nitro, carboxyl, substituted or non-substituted amine, substituted or non-substituted C5-C20 aryl or C5-C20 heteroaryl, C1-C5 alkoxy and C1-C5 haloalkyl or same or different 2 or more substituents are linked; and the substituted C5-C20 aryl or substituted C5-C20 heteroaryl may be substituted independently as one or more substituents selected from heavy hydrogen, halogen, cyan, nitro, carboxyl, substituted or non-substituted amine, C1-C5 alkoxy, C1-C5 haloalkyl, C1-C10 alkylC3-C8 cycloalkyl, C1-C10 alkyl, and C5-C20 arylC1-C10 alkyl or same or different 2 or more substituents are linked;

the substituted amine may be substituted to one or two of C1-C5 alkyl groups; and the substituted C5-C10 arylene may be substituted to one or more substituents selected from C1-C3 alkyl, halogen, cyan, amine, nitro and heavy chain or same or different 2 or more substituents are linked.

Additionally, the Chemical formula I is represented by Chemical formula I-1 below.

<Chemical formula I-1>

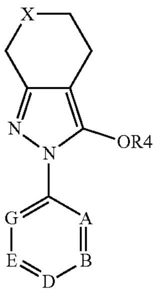

In the formula,

X is NR3, and

R3 is selected from Ra-L-, Ra-L-CO—, Ra-L-NHCO—, Ra-L-OCO— and Ra-L-$SO_2$—; and the Ra is selected from hydrogen, heavy hydrogen, cyan, halogen, nitro, haloalkyl, substituted or non-substituted C1-C10 linear or branched alkyl, substituted or non-substituted C3-C8 cycloalkyl, substituted or non-substituted C5-C20 aryl, or substituted or non-substituted C5-C20 heteroaryl, and the heteroaryl comprises 1, 2 or 3 heteroatoms among O, N and S; and the L is selected from direct bonding, C1-C5 alkylene, or substituted or non-substituted C5-C10 arylene; and the R4 is selected from hydrogen or substituted or non-substituted C1-C10 alkyl; and A is CR5 or N, and B is CR6 or N, and D is CR7 or N, and E is CR8 or N, and G is CR9 or N; and the R5 to R9 are same or different, and are each independently selected from hydrogen, heavy hydrogen, cyan, halogen, haloalkyl, carbonyl, nitro, carboxyl, C1-C5 alkoxy, substituted or non-substituted C1-C10 linear or branched alkyl, substituted or non-substituted C3-C8 cycloalkyl, substituted or non-substituted amine, substituted or non-substituted C5-C20 aryl, or substituted or non-substituted C5-C20 heteroaryl, and two or more groups adjacent to each other may combine with each other to form a substituted or non-substituted aromatic hydrocarbon ring, wherein the aromatic hydrocarbon ring may form a C5-C10 heteroaryl ring or aryl ring comprising 0, 1, 2 or 3 heteroatoms selected from N, O and S; and the substituted C1-C10 linear or branched alkyl may be optionally partially unsaturated, and may be independently substituted to one or more substituents selected from heavy hydrogen, halogen, cyan, nitro, carboxyl, substituted or non-substituted amine, substituted or non-substituted C5-C20 aryl or C5-C20 heteroaryl, substituted or non-substituted C3-C8 cycloalkyl; and the substituted C3-C8 cycloalkyl may be substituted independently as one or more substituents selected from heavy hydrogen, halogen, cyan, nitro, carboxyl, substituted or non-substituted amine, substituted or non-substituted C5-C20 aryl or C5-C20 heteroaryl, C1-C5 alkoxy and C1-C5 haloalkyl or same or different 2 or more substituents are linked; and the substituted C5-C20 aryl or substituted C5-C20 heteroaryl may be substituted independently as one or more substituents selected from heavy hydrogen, halogen, cyan, nitro, carboxyl, substituted or non-substituted amine, C1-C5 alkoxy, C1-C5 haloalkyl, C1-C10 alkylC3-C8 cycloalkyl, C1-C10 alkyl, and C5-C20 arylC1-C10 alkyl or same or different 2 or more substituents are linked;

the substituted amine may be substituted to one or two of C1-C5 alkyl groups; and the substituted C5-C10 arylene may be substituted to one or more substituents selected from C1-C3 alkyl, halogen, cyan, amine, nitro and heavy chain or same or different 2 or more substituents are linked.

Additionally, the Chemical formula I is represented by Chemical formula 1-2 below.

<Chemical formula I-2>

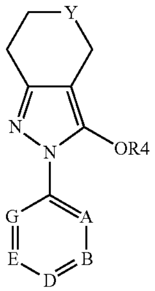

In the formula,

Y is NR3, and

R3 is selected from Ra-L-, Ra-L-CO—, Ra-L-NHCO—, Ra-L-OCO— and Ra-L-$SO_2$—; and the Ra is selected from hydrogen, heavy hydrogen, cyan, halogen, nitro, haloalkyl, substituted or non-substituted C1-C10 linear or branched alkyl, substituted or non-substituted C3-C8 cycloalkyl, substituted or non-substituted C5-C20 aryl, or substituted or non-substituted C5-C20 heteroaryl, and the heteroaryl comprises 1, 2 or 3 heteroatoms among O, N and S; and the L is selected from direct bonding, C1-C5 alkylene, or substituted or non-substituted C5-C10 arylene; and the R4 is selected from hydrogen or substituted or non-substituted C1-C10 alkyl; and A is CR5 or N, and B is CR6 or N, and D is CR7 or N, and E is CR8 or N, and G is CR9 or N; and the R5 to R9 are same or different, and are each independently selected from hydrogen, heavy hydrogen, cyan, halogen, haloalkyl, carbonyl, nitro, carboxyl, C1-C5 alkoxy, substituted or non-substituted C1-C10 linear or branched alkyl, substituted or non-substituted C3-C8 cycloalkyl, substituted or non-substituted amine, substituted or non-substituted C5-C20 aryl, or substituted or non-substituted C5-C20 heteroaryl, and two or more groups adjacent to each other may combine with each other to form a substituted or non-substituted aromatic hydrocarbon ring, wherein the aromatic hydrocarbon ring may form a C5-C10 heteroaryl ring or aryl ring comprising 0, 1, 2 or 3 heteroatoms selected from N, O and S; and the substituted C1-C10 linear or branched alkyl may be optionally partially unsaturated, and may be independently substituted to one or more substituents selected from heavy hydrogen, halogen, cyan, nitro, carboxyl, substituted or non-substituted amine, substituted or non-substituted C5-C20 aryl or C5-C20 heteroaryl, substituted or non-substituted C3-C8 cycloalkyl; and the substituted C3-C8 cycloalkyl may be substituted independently as one or more substituents selected from heavy hydrogen, halogen, cyan, nitro, carboxyl, substituted or non-substituted amine, substituted or non-substituted C5-C20 aryl or C5-C20 heteroaryl, C1-C5 alkoxy and C1-C5 haloalkyl or same or different 2 or more substituents are linked; and the substituted C5-C20 aryl or substituted C5-C20 heteroaryl may be substituted independently as one or more substituents selected from heavy hydrogen, halogen, cyan, nitro, carboxyl, substituted or non-substituted amine, C1-C5 alkoxy, C1-C5 haloalkyl, C1-C10 alkylC3-C8 cycloalkyl, C1-C10 alkyl, and C5-C20 arylC1-C10 alkyl or same or different 2 or more substituents are linked;

the substituted amine may be substituted to one or two of C1-C5 alkyl groups; and the substituted C5-C10 arylene may be substituted to one or more substituents selected from C1-C3 alkyl, halogen, cyan, amine, nitro and heavy chain or same or different 2 or more substituents are linked.

In addition, in the compound of Chemical formula I-1 or I-2, the R3 is Ra-L; and L is selected from direct bonding and C1-C3 alkylene; and N in A, B, D, E, G is 0 or 1; and the R5 to R9 are same or different, and are each independently selected from hydrogen, heavy hydrogen, cyan, halogen, haloalkyl, carbonyl, nitro, carboxyl, C1-C5 alkoxy, C1-C5 alkyl, C1-C5 haloalkyl in which one or more halogens are substituted, substituted or non-substituted C3-C8 cycloalkyl, substituted or non-substituted amine, substituted or non-substituted C5-C10 aryl, or substituted or non-substituted C5-C10 heteroaryl, and two or more groups adjacent to each other may combine with each other to form a substituted or non-substituted aromatic hydrocarbon ring, wherein the aromatic hydrocarbon ring may form a C5-C10 heteroaryl ring or aryl ring comprising 0, 1, 2 or 3 heteroatoms selected from N, O and S; and R4 may be selected from hydrogen or substituted or non-substituted C1-C5 alkyl.

In addition, in the compound of Chemical formula I-1 or I-2, the R3 is Ra-L-CO—; and L is selected from direct bonding, C1-C3 alkylene and substituted phenylene, and N in A, B, D, E, G is 0 or 1; and the R5 to R9 are same or different, and are each independently selected from hydrogen, heavy hydrogen, cyan, halogen, haloalkyl, carbonyl, nitro, carboxyl, C1-C5 alkoxy, C1-C5 alkyl, C1-C5 haloalkyl in which one or more halogens are substituted, substituted or non-substituted C3-C8 cycloalkyl, substituted or non-substituted amine, substituted or non-substituted C5-C10 aryl, or substituted or non-substituted C5-C10 heteroaryl, and two or more groups adjacent to each other may combine with each other to form a substituted or non-substituted aromatic hydrocarbon ring, wherein the aromatic hydrocarbon ring may form a C5-C10 heteroaryl ring or aryl ring comprising 0, 1, 2 or 3 heteroatoms selected from N, O and S; and R4 may be selected from hydrogen or substituted or non-substituted C1-C5 alkyl.

In addition, in the compound of Chemical formula I-1 or I-2, the R3 is Ra-L-NHCO—; and L is selected from direct bonding and C1-C3 alkylene; and N in A, B, D, E, G is 0 or 1; and the R5 to R9 are same or different, and are each independently selected from hydrogen, heavy hydrogen, cyan, halogen, haloalkyl, carbonyl, nitro, carboxyl, C1-C5 alkoxy, C1-C5 alkyl, C1-C5 haloalkyl in which one or more halogens are substituted, substituted or non-substituted C3-C8 cycloalkyl, substituted or non-substituted amine, substituted or non-substituted C5-C10 aryl, or substituted or non-substituted C5-C10 heteroaryl, and two or more groups adjacent to each other may combine with each other to form a substituted or non-substituted aromatic hydrocarbon ring, wherein the aromatic hydrocarbon ring may form a C5-C10 heteroaryl ring or aryl ring comprising 0, 1, 2 or 3 heteroatoms selected from N, O and S; and R4 may be selected from hydrogen or substituted or non-substituted C1-C5 alkyl.

Additionally, in the compound of Chemical formula I-1 or I-2, the R3 is Ra-L-OCO—; and L is selected from direct bonding and C1-C3 alkylene, and N in A, B, D, E, G is 0 or 1; and the R5 to R9 are same or different, and are each independently selected from hydrogen, heavy hydrogen, cyan, halogen, haloalkyl, carbonyl, nitro, carboxyl, C1-C5 alkoxy, C1-C5 alkyl, C1-C5 haloalkyl in which one or more halogens are substituted, substituted or non-substituted C3-C8 cycloalkyl, substituted or non-substituted amine, substituted or non-substituted C5-C10 aryl, or substituted or non-substituted C5-C10 heteroaryl, and two or more groups adjacent to each other may combine with each other to form a substituted or non-substituted aromatic hydrocarbon ring, wherein the aromatic hydrocarbon ring may form a C5-C10 heteroaryl ring or aryl ring comprising 0, 1, 2 or 3 heteroatoms selected from N, O and S; and R4 may be selected from hydrogen or substituted or non-substituted C1-C5 alkyl.

Additionally, in the compound of Chemical formula I-1 or I-2, the R3 is Ra-L-$SO_2$—; and L is selected from direct bonding and C1-C3 alkylene, and N in A, B, D, E, G is 0 or 1; and the R5 to R9 are same or different, and are each independently selected from hydrogen, heavy hydrogen, cyan, halogen, haloalkyl, carbonyl, nitro, carboxyl, C1-C5 alkoxy, C1-C5 alkyl, C1-C5 haloalkyl in which one or more halogens are substituted, substituted or non-substituted C3-C8 cycloalkyl, substituted or non-substituted amine, substituted or non-substituted C5-C10 aryl, or substituted or non-substituted C5-C10 heteroaryl, and two or more groups adjacent to each other may combine with each other to form a substituted or non-substituted aromatic hydrocarbon ring, wherein the aromatic hydrocarbon ring may form a C5-C10 heteroaryl ring or aryl ring comprising 0, 1, 2 or 3 heteroatoms selected from N, O and S; and R4 may be selected from hydrogen or substituted or non-substituted C1-C5 alkyl.

The compound of Chemical formula I may be any one of the following compounds.

2-(pyridin-2-yl)-4,5,6,7-tetrahydro-2H-indazol-3-ol;

2-(5-(trifluoromethyl)pyridin-2-yl)-4,5,6,7-tetrahydro-2H-indazol-3-ol;

6-benzyl-2-(pyridin-2-yl)-4,5,6,7-tetrahydro-2H-pyrazolo[3,4-c]pyridin-3-ol;

6-benzyl-2-(pyridin-2-yl)-4,5,6,7-tetrahydro-2H-pyrazolo[3,4-c]pyridin-3-ol;

6-benzyl-2-(5 (trifluoromethyl)pyridin-2-yl)-4,5,6,7-tetrahydro-2H-pyrazolo[3,4-c]pyridin-3-ol;

6-(4-fluorobenzyl)-2-(pyridin-2-yl)-4,5,6,7-tetrahydro-2H-pyrazolo[3,4-c]pyridin-3-ol;
6-(4-methylbenzyl)-2-(pyridin-2-yl)-4,5,6,7-tetrahydro-2H-pyrazolo[3,4-c]pyridin-3-ol;
4-((3-hydroxy-2-(pyridin-2-yl)-2,4,5,7-tetrahydro-2H-pyrazolo[3,4-c]pyridin yl)methyl)benzonitrile;
6-(3,5-difluorobenzyl)-2-(pyridin-2-yl)-4,5,6,7-tetrahydro-2H-pyrazolo[3,4-c]pyridin ol;
2-(pyridin-2-yl)-6-(3 (trifluoromethyl)benzyl)-4,5,6,7-tetrahydro-2H-pyrazolo[3,4-c]pyridin-3-ol;
6-(naphthalene-2-ylmethyl)-2-(pyridin-2-yl)-4,5,6,7-tetrahydro-2H-pyrazolo[3,4-c]pyridin-3-ol;
1-(4,5-dihydro-3-hydroxy-2-(pyridin-2-yl)-2H-pyrazolo[3,4-c]pyridin-6(7H)-yl)butan-1-one;
1-(3-hydroxy-2-(pyridin-2-yl)-2,4,5,7-tetrahydro-6H-pyrazolo[3,4-c]pyridin-6-yl)ethan-1-one;
6-(4-methoxybenzyl)-2-(pyridin-2-yl)-4,5,6,7-tetrahydro-2H-pyrazolo[3,4-c]pyridin-3-ol;
6-ethyl-2-(pyridin-2-yl)-4,5,6,7-tetrahydro-2H-pyrazolo[3,4-c]pyridin-3-ol;
6-(prop-2-yn-1-yl)-2-(pyridin-2-yl)-4,5,6,7-tetrahydro-2H-pyrazolo[3,4-c]pyridin-3-ol;
6-propyl-2-(pyridin-2-yl)-4,5,6,7-tetrahydro-2H-pyrazolo[3,4-c]pyridin-3-ol;
6-allyl-2-(pyridin-2-yl)-4,5,6,7-tetrahydro-2H-pyrazolo[3,4-c]pyridin-3-ol;
(3-hydroxy-2-(pyridin-2-yl)-2,4,5,7-tetrahydro-6H-pyrazolo[3,4-c]pyridin yl)(phenyl)methanone;
benzyl 3-hydroxy-2-(pyridin-2-yl)-2,4,5,7-tetrahydro-6H-pyrazolo[3,4-c]pyridin carboxylate;
(4-chlorophenyl)(3-hydroxy-2-(pyridin-2-yl)-2,4,5,7-tetrahydro-6H-pyrazolo[3,4-c]pyridin-5-yl)methanone;
ethyl 3-hydroxy-2-(pyridin-2-yl)-2,4,5,7-tetrahydro-6H-pyrazolo[3,4-c]pyridin carboxylate;
N-cyclohexyl-3-hydroxy-2-(pyridin-2-yl)-2,4,5,7-tetrahydro-6H-pyrazolo[3,4-c]pyridin-6-carboxamide;
furan-2-yl(3-hydroxy-2-(pyridin-2-yl)-2,4,5,7-tetrahydro-6H-pyrazolo[3,4-c]pyridin-6-yl)methanone;
6-(methylsulfonyl)-2-(pyridin-2-yl)-4,5,6,7-tetrahydro-2H-pyrazolo[3,4-c]pyridin-3-ol;
6-(phenylsulfonyl)-2-(pyridin-2-yl)-4,5,6,7-tetrahydro-2H-pyrazolo[3,4-c]pyridin-3-ol;
N-(4-fluorophenyl)-3-hydroxy-2-(pyridin-2-yl)-2,4,5,7-tetrahydro-6H-pyrazolo[3,4-c]pyridin-6-carboxamide;
N-(4-fluorobenzyl)-3-hydroxy-2-(pyridin-2-yl)-2,4,5,7-tetrahydro-6H-pyrazolo[3,4-c]pyridin-6-carboxamide;
N-(furan-2-ylmethyl)-3-hydroxy-2-(pyridin-2-yl)-2,4,5,7-tetrahydro-6H-pyrazolo[3,4-c]pyridin-6-carboxamide;
N-(4-chlorophenethyl)-3-hydroxy-2-(pyridin-2-yl)-2,4,5,7-tetrahydro-6H-pyrazolo[3,4-c]pyridin-6-carboxamide;
6-(naphthalene-2-ylsulfonyl)-2-(pyridin-2-yl)-4,5,6,7-tetrahydro-2H-pyrazolo[3,4-c]pyridin-3-ol;
4-nitrobenzyl 3-hydroxy-2-(pyridin-2-yl)-2,4,5,7-tetrahydro-6H-pyrazolo[3,4-c]pyridin-6-carboxylate;
(5-(4-cyclopropyl-1H-imidazol-1-yl)-2-fluoro-4-methylphenyl)(3-hydroxy-2-(pyridin yl)-2,4,5,7-tetrahydro-6H-pyrazolo[3,4-c]pyridin-6-yl)methanone;
5-benzyl-2-(pyridin-2-yl)-4,5,6,7-tetrahydro-2H-pyrazolo[4,3-c]pyridin-3-ol;
6-benzyl-2-(5-chloropyridin-2-yl)-4,5,6,7-tetrahydro-2H-pyrazolo[3,4-c]pyridin-3-ol;
4-(6-benzyl-3-hydroxy-4,5,6,7-tetrahydro-2H-pyrazolo[3,4-c]pyridin-2-yl)benzoic acid;
6-benzyl-2-(4-bromophenyl)-4,5,6,7-tetrahydro-2H-pyrazolo[3,4-c]pyridin-3-ol;
6-benzyl-2-phenyl-4,5,6,7-tetrahydro-2H-pyrazolo[3,4-c]pyridin-3-ol;
5-benzyl-2-(5-trifluoromethyl)pyridin-2-yl)-4,5,6,7-tetrahydro-2H-pyrazolo[4,3-c]pyridin-3-ol;
5-benzyl-2-phenyl-4,5,6,7-tetrahydro-2H-pyrazolo[4,3-c]pyridin-3-ol;
5-benzyl-2-(4-bromophenyl)-4,5,6,7-tetrahydro-2H-pyrazolo[4,3-c]pyridin-3-ol;
5-benzyl-2-(2-chlorophenyl)-4,5,6,7-tetrahydro-2H-pyrazolo[4,3-c]pyridin-3-ol;
6-benzyl-2-(2-chlorophenyl)-4,5,6,7-tetrahydro-2H-pyrazolo[3,4-c]pyridin-3-ol;
6-benzyl-2-(2-methoxyphenyl)-4,5,6,7-tetrahydro-2H-pyrazolo[3,4-c]pyridin-3-ol;
5-benzyl-2-(5-chloropyridin-2-yl)-4,5,6,7-tetrahydro-2H-pyrazolo[4,3-c]pyridin-3-ol;
5-benzyl-2-(6-methyl-4-(trifluoromethyl)pyridin-2-yl)-4,5,6,7-tetrahydro-2H-pyrazolo[4,3-c]pyridin-3-ol;
5-benzyl-2-(thieno[3,2-c]pyridin-4-yl)-4,5,6,7-tetrahydro-2H-pyrazolo[4,3-c]pyridin-3-ol;
5-(naphthalene-2-ylmethyl)-2-(pyridin-2-yl)-4,5,6,7-tetrahydro-2H-pyrazolo[4,3-c]pyridin-3-ol;
5-(naphthalene-2-ylmethyl)-2-(5 (trifluoromethyl)pyridin-2-yl)-4,5,6,7-tetrahydro-2H-pyrazolo[4,3-c]pyridin-3-ol;
5-(3-(trifluoromethyl)benzyl)-2-(5 (trifluoromethyl)pyridin-2-yl)-4,5,6,7-tetrahydro pyrazolo[4,3-c]pyridin-3-ol;
5-(3,5-difluorobenzyl)-2-(pyridin-2-yl)-4,5,6,7-tetrahydro-2H-pyrazolo[4,3-c]pyridin ol;
5-(3,5-difluorobenzyl)-2-(5 trifluoromethyl)pyridin-2-yl)-4,5,6,7-tetrahydro-2H-pyrazolo[4,3-c]pyridin-3-ol;
6-benzyl-3-methoxy-2-(pyridin-2-yl)-4,5,6,7-tetrahydro-2H-pyrazolo[3,4-c]pyridine; 6-(6-benzyl-3-hydroxy-4,5,6,7-tetrahydro-2H-pyrazolo[3,4-c]pyridin-2-yl)nicotinonitrile;
6-benzyl-2-(6-(trifluoromethyl)pyridin-2-yl)-4,5,6,7-tetrahydro-2H-pyrazolo[3,4-c]pyridin-3-ol;
6-benzyl-2-(3-fluoropyridin-2-yl)-4,5,6,7-tetrahydro-2H-pyrazolo[3,4-c]pyridin-3-ol;
6-benzyl-2-(6-methylpyridin-2-yl)-4,5,6,7-tetrahydro-2H-pyrazolo[3,4-c]pyridin-3-ol;
6-benzyl-2-(6-methyl-4-(trifluoromethyl)pyridin-2-yl)-4,5,6,7-tetrahydro-2H-pyrazolo[3,4-c]pyridin-3-ol;
5-benzyl-2-(6-methylpyridin-2-yl)-4,5,6,7-tetrahydro-2H-pyrazolo[4,3-c]pyridin-3-ol;
5-benzyl-2-(6-trifluoromethyl)pyridin-2-yl)-4,5,6,7-tetrahydro-2H-pyrazolo[4,3-c]pyridin-3-ol;
6-(5-benzyl-3-hydroxy-4,5,6,7-tetrahydro-2H-pyrazolo[4,3-c]pyridin-2-yl)nicotinonitrile;
5-benzyl-2-(3-fluoropyridin-2-yl)-4,5,6,7-tetrahydro-2H-pyrazolo[4,3-c]pyridin-3-ol;
5-benzyl-2-(thieno[3,2-c]pyridin-4-yl)-4,5,6,7-tetrahydro-2H-pyrazolo[4,3-c]pyridin ol;
5-benzyl-2-(6-methyl-4-(trifluoromethyl)pyridin-2-yl)-4,5,6,7-tetrahydro-21 pyrazolo[4,3-c]pyridin-3-ol;
6-benzyl-2-(thieno[3,2-c]pyridin-4-yl)-4,5,6,7-tetrahydro-2H-pyrazolo[3,4-c]pyridin ol;
2-(pyridin-2-yl)-6-(pyridin-2-ylmethyl)-4,5,6,7-tetrahydro-2H-pyrazolo[3,4-c]pyridin ol;
2-(pyridin-2-yl)-6-(pyridin-4-ylmethyl)-4,5,6,7-tetrahydro-2H-pyrazolo[3,4-c]pyridin-3-ol;
6-(4-(dimethylamino)benzyl)-2-(pyridin-2-yl)-4,5,6,7-tetrahydro-2H-pyrazolo[3,4-c]pyridin-3-ol;
6-(3-(dimethylamino)benzyl)-2-(pyridin-2-yl)-4,5,6,7-tetrahydro-2H-pyrazolo[3,4-c]pyridin-3-ol;
2-(6-aminopyridin-2-yl)-6-benzyl-4,5,6,7-tetrahydro-2H-pyrazolo[3,4-c]pyridin-3-ol;
5-(4-(dimethylamino)benzyl)-2-(pyridin-2-yl)-4,5,6,7-tetrahydro-2H-pyrazolo[4,3-c]pyridin-3-ol;

5-(3-(dimethylamino)benzyl)-2-(pyridin-2-yl)-4,5,6,7-tetrahydro-2H-pyrazolo[4,3-c]pyridin-3-ol;
2-(pyridin-2-yl)-6-(quinolin-6-ylmethyl)-4,5,6,7-tetrahydro-2H-pyrazolo[3,4-c]pyridin-3-ol;
6-(isoquinolin-3-ylmethyl)-2-(pyridin-2-yl)-4,5,6,7-tetrahydro-2H-pyrazolo[3,4-c]pyridin-3-ol;
4-((3-hydroxy-2-(pyridin-2-yl)-2,4,6,7-tetrahydro-5H-pyrazolo[4,3-c]pyridin yl)methyl)benzonitrile;
4-((3-hydroxy-2-(5 (trifluoromethyl)pyridin-2-yl)-2,4,6,7-tetrahydro-5H-pyrazolo[4,3-c]pyridin-5-yl)methyl)benzonitrile;
2-(pyridin-2-yl)-5-(3-(trifluoromethyl)benzyl)-4,5,6,7-tetrahydro-2H-pyrazolo[4,3-c]pyridin-3-ol;
5-(3-(trifluoromethyl)benzyl)-2-(5-(trifluoromethyl)pyridin-2-yl)-4,5,6,7-tetrahydro pyrazolo[4,3-c]pyridin-3-ol;
5-(isoquinolin-3-ylmethyl)-2-(pyridin-2-yl)-4,5,6,7-tetrahydro-2H-pyrazolo[4,3-c]pyridin-3-ol;
5-(isoquinolin-3-ylmethyl)-2-(5-(trifluoromethyl)pyridin-2-yl)-4,5,6,7-tetrahydro-2H-pyrazolo[4,3-c]pyridin-3-ol;
4-(5-benzyl-3-hydroxy-4,5,6,7-tetrahydro-2H-pyrazolo[4,3-c]pyridin-2-yl)benzoic acid.

The compound of the present invention not only effectively reduced the level of ROS generated through stimulation of PMA, TGF-β1, palmitate or high concentration-glucose or the like in all the NHLF (normal human lung fibroblast), LX-2 (human hepatic stellate), ARPE19 (human retinal pigment epithelial), KEL-FIB (keloid fibroblast) cells, but also showed an inhibitory effect of ROS production from 30% to 70% or more when each of the synthetic example compounds of 0.5 uM was treated to differentiated HL-60 (human leukemia cells). Accordingly, the compound of the present invention may be used for prevention or treatment of oxidative stress-related disease.

It has been reported that cancer associated fibroblasts (CAFs) are formed or fibrosis of various tissues is induced, as fibroblasts differentiate into myofibroblasts. As the result of treating the compounds of the present invention into HFF-1, LX-2, NHLF, ARPE19, KEL-FIB cells in which fibrosis is induced by TGF-β1 treatment, an effect of inhibiting expression of αSMA, an indicator of fibrosis. Therefore, the compound of the present invention can be used for prevention or treatment of fibrosis related disease, and can be used for treatment of cancer through regulation of cancer associated fibroblasts, which are important indicators for interaction of tumor microenvironment.

When the ROS level is increased in nerve cells, lipid oxidation is induced, and this is known as an important element in nerve cell death. When treating MPP+ (1-methyl-4-phenylptridinium) inducing ROS and synthetic example compounds to N27 cells (rat dopaminergic neural cells) at the same time, an effect of effectively inhibiting ROS production was shown. Therefore, the compound of the present invention can be used for prevention or treatment of nerve cell death-related disease caused by oxidative stress.

One of main causes of skin fibrotic disease is production of extracellular matrix such as collagen type I, and the like by CTGF from keloid fibroblasts. When the synthetic example compound was treated to KELIB (keloid fibroblast) cells and then TGF-β1 was treated to induce fibrosis, expression of the CTGF gene and collagen type I gene was effectively inhibited. Therefore, the compound of the present invention can be used for prevention or treatment of skin keloid disease.

IL-1β is representative cytokine related to inflammatory disease. When treating the synthetic example compound after treating LPS to LX-2 and NHLF cells, expression of IL-1b was effectively inhibited. Therefore, the compound of the present invention can be used for prevention or treatment of inflammatory disease.

The compound of the present invention not only inhibited expression of αSMA and Collagen I, indicators of pulmonary fibrosis in a pulmonary fibrosis mouse model, but also an effect of improving pulmonary fibrosis such as reducing penetration of inflammatory cells into alveolar and bronchiole was confirmed. In particular, the compound of the present invention showed the result of improving pulmonary fibrosis effectively compared to Nintedanib used as a conventional therapeutic agent of idiopathic pulmonary fibrosis. Therefore, the compound of the present invention can be used for prevention or treatment of fibrotic disease including pulmonary fibrosis.

The compound of the present invention showed the result of improving liver fibrosis and hepatitis symptoms of the STAM mouse in which non-alcoholic steatohepatitis and fibrosis were induced. Therefore, the synthetic example compound of the present invention can be used for prevention or treatment of liver disease including non-alcoholic hepatitis or liver fibrosis.

The compound of the present invention improved behavior disorder symptoms of the Parkinson model mouse, and improved aggregation and accumulation of a-synuclein by 50% or more in brain tissue. Therefore, the compound of the present invention can be used for prevention or treatment of neurodegenerative disease such as Parkinson's disease and the like.

The pharmaceutical composition of the present invention may be for treating oxidative stress-associated disease. The disease may be cancer, inflammatory disease, fibrotic disease, neurodegenerative disease, liver disease, skin disease or retinal disease.

The cancer may be selected from the group consisting of liver cancer, hepatocellular carcinoma, gastrointestinal cancer, stomach cancer, neurofibromatosis-associated meningioma, pancreatic cancer, leukemia, myeloproliferative/myelodysplastic disease, dermal fibrosarcoma, breast cancer, lung cancer, thyroid cancer, colorectal cancer, prostate cancer, breast cancer, ovarian cancer, brain tumor, head and neck cancer, glioblastoma and the like. In addition, the cancer may be a secondary cancer that has metastasized to another organ from the above various types of cancer.

The inflammatory disease may by inflammation-accompanying rheumatic arthritis, osteoarthritis, pneumonia, inflammatory colorectal disease, colitis in the intestine, glomerulonephritis, gastritis, angiitis, pancreatitis, peritonitis, bronchitis, cardiac myositis, encephalitis, inflammation in postischemic reperfusion injury and inflammation resulting from immune rejection after tissue and organ transplantation, various inflammation occurring on skin such as burn, allergic contact dermatitis, and the like, inflammation occurring in multiple organ disorders, diabetic inflammation including diabetic nephropathy, infectious inflammation caused by viral or bacterial infection, or autoimmune disease such as lupus, psoriasis, atherosclerosis, and the like.

The fibrotic disease may be metabolic disorder-induced hepatic fibrosis or hepatocirrhosis, NAFLD-induced fibrosis or hepatocirrhosis, NASH-induced fibrosis or hepatocirrhosis, alcohol-induced hepatic fibrosis or hepatocirrhosis, drug-induced hepatic fibrosis or hepatocirrhosis, infectious agent-induced hepatic fibrosis or hepatocirrhosis, parasite infection-induced hepatic fibrosis or hepatocirrhosis, bacterial infection-induced hepatic fibrosis or hepatocirrhosis, viral infection-induced fibrosis or hepatocirrhosis, HBV-infection-induced hepatic fibrosis or hepatocirrhosis, HCV-infection-induced hepatic fibrosis or hepatocirrhosis, HIV-infection-induced hepatic fibrosis or hepatocirrhosis, double HCV and HIV-infection-induced hepatic fibrosis or hepatocirrhosis, radiation- or chemotherapy-induced fibrosis or hepatocirrhosis, biliary duct fibrosis, hepatic fibrosis or hepatocirrhosis caused by any chronic cholestatic disease, gastrointestinal fibrosis of any etiology, Crohn disease-induced fibrosis, ulcerative colitis-induced fibrosis, intestinal fibrosis, colon fibrosis, stomach fibrosis, lung fibrosis, skin fibrosis, epidermal fibrosis, epithelial fibrosis, skin fibrosis caused by dermatosclerosis/systemic sclerosis, chronic obstructive pulmonary disease (COPD), asthma, pulmonary emphysema, lung of a smoker, tuberculosis, pulmonary fibrosis, lung fibrosis followed by idiopathic pulmonary fibrosis, heart fibrosis, kidney fibrosis, nephrogenic systemic fibrosis, muscular fibrosis, soft tissue fibrosis, bone marrow fibrosis, joint fibrosis, dry fibrosis, cartilage fibrosis, pancreatic fibrosis, uterine fibrosis, nervous fibrosis, testicle fibrosis, ovarian fibrosis, adrenal fibrosis, artery fibrosis, vein fibrosis, eye fibrosis, endomyocardial fibrosis, mediastinal fibrosis, marrow fibrosis, retroperitoneal fibrosis, progressive massive fibrosis which is a complication of pneumoconiosis, proliferative fibrosis, antineoplastic fibrosis, peri-transplant fibrosis, asbestosis, joint fibrosis, or adhesive capsulitis.

The neurodegenerative disease may be Alzheimer's disease (including mild or initial Alzheimer's disease, mild to moderate Alzheimer's disease, moderate to middle Alzheimer's disease, moderate to severe Alzheimer's disease, moderately severe Alzheimer's disease, severe Alzheimer's disease, Alzheimer's disease (AD) with Lewy bodies), Parkinson's disease (including Parkinson's disease chemically induced by exposure to an environmental agent such as a pesticide, insecticide, or herbicide, and/or a metal such as manganese, aluminum, cadmium, copper or zinc, SNCA gene-associated Parkinson's disease, sporadic or idiopathic Parkinson's disease, or Parkinson- or LRRK2-associated Parkinson's disease (PD)), autosomal dominant Parkinson's disease, diffuse Lewy body disease (DLBD) (also known as dementia with Lewy bodies (DLB)), pure autonomic imbalance, Lewy body dysphagia, random LBD, genetic LBD (for example, mutation of alpha-synuclein gene, PARK3 and PARK4), polyphyletic kraurosis (including olivopontocerebellar atrophy, striationigral degeneration, Shy-Drager syndrome (MSA)), disorder or condition characterized by complex Alzheimer and Parkinson's disease and/or MSA, Huntington's disease, synucleinopathy or presence of Lewy bodies, multiple sclerosis, amyotrophic lateral sclerosis (ALS), dementia (including vascular dementia, Lewy body dementia, Parkinson dementia and frontotemporal dementia), psychosis (including anxiety caused by neurodegenerative disease or associated with dopamine therapy, for example, Parkinson's psychosis, Alzheimer's psychosis, Lewy body dementia psychosis (not limited thereto)), dyskinesia (including anxiety caused by neurodegenerative disease or associated with dopamine therapy), anxiety (anxiety caused by neurodegenerative disease or associated with dopamine therapy), condition associated with dopamine therapy (including dysmyotonia, myoclonia or fluttering), synucleinopathy or disease related to abnormal expression of a synuclein.

The liver disease may be metabolic liver disease, non-alcoholic fatty liver disease (NAFLD), non-alcoholic steatohepatitis, drug-induced liver disease, alcohol-induced liver disease, infectious agent-induced liver disease, inflammatory liver disease, immune system dysfunction-mediated liver disease or dyslipidemia.

The skin disease may be keloid disease, psoriasis or leukoplakia, and the retinal disease may be retinal fibrosis, macular degeneration, diabetic retinopathy, cataract or neovascular glaucoma.

The compound of the present invention may be in a form of a pharmaceutically acceptable salt thereof. The salt means a salt commonly used in the medical art to which the present invention belongs, and for example, it may be an inorganic salt prepared by hydrochloric acid, nitric acid, phosphoric acid, bromic acid, iodic acid, perchloric acid, tartaric acid and sulfuric acid, and the like. In addition, it may be an organic acid prepared by acetic acid, prefluoroacetic acid, citric acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, aspartic acid, ascorbic acid, carbonic acid, and the like. Furthermore, it may be sulfonic acid prepared by methane sulfonic acid, ethane sulfonic acid, benzene sulfonic acid, p-toluene sulfonic acid and naphthalene sulfonic acid, and the like, and the type of the salt in the present invention is not limited by these listed salts.

The compound of the present invention may be also in a form of a solvate thereof. "Solvate" means a complex or aggregate formed by one or more solute molecules, that is, the compound of Chemical formula I or a pharmaceutically acceptable salt thereof, and one or more solvent molecules. The solvate may be a complex or aggregate formed with various solvent molecules such as for example, water, methanol, ethanol, isopropanol or acetic acid, or the like.

The compound of the present invention may be also in a form of a stereoisomer thereof. The stereoisomer includes all stereoisomers such as an enantiomer and a diastereomer. The compound may be a stereoisomerically pure form of a stereoisomer, or a mixture of one or more stereoisomers, for example, a racemic mixture. Separation of a specific stereoisomer may be performed by one of common methods known in the art. Some examples of the compound of the present invention may have a greater inhibitory effect of oxidative stress of a specific stereoisomer compared to racemic mixture thereof. In this case, by using a specific stereoisomer, a dosage can be reduced. Therefore, by separating a specific stereoisomer, for example, an enantiomer and a diastereomer, with a great inhibitory effect of oxidative stress, oxidative stress-related disease can be efficiently treated.

Other aspect of the present invention provides a pharmaceutical composition comprising a therapeutically effective dose of the compound of Chemical formula I defined above, or a pharmaceutically acceptable salt or solvate or stereoisomer thereof and a pharmaceutically acceptable carrier.

In the composition of the present invention, the compound, or pharmaceutically acceptable salt or solvate or stereoisomer thereof is as defined above.

In the composition of the present invention, "pharmaceutically acceptable carrier" represents a substance, generally, inactive substance, used in combination with an active ingredient to help application of the active ingredient. The carrier includes common pharmaceutically acceptable excipients, additives or diluents. The carrier may comprise one or more selected from for example, fillers, binders, disintegrants, buffers, preservatives, anti-oxidants, glydents, flavoring agents, thickeners, coloring agents, emulsifiers, suspending agents, stabilizers, pH adjusting agents and tonicifying agents.

As the diluent, sugar, starch, microcrystalline cellulose, lactose (lactose hydrate), glucose, di-mannitol, alginate, alkali earth metal salts, clay, polyethylene glycol, anhydrous calcium hydrogen phosphate or a mixture thereof, or the like; and as the binder, starch, microcrystalline cellulose, highly dispersible silica, mannitol, di-mannitol, sucrose, lactose hydrate, polyethylene glycol, polyvinyl pyrrolidone (povidone), polyvinyl pyrrolidone copolymer (copovidone), hypromellose, hydroxypropylcellulose, natural gum, synthetic gum, gelatin or a mixture thereof, or the like may be used.

As the disintegrant, starch or modified starch such as sodium starch glyconic acid, corn starch, potato starch, pregelatinized starch, and the like; clay such as bentonite, montmorillonite or veegum, or the like; celluloses such as microcrystalline cellulose, hydroxypropylcellulose or carboxylmethylcellulose, or the like; algines such as sodium alginate or alginic acid, or the like; cross-linked celluloses such as sodium croscarmellose, or the like; gums such as guar gum, xanthan gum, or the like; cross-linked polymers such as cross-linked polyvinylpyrrolidone (crospovidone), or the like; ebllient agents such as sodium bicarbonate, citric acid, or the like, or a mixture thereof may be used.

As the lubricant, talc, stearic acid, magnesium stearate, calcium stearate, sodium lauryl sulfate, hydrogenated vegetable oil, sodium benzoate, sodium stearylfumarate, glyceryl monorate, glyceryl monostearate, glyceryl palmitostearate, colloidal silicon dioxide or a mixture thereof, or the like may be used.

As the pH adjusting agent, an acidifier such as acetic acid, ascorbic acid, sodium ascorbate, sodium etheric acid, malic acid, succinic acid, tartaric acid, fumaric acid and citric acid, and a basifier such as precipitated calcium carbonate, ammonia water, meglumine, sodium carbonate, magnesium oxide, magnesium carbonate, sodium citrate and tribasic calcium phosphate, and the like may be used.

As the anti-oxidant, dibutylhydroxy toluene, butylated hydroxyanisol, tocopherol acetate, tocopherol, propyl galate, sodium bisulfite, sodium pyrosulfite, and the like may be used. In the pre-release compartment, as the solubilizer, polyoxyethylene sorbitan fatty acid esters such as sodium lauryl sulfate, polysorbate, and the like, sodium docusate, poloxamer, and the like may be used.

In addition, in order to make a sustained release agent, it may comprise an enteric polymer, a water-insoluble polymer, a hydrophobic compound and a hydrophilic polymer.

The enteric polymer refers to a polymer dissolved or degraded under a specific pH condition of pH 5 or more, which is insoluble or stable under an acidic condition of less than pH 5, and for example, it includes enteric cellulose derivatives such as hypromellose acetate succinate, hypromellose phthalate (hydroxypropylmethylcellulose phthalate), hydroxymethylethylcellulose phthalate, cellulose acetate phthalate, cellulose acetate succinate, cellulose acetate malate, cellulose benzoate phthalate, cellulose propionate phthalate, methylcellulose phthalate, carboxymethylethylcellulose and ethylhydroxyethylcellulose phthalate and methylhydroxyethylcellulose; the enteric acrylate-based copolymers such as styrene-acrylate copolymer, acrylatemethyl-acrylate copolymer, acrylatemethylmethacrylate copolymer (for example, acryl-is), acrylatebutyl-styrene-acrylate copolymer and acrylatemethyl-methacrylate-acrylateoctyl copolymer; enteric polymethacrylate copolymers such as poly(methacrylate methyl methacrylate) copolymer (for example, Eudragit L, Eudragit S, Evonik, Germany), and poly(methacrylate ethylacrylate) copolymer (for example, Eudragit L100-55); enteric maleate-based copolymers such as acetatevinyl-maleate anhydride copolymer, styrene-maleate anhydride copolymer, styrene-maleate monoesterol copolymer, vinylmethylether-maleate anhydride copolymer, ethylene-maleate anhydride copolymer, vinylbutylether-maleate anhydride copolymer, acrylonitrile-acrylatemethyl maleate anhydride copolymer and acrylatebutyl-styrene-maleate anhydride copolymer; and enteric polyvinyl derivatives such as polyvinylalcoholphthalate, polyvinylacetalphthalate, polyvinylbutylatephthalate and polyvinylacetacetalphthalate.

The water-insoluble polymer refers to a pharmaceutically acceptable polymer undissolved in water, which controls release of a drug. For example, the water-insoluble polymer includes polyvinylacetate (for example, Kollicoat SR30D), water-insoluble polymethacrylate copolymer [for example, poly(ethylacrylate-methyl methacrylate) copolymer (for example, Eudragit NE30D, poly(ethylacrylate-methyl methacrylate-trimethylaminoethyl methacrylate) copolymer (for example, Eudragit RSPO), etc.), ethylcellulose, cellulose ester, cellulose ether, cellulose acylate, cellulose diacylate, cellulose triacylate, cellulose acetate, cellulose diacetate and cellulose triacetate and the like.

The hydrophobic compound refers to a pharmaceutically acceptable substance undissolved in water, which controls release of a drug. For example, it includes fatty acids and fatty acid esters such as glyceryl palmitostearate, glyceryl stearate, glyceryl behenate, cetyl palmitate, glyceryl monoolate, and stearic acid; wax such as carnauba wax, cera and microcrystalline wax; and mineral substances such as talc, precipitated calcium carbonate, calcium monohydrogen phosphate, zinc oxide, titanium oxide, kaolin, bentonite, montmorillonite and veegum, and the like.

The hydrophilic polymer refers to a pharmaceutically acceptable substance dissolved in water, which controls release of a drug. For example, it includes saccharides such as dextrin, polydextrin, dextran, pectin and pectin derivatives, alginate salts, polygalacturonic acid, xylan, arabinoxylan, arabinogalactan, starch, hydroxypropylstarch, amylose and amylopectin; cellulose derivatives such as hypromellose, hydroxypropylcellulose, hydroxymethylcellulose, hydroxyethylcellulose, methylcellulose and sodium carboxymethylcellulose; gums such as guar gum, locust bean gum, *tragacantha*, carrageenan, acacia gum, arabia gum, gellan gum and xanthan gum; proteins such as gelatin, casein and zein; polyvinyl derivatives such as polyvinyl alcohol, polyvinyl pyrrolidone and polyvinylacetaldiethylaminoacetate; hydrophilic polymethacrylate copolymers such as poly(butyl methacrylate-(2-dimethylaminoethyl) methacrylate-methylmethacrylate) copolymer (for example, Eudragit E100, Evonik, Germany), poly(ethyl acrylate-methyl methacrylate-triethylaminoethyl-methacrylate chloride) copolymer (for example, Eudragit RL, RS, Evonik, Germany); polyethylene derivatives such as polyethylene glycol and polyethylene oxide; and carbomers and the like.

In addition, the preparation of the present invention may be formulated by selectively using pharmaceutically acceptable additives as various additives selected from coloring agents and flavoring agents.

In the present description, the scope of the additive is not limited as using the above additives, and it may be formulated by containing a dose within a common range by selection of the above additives.

The pharmaceutical composition according to the present invention may be used as formulated in a form of an oral formulation such as powder, granules, tablets, capsules, suspension, emulsion, syrup and aerosol and the like, an external application, a suppository or a sterilized injection solution according to a common method.

The composition of the present invention may be orally administered, or parenterally administered including intravenous, intraperitoneal, subcutaneous, intrarectal and local administration.

Other aspect of the present invention provides a method for treating disease in a subject, comprising administering a therapeutically effective dose of the compound of Chemical formula I, or pharmaceutically acceptable salt or solvate or stereoisomer thereof into a subject.

In the method, those skilled in the art may appropriately select the administration route upon administration according to the patient's condition. The administration may be oral or parenteral. The parenteral administration includes intravenous, intraperitoneal, subcutaneous, intrarectal and local administration.

In the method, the dosage may be variously modified according to various factors such as patient's condition, administration route, family doctor's judgement and the like as mentioned above. An effective dosage may be estimated from a dose-response curve obtained from an in vitro experiment or animal model test. The ratio and concentration of the compound of the present invention present in the composition to be administered may be determined depending on the chemical property, administration route, therapeutic dose, and the like. The dosage may be administered in an effective dose of about 1 μg/kg to about 1 g/kg/day, or about 0.1 mg/kg to about 500 mg/kg/day into a subject. The dose may be modified according to the age, body weight, sensitivity or symptoms of the subject.

Furthermore, the pharmaceutical composition comprising the compound or solvate, stereoisomer or pharmaceutically acceptable salt thereof of the present invention may be used for a method for prevention or treatment of disease selected from cancer, keloidosis, hepatic fibrosis, hepatic cirrhosis, pulmonary fibrosis, Parkinson's disease, Huntington's disease, amyotrophic lateral sclerosis, multiple sclerosis, ischemic or traumatic brain injury, retinal fibrosis, macular degeneration, and inflammatory disease, comprising administering it into a subject in need thereof.

MODE FOR INVENTION

Hereinafter, the present invention will be described in more detail by examples. These examples are intended to illustrate the present invention more specifically, and it is obvious to those skilled in the art that the scope of the present invention is not limited by these examples according to the gist of the present invention.

The compound represented by Chemical formula I of the present invention may be prepared by the method exemplified in the following reaction formulas, but not limited thereto.

General Synthesis Process 1 (Synthetic Examples 1~4)

Synthetic examples 1 to 4 were synthesized by the following method, and specific synthetic examples were described.

2-Hydrazinopyridine derivative (100 mmol) and beta-keto ester (100 mmol) dissolved in ethanol (30~50 mL) are filled in a 100 mL round bottom flask and it is heated to 140° C. for 24 hours. Then, ethanol is slowly distilled off under atmospheric pressure for about 3 hours. The progress level of the reaction and consumption of the intermediate (hydrazinimine) are monitored by LCMS. The product is dissolved in hot ethanol, cooled and purified by recrystallization to obtain a white solid (yield 40~70%).

Synthetic Example 1. 2-(Pyridin-2-yl)-4,5,6,7-tetrahydro-2H-indazol-3-ol

1H-NMR (600 MHz, CDCL3) δ 8.23-8.55 (m, 1H), 7.71-8.04 (m, 2H), 7.10 (m, 1H), 2.44-1.95-2.77 (m, 4H), 1.50-1.80 (m, 3H), 1.07(2d, 2H), Mass$[M+H]^+$: 216.0, conformational isomer mixture.

Synthetic Example 2. 2-(5-(Tritluoromethyl)pyridin-2-yl)-4,5,6,7-tetrahydro-2H-indazol-3-ol 1H-NMR (600 MHz, CDCL3) δ 11.80(s, 0.5H), 8.81(s, 0.5H), 8.67(d, J=9.0 Hz, 0.5H), 8.53 (d, J=11.0 Hz, 1H), 8.02(dd, J=9.0, 2.1 Hz, 0.5H), 7.94-7.96 (m, 1H), 2.59-2.65 (dt, J=64.0, 6.2 Hz, 2H), 2.35-2.45(dt, J=59.0, 6.0 Hz, 2H), 1.72-1.87 (m, 4H), Mass$[M+H]^+$: 284.0, conformational isomer mixture.

Synthetic Example 3. 6-Benzyl-2-(pyridin-2-yl)-4,5,6,7-tetrahydro-2H-pyrazole[3,4-c]pyridin-3-ol 1H-NMR (400 MHz, DMSO-$d_6$,) δ 11.75 (s, 1H), 8.39 (s, 1H), 7.94 (s, 1H), 7.65 (s, 2H), 7.45 (s, 3H), 7.35~7.15 (m, 2H), 4.42(bs, 2H), 4.11(bs, 2H), 3.56(bs, 1H), 3.21(bs, 1H), 2.8~2.6(m, 2H), Mass$[M+H]^+$; 307.1; HPLC retention time: 3.4 min, $\lambda_{max}$: 304 nm, purity 97.8%.

Synthetic Example 4. 6-Benzyl-2-(5-(trifluoromethyl)pyridin-2-yl)-4,5,6,7-tetrahydro-2H-pyrazolo[3,4-c]pyridin-3-ol 1H-NMR (600 MHz, CDCL3) δ 8.52 (s, 1H), 8.00 (s, 2H), 7.20-7.37 (m, 5H), 3.72 (d, J=11.0 Hz, 2H), 3.53 (s, 2H), 2.74(bs, 2H), 2.56(bs, 2H), Mass$[M+H]^+$: 375.2.

General Synthesis Process 2 (Alkyl Derivatives Among Synthetic Examples)

The general synthesis process of alkyl derivatives among Synthetic examples is as follows.

Step 1 Reaction

A mixture of ethyl 1-benzyl-3-oxopiperidine-4-carboxylate (1.0 g, 3.35 mmol), ZnCl(0.46 g, 3.36 mmol) and $NaBH_4$(0.13 g, 3.36 mmol) was dissolved in methanol (20 mL) and stirred at 70° C. overnight. The solvent was removed under reduced pressure and the residues were diluted with water (50 mL). The water layer was extracted with ethylacetate (3×50 mL). The combined organic layers were washed with salt water (50 mL) and dried over anhydrous $Na_2SO_4$, and concentrated to obtain the desired product as pale yellow oil.

Step 2 Reaction

A mixture of ethyl 1-benzyl-3-hydroxypiperidine-4-carboxylate (0.5 g, 2.01 mmol) and Pd/C(10%, 50 mg) in methanol (20 mL) solvent was stirred under hydrogen gas balloon pressure at a room temperature overnight. The solvent was removed under reduced pressure to obtain the desired product as pale yellow oil.

Step 3 Reaction

Secondary amine (0.5 g, 1 mol equivalent), N,N-diisopropyl ethylamine (1.5 mol equivalents), alkyl halide (1.1 mol equivalents) and 10 mL DMF were added in a round bottom flask and stirred at a room temperature under nitrogen. After completing the reaction (monitoring by TLC), the reaction mixture was evaporated and dried under reduced pressure. The residues were dissolved in 5 mL methylene chloride and washed with 5 mL distilled water. The aqueous layer was washed with 3×5 mL portions of methylene chloride. The collected organic portions were dried with $MgSO_4$ and filtered and then the solvent was removed under reduced pressure to obtain the product.

Step 4 Reaction

To 40 mL acetonitrile, $H_5IO_6$ (1.19 g, 5.15 mmol) was added and intensively stirred at a room temperature for 15 minutes. In succession, after adding an alcohol intermediate (under ice cooling), PCC dissolved in 10 mL acetonitrile was added twice and stirred for 2 hours. Then, the reaction mixture was diluted with 100 mL ethylacetate and it was washed with 1:1 salt water:water, saturated aqueous $Na_2SO_3$ solution and salt water, respectively, and dried on anhydrous $Na_2SO_4$, and concentrated to obtain the product.

Step 5 Reaction

2-Hydrazinopyridine derivative (1.1 mol equivalents) and beta-keto ester (1 mol equivalent) dissolved in ethanol (0.5~5 mL) were filled to a 10 mL round bottom flask and heated to 140° C. for 12 hours. After starting the reaction, ethanol was distilled off under atmospheric pressure for 3 hours. The product was purified on silica gel (yield 5~30%).

General Synthetic Process 3 (Synthetic Examples 5 to 33, 35 to 38, 43, 44, 53 to 58, 65 to 70, 73, 74)

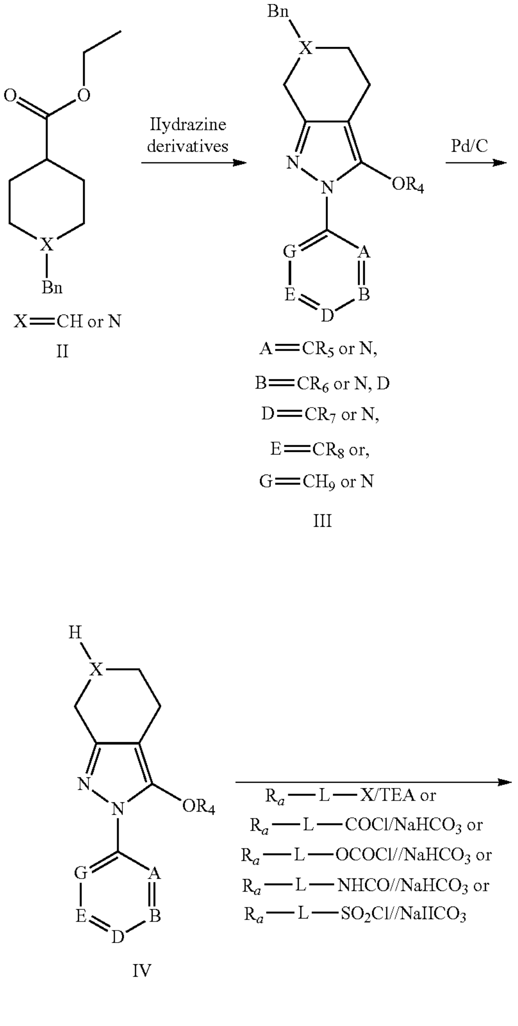

X═CH or N

II

A═$CR_5$ or N,

B═$CR_6$ or N, D

D═$CR_7$ or N,

E═$CR_8$ or,

G═$CH_9$ or N

III

IV

-continued

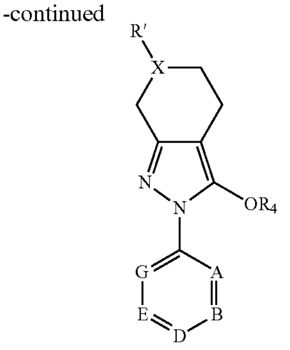

R′═$R_a$—L—, $R_a$—L—OCO, $R_a$—L—NHCO, $R_a$—L—$SO_2$

V

Synthetic examples 5 to 33, 35 to 38, 43, 44, 53 to 58, 65 to 70, 73, 74 are synthesized according to the above general reaction formula, and an example of the synthesis method which applies a specific compound is as below.

Step 1 Reaction

2-Hydrazinopyridine derivative (2 g, 1.1 mol equivalent) and beta-keto ester (5 g, 1 mol equivalent) dissolved in ethanol (40 mL) are filled in a 100 mL round bottom flask and it is heated to 140° C. for 24 hours. Then, after starting the reaction, ethanol is slowly distilled off under atmospheric pressure for about 3 hours. The progress level of the reaction and consumption of the intermediate (hydrazin-imine) are monitored by LCMS. The product is dissolved in hot ethanol (50 mL), cooled and purified by recrystallization to obtain a white solid (yield 3.7 g, 85%).

Step 2 Reaction

6-Benzyl-2-(pyridin-2-yl)-4,5,6,7-tetrahydro-2H-pyrazolo[3,4-c]pyridin-3-ol hydrochloride (0.5 g, 2.01 mmol) was dissolved in methanol (20 mL) and Pd/C (containing moisture, 10%, 250 mg) was stirred under hydrogen gas balloon pressure at a room temperature for 2 days. The solvent was removed under reduced pressure to obtain the product of pale yellow solid hydrochloride.

Step 3-1 Reaction (Alkyl Derivatives)

2-(Pyridin-2-yl)-4,5,6,7-tetrahydro-2H-pyrazolo[3,4-c]pyridin-3-ol (50 mg, 0.12 mmol) was dissolved in 5 mL dimethylacetamide. To the reaction solution, triethylamine (97 uL, 3 equivalents) and alkyl halide (1.2 equivalents) were added at a room temperature. The reaction mixture solution was stirred at a room temperature for 2 hours. It was diluted with ethylacetate (50 mL) and salt water/$NaHCO_3$ saturated aqueous solution was mixed to use for washing. The product was purified by recrystallization and the yield was in a range of 10~50%.

Step 3-2 Reaction (Amide, Carbonate, Urea, Sulfonamide Derivative Synthesis Method)

2-(Pyridin-2-yl)-4,5,6,7-tetrahydro-2H-pyrazolo[3,4-c]pyridin-3-ol (20 mg, 0.08 mmol) was dissolved in a mixed solution of 5 mL acetonitrile and 1 mL water, and $NaHCO_3$ saturated solution (200 uL) was added. For synthesis of each derivative, one of carboxyl chloride, chloroformate, isocyanate and sulfonyl chloride was selected and added at a room temperature. The reaction mixture solution was stirred at a room temperature for 1 hour and the completion of the reaction was confirmed by LC-MS, and then ethyl acetate 50 mL was added to dilute and it was washed with salt water and $NaHCO_3$ mixed saturated solution. The product was separated and purified by TLC and the yield was in a range of 10~70%, Furthermore, the data of the synthetic examples prepared according to the general synthesis method and the synthesis method using a specific substance were described.

Synthetic Example 5. 2-(Pyridin-2-yl)-4,5,6,7-tetrahydro-2H-pyrazolo[3,4-c]pyridin-3-ol 1H-NMR (600 MHz, DMSO-D6) δ 9.74(bs, 1H), 8.45 (d, J=4.8 Hz, 1H), 8.05-7.92(1H), 7.37-7.24(1H), 4.14 (s, 2H), 3.31 (t, J=5.9 Hz, 2H), 2.50 (s, 2H), Mass[M+H]$^+$: 217.0.

Synthetic Example 6. 6-(4-Fluorobenzyl)-2-(pyridin-2-yl)-4,5,6,7-tetrahydro-2H-pyrazolo[3,4-c]pyridin-3-ol 1H-NMR (600 MHz, CDCl3) δ 8.24 (d, J=4.8 Hz, 1H), 7.80 (m, 2H), 7.35 (dd, J=8.3, 5.5 Hz, 2H), 7.00-7.12 (m, 3H), 3.68 (d, J=4.8 Hz, 2H), 3.54 (s, 2H), 2.74 (t, J=5.9 Hz, 2H), 2.58 (t, J=5.9 Hz, 2H), Mass[M+H]$^+$: 325.0.

Synthetic Example 7. 6-(4-Methylbenzyl)-2-(pyridin-2-yl)-4,5,6,7-tetrahydro-2H-pyrazolo[3,4-c]pyridin-3-ol 1H-NMR (600 MHz, CDCl3) δ 8.23 (m, 1H), 7.80 (m, 2H), 7.00-7.12 (m, 5H), 3.68 (s, 2H), 3.54 (s, 2H), 2.72 (m, 2H), 2.56 (m, 2H), 2.34 (s, 3H), Mass[M+H]$^+$: 321.0.

Synthetic Example 8. 4-((3-Hydroxy-2-(pyridin-2-yl)-2,4,5,7-tetrahydro-6H-pyrazolo[3,4-c]pyridin-6-yl)methyl)benzonitrile 1H-NMR (600 MHz, CDCl3) δ 8.25 (d, J=4.8 Hz, 1H), 7.81 (m, 2H), 7.64 (m, 3H), 7.52 (d, J=7.6 Hz, 2H), 3.77 (d, J=4.8 Hz, 2H), 3.55 (s, 2H), 2.74-2.78 (m, 2H), 2.59 (t, J=5.9 Hz, 2H), Mass[M+H]$^+$: 332.0.

Synthetic Example 9. 6-(3,5-Difluorobenzyl)-2-(pyridin-2-yl)-4,5,6,7-tetrahydro-2H-pyrazolo[3,4-c]pyridin-3-ol 1H-NMR (600 MHz, CDCl3) δ 8.22(d, J=4.8 Hz, 1H), 7.79 (t, J=7.9 Hz, 2H), 7.09 (s, 1H), 6.92 (d, J=6.2 Hz, 1H), 6.67-6.69 (m, 2H), 3.67 (s, 3H), 3.53 (s, 2H), 2.73 (m, 2H), 2.57 (t, J=5.5 Hz, 2H), Mass[M+H]$^+$: 343.0.

Synthetic Example 10. 2-(Pyridin-2-yl)-6-(3-(trifluoromethyl)benzyl)-4,5,6,7-tetrahydro-2H-pyrazolo[3,4-c]pyridin-3-ol 1H-NMR (600 MHz, CDCl3) δ 8.24 (d, J=4.8 Hz, 1H), 7.80 (m, 2H), 7.35 (m, 2H), 7.00-7.12 (m, 3H), 3.68 (d, J=4.8 Hz, 2H), 3.54 (s, 2H), 2.74 (t, J=5.9 Hz, 2H), 2.58 (t, J=5.9 Hz, 2H), Mass[M+H]$^+$: 374.9.

Synthetic Example 11. 6-(Naphthalene-2-ylmethyl)-2-(pyridin-2-yl)-4,5,6,7-tetrahydro-2H-pyrazolo[3,4-c]pyridin-3-ol 1H-NMR (600 MHz, CDCl3) δ 8.56 (s, 1H), 7.77-7.88 (m, 6H), 7.43-7.47 (m, 3H), 7.18 (m, 1H), 3.92 (s, 2H), 3.73 (s, 2H), 3.01 (t, J=5.9 Hz, 2H), 2.80 (m, 2H), Mass[M+H]$^+$: 356.9.

Synthetic Example 12. 1-(4,5-Dihydro-3-hydroxy-2-(pyridin-2-yl)-2H-pyrazolo[3,4-c]pyridin-6(7H)-yl)butan-1-one 1H-NMR (600 MHz, CDCL3) δ 8.27(q, J=5.3 Hz, 1H), 7.81-7.89 (m, 2H), 7.13-7.17 (m, 1H), 4.65(ss, 2H), 3.76 (rotational isomer mixture dt, J=5.7 Hz, 2H), 2.58(dt, J=29.4, 5.9 Hz, 2H), 2.41 (m, 2H), 1.64-1.74 (m, 2H), 0.96-1.01 (m, 3H), Mass[M+H]$^+$: 286.9.

Synthetic Example 13. 1-(3-Hydroxy-2-(pyridin-2-yl)-2,4,5,7-tetrahydro-6H-pyrazolo[3,4-c]pyridin-6-yl)ethan-1-one 1H-NMR (600 MHz, CDCl3) δ 8.27(q, J=5.7 Hz, 1H), 7.82-7.90 (m, 2H), 7.14-7.18 (m, 1H), 4.64(2s, 2H), 3.74(2t, J=5.9 Hz, 2H), 2.59(2t, J=6.0 Hz, 2H), 2.18-2.20(2s, 3H), Mass[M+H]$^+$: 258.1: conformational isomer mixture.

Synthetic Example 14. 6-(4-Methoxybenzyl)-2-(pyridin-2-yl)-4,5,6,7-tetrahydro-2H-pyrazolo[3,4-c]pyridin-3-ol 1H-NMR (600 MHz, CDCl3) δ 8.24 (d, J=4.8 Hz, 1H), 7.81(bs, 2H), 7.29 (d, J=8.3 Hz, 2H), 7.10 (m, 1H), 6.86 (d, J=8.6 Hz, 2H), 3.80 (s, 3H), 3.67 (s, 2H), 3.55 (s, 2H), 2.74 (t, J=5.9 Hz, 2H), 2.57 (t, J=5.9 Hz, 2H), Mass[M+H]$^+$: 337.0.

Synthetic Example 15. 6-Ethyl-2-(pyridin-2-yl)-4,5,6,7-tetrahydro-2H-pyrazolo[3,4-c]pyridin-3-ol 1H-NMR (600 MHz, DMSO-D6) δ 8.34(bs, 1H), 7.85-7.96 (m, 2H), 7.26-7.28(bs, 1H), 4.31(2bs, 2H), 3.60(bs, 2H), 3.22(q, J=7.3 Hz, 1H), 2.86-2.96 (m, 2H), 1.47-1.56 (m, 3H), Mass[M+H]$^+$: 244.9.

Synthetic Example 16. 6-(Prop-2-yn-1-yl)-2-(pyridin-2-yl)-4,5,6,7-tetrahydro-2H-pyrazolo[3,4-c]pyridin-3-ol 1H-NMR (600 MHz, CDCl3) δ 8.25(bd, J=4.8 Hz, 1H), 7.84(bs, 2H), 7.12 (dd, J=8.3, 5.5 Hz, 1H), 3.72 (s, 2H), 3.55 (d, J=2.1 Hz, 2H), 2.83 (t, J=5.9 Hz, 2H), 2.63 (t, J=5.5 Hz, 2H), 2.30 (t, J=2.4 Hz, 1H), Mass[M+H]$^+$: 254.9.

Synthetic Example 17. 6-Propyl-2-(pyridin-2-yl)-4,5,6,7-tetrahydro-2H-pyrazolo[3,4-c]pyridin-3-ol 1H-NMR (600 MHz, DMSO-D6) δ 8.24(s, 1H), 7.79(b, 2H), 7.16(s, 1H), 4.16(b, 2H), 3.33-3.48 (m, 2H), 3.13(bs, 2H), 2.77-2.92 (m, 2H), 1.7-2.0(m, 5H), Mass[M+H]$^+$: 258.9.

Synthetic Example 18. 6-Allyl-2-(pyridin-2-yl)-4,5,6,7-tetrahydro-2H-pyrazolo[3,4-c]pyridin-3-ol 1H-NMR (600 MHz, CDCL3) δ 8.24(bs, 1H), 7.82 b(s, 2H), 7.11(bs, 2H), 5.19-5.27 (m, 3H), 3.72(bs, 2H), 3.22 (d, J=6.2 Hz, 3H), 2.75(bs, 2H), 2.59(bs, 2H), Mass[M+H]$^+$: 257.0.

Synthetic Example 19. (3-Hydroxy-2-(pyridin-2-yl)-2,4,5,7-tetrahydro-6H-pyrazolo[3,4-c]pyridin-6-yl)(phenyl)methanone 1H-NMR (600 MHz, CDCl3) δ 8.19-8.20 (m, 1H), 7.66-7.85 (m, 2H), 7.39-7.49 (m, 5H), 7.11(broad, 1H), 4.76 (m, 2H), 3.58-4.13 (m, 2H), 2.59-2.76 (m, 2H), Mass[M+H]$^+$: 320.9: conformational isomer mixture.

Synthetic Example 20. Benzyl 3-hydroxy-2-(pyridin-2-yl)-2,4,5,7-tetrahydro-6H-pyrazolo[3,4-c]pyridin-6-carboxylate 1H-NMR (600 MHz, CDCl3) δ 8.24 (d, J=4.8 Hz, 1H), 7.80-7.85 (m, 2H), 7.34 (m, 5H), 7.13 (t, J=6.5 Hz, 1H), 5.16 (s, 2H), 4.61 (s, 2H), 3.72(bs, 2H), 2.57(bs, 2H), Mass[M+H]$^+$: 350.9.

Synthetic Example 21. (4-Chlorophenyl)(3-hydroxy-2-(pyridin-2-yl)-2,4,5,7-tetrahydro-6H-pyrazolo[3,4-c]pyridin-5-yl)methanone 1H-NMR (600 MHz, CDCl3) δ 8.13 (d, J=8.3 Hz, 1H), 7.71-7.86 (m, 2H), 7.41-7.44 (m, 4H), 7.09-7.15 (m, 1H), 4.54-4.92 (m, 2H), 3.59-4.01 (m, 2H), 2.64 (m, 2H), Mass [M+H]$^+$: 354.9, conformational isomer mixture.

Synthetic Example 22. Ethyl 3-hydroxy-2-(pyridin-2-yl)-2,4,5,7-tetrahydro-6H-pyrazolo[3,4-c]pyridin-6-carboxylate 1H-NMR (600 MHz, CDCL3) δ 8.24-8.39 (m, 1H), 7.70-7.86 (m, 2H), 7.12-7.18 (m, 1H), 4.58-4.80 (m, 2H), 4.17-4.23 (m, 2H), 3.67 (m, 2H), 2.44-2.60 (m, 2H), 1.21-1.30 (m, 3H), Mass[M+H]$^+$: 288.9, conformational isomer mixture.

Synthetic Example 23. N-cyclohexyl-3-hydroxy-2-(pyridin-2-yl)-2,4,5,7-tetrahydro-6H-pyrazolo[3,4-c]pyridin-6-carboxamide 1H-NMR (600 MHz, CDCL3) δ 8.28 (d, J=4.8 Hz, 1H), 7.84-7.89 (m, 2H), 7.17 (t, J=6.2 Hz, 1H), 4.49 (s, 2H), 3.67-3.71 (m, 1H), 3.65 (t, J=5.5 Hz, 2H), 2.59 (t, J=5.9 Hz, 2H), 1.35-1.99 (m, 10H), Mass[M+H]$^+$: 341.9

Synthetic Example 24. Furan-2-yl(3-hydroxy-2-(pyridin-2-yl)-2,4,5,7-tetrahydro-6H-pyrazolo[3,4-c]pyridin-6-yl)methanone 1H-NMR (600 MHz, CDCl3) δ 8.31 (d, J=5.2 Hz, 1H), 7.90 (m, 2H), 7.56 (s, 1H), 7.19 (t, J=6.5 Hz, 1H), 7.10 (s, 1H), 6.54 (s, 1H), 5.08-4.76 (m, 2H), 4.00 (m, 2H), 2.76(bs, 2H), Mass[M+H]$^+$: 310.9.

Synthetic Example 25. 6-(Methylsulfonyl)-2-(pyridin-2-yl)-4,5,6,7-tetrahydro-2H-pyrazolo[3,4-c]pyridin-3-ol 1H-NMR (600 MHz, CDCl3) δ 8.28(d, J=4.8 Hz, 1H), 7.83-7.90 (m, 2H), 7.18 (t, J=6.2 Hz, 1H), 4.45 (s, 2H), 3.59-3.62 (m, 2H), 3.38 (s, 2H), 3.11 (s, 3H), Mass[M+H]$^+$: 294.8.

Synthetic Example 26. 6-(phenylsulfonyl)-2-(pyridin-2-yl)-4,5,6,7-tetrahydro-2H-pyrazolo[3,4-c]pyridin-3-ol 1H-NMR (600 MHz, CDCL3) δ 8.25 (d, J=4.8 Hz, 1H), 7.83-7.85 (m, 2H), 7.51-7.60 (m, 5H), 7.15 (t, J=6.2 Hz, 1H), 4.26 (s, 2H), 3.39 (t, J=5.9 Hz, 2H), 2.60 (t, J=5.9 Hz, 2H), Mass[M+H]$^+$: 356.9.

Synthetic Example 27. N-(4-fluorophenyl)-3-hydroxy-2-(pyridin-2-yl)-2,4,5,7-tetrahydro-6H-pyrazolo[3,4-c]pyridin-6-carboxamide 1H-NMR (600 MHz, CDCL3) δ 8.26 (d, J=5.5 Hz, 1H), 7.82-7.87 (m, 2H), 7.29-7.31 (m, 2H), 7.15 (t, J=6.5 Hz, 1H), 6.97 (t, J=9.0 Hz, 2H), 6.56(bs, 1H), 4.60 (s, 2H), 3.72 (t, J=5.9 Hz, 2H), 2.63 (t, J=5.9 Hz, 2H), Mass[M+H]$^+$: 353.9.

Synthetic Example 28. N-(4-fluorobenzyl)-3-hydroxy-2-(pyridin-2-yl)-2,4,5,7-tetrahydro-6H-pyrazolo[3,4-c]pyridin-6-carboxamide 1H-NMR (600 MHz, CDCL3) δ 8.26 (d, J=4.8 Hz, 1H), 7.78-7.86 (m, 2H), 7.26 (dd, J=8.6, 5.9 Hz, 2H), 7.14 (t, J=6.2 Hz, 1H), 6.99 (t, J=8.6 Hz, 2H), 4.49 (s, 2H), 4.38 (d, J=5.5 Hz, 2H), 3.63 (t, J=5.5 Hz, 2H), 2.56 (t, J=5.2 Hz, 2H), Mass[M+H]$^+$: 367.9.

Synthetic Example 29. N-(furan-2-ylmethyl)-3-hydroxy-2-(pyridin-2-yl)-2,4,5,7-tetrahydro-6H-pyrazolo[3,4-c]pyridin-6-carboxamide 1H-NMR (600 MHz, CDCL3) δ 8.26 (d, J=4.8 Hz, 1H), 7.79-7.86 (m, 2H), 7.35 (s, 1H), 7.14 (t, J=6.2 Hz, 1H), 6.31 (t, J=2.4 Hz, 1H), 6.23 (d, J=3.4 Hz, 1H), 4.49 (s, 2H), 4.43 (d, J=5.5 Hz, 2H), 3.62-3.65 (m, 2H), 2.56 (m, 2H), Mass [M+H]$^+$: 339.9.

Synthetic Example 30. N-(4-chlorophenethyl)-3-hydroxy-2-(pyridin-2-yl)-2,4,5,7-tetrahydro-6H-pyrazolo[3,4-c]pyridin-6-carboxamide 1H-NMR (600 MHz, CDCl3) δ 8.26(bs, 1H), 7.83 (d, J=30.3 Hz, 2H), 7.25-7.27 (m, 2H), 7.07-7.15 (m, 3H), 4.42 (s, 2H), 3.58 (s, 2H), 3.47 (m, 2H), 2.77-2.81 (m, 2H), 2.54 (s, 2H), Mass[M+H]$^+$: 397.9.

Synthetic Example 31. 6-(Naphthalene-2-ylsulfonyl)-2-(pyridin-2-yl)-4,5,6,7-tetrahydro-2H-pyrazolo[3,4-c]pyridin-3-ol 1H-NMR (600 MHz, CDCl3) δ 8.38 (s, 1H), 7.94 (d, J=6.9 Hz, 2H), 7.52-7.60 (m, 7H), 7.11(bs, 1H), 4.29 (s, 2H), 3.54 (m, 2H), 2.57(bs, 2H), Mass[M+H]$^+$: 406.8.

Synthetic Example 32. 4-Nitrobenzyl 3-hydroxy-2-(pyridin-2-yl)-2,4,5,7-tetrahydro-6H-pyrazolo[3,4-c]pyridin-6-carboxylate 1H-NMR (600 MHz, CDCl3) δ 8.27(bs, 1H), 8.23 (m, 2H), 7.82-7.87 (m, 2H), 7.54 (d, J=8.3 Hz, 2H), 7.16(bs, 1H), 5.28 (d, J=10.3 Hz, 2H), 4.66 (s, 2H), 3.75 (t, J=5.9 Hz, 2H), 2.61(bs, 2H), Mass[M+H]$^+$: 395.9.

Synthetic Example 35. Preparation of 6-benzyl-2-(5-chloropyridin-2-yl)-4,5,6,7-tetrahydro-2H-pyrazolo[3,4-c]pyridin-3-ol Ethyl 1-benzyl-3-oxo-4-piperidine-carboxylate hydrochloride (0.50 g, 1.68 mmol) and 5-chloro-2-hydrazinopyridine (0.24 g, 1.68 mmol) were dissolved in 10 mL eethanol and acetate 2 drops were added. The reaction mixture was stirred at a room temperature for 1 hour and sodium triacetoxyborohhydride (0.53 g, 2.52 mmol) was added and then stirred for 30 hours. The reaction mixture was concentrated under reduced pressure and then it was extracted with water and dichloromethane. The organic layer was dried with magnesium sulfate and filtered and concentrated under reduced pressure. The reaction mixture was recrystallized with ethylacetate to obtain the title compound (0.12 g, 22%).

$^1$H NMR (600 MHz, DMSO-d6) δ 11.54 (brs, 1H), 8.40 (d, J=2.4 Hz, 1H), 8.35 (s, 1H), 7.97 (dd, J=8.4, 2.4 Hz, 1H), 7.34-7.28 (m, 4H), 7.26-7.20 (m, 1H), 3.64 (s, 2H), 3.33 (s, 2H), 2.63 (t, J=5.8 Hz, 2H), 2.23 (t, J=5.3 Hz, 2H). MS Calcd.: 340.1; MS Found: 341.1([M+H]).

Synthetic Example 36. Preparation of 4-(6-benzyl-3-hydroxy-4,5,6,7-tetrahydropyrazolo[3,4-c]pyridin-2-yl)-benzoic acid hydrochloride By using ethyl 1-benzyl-3-oxo-4-piperidine-carboxylate hydrochloride (0.50 g, 1.68 mmol) and 4-hydrazino benzoic acid hydrochloride (0.31 g, 1.68 mmol), the title compound (0.28 g, 43%) was obtained according to the preparation method of Synthetic example 38 below.

$^1$H NMR (600 MHz, DMSO-d6) δ 12.96 (brs, 1H), 10.61 (brs, 1H), 7.97 (d, J=8.8 Hz, 2H), 7.84 (d, J=8.8 Hz, 2H), 7.61-7.52 (m, 2H), 7.51-7.43 (m, 3H), 4.52-4.36 (m, 2H), 4.28-4.12 (m, 2H), 3.75-3.51 (m, 1H), 3.30-3.15 (m, 1H), 2.90-2.65 (m, 2H). MS Calcd.: 349.1; MS Found: 350.1 ([M+H]$^+$).

Synthetic Example 37. Preparation of 6-benzyl-2-(4-bromophenyl)-4,5,6,7-tetrahydro-2H-pyrazolo[3,4-c]pyridin-3-ol hydrochloride By using ethyl 1-benzyl-3-oxo-4-piperidine-carboxylate hydrochloride (0.50 g, 1.68 mmol) and 4-bromophenylhydrazine hydrochloride (0.35 g, 1.68 mmol), the title compound (0.29 g, 41%) was obtained according to the preparation method of Synthetic example 38 below.

$^1$H NMR (600 MHz, DMSO-d6) δ 10.65(brs, 1H), 7.65-7.59 (m, 4H), 7.59-7.53 (m, 2H), 7.51-7.41 (m, 3H), 4.50-4.38 (m, 2H), 4.22-4.07 (m, 2H), 3.65-3.50 (m, 1H), 3.27-3.10(m, 1H), 2.85-2.65(m, 2H). MS Calcd.: 383.1; MS Found: 384.1([M+H]$^+$).

Synthetic Example 38. Preparation of 6-benzyl-2-phenyl-4,5,6,7-tetrahydro-2H-pyrazolo[3,4-c]pyridin-3-ol hydrochloride Ethyl 1-benzyl-3-oxo-4-piperidine-carboxylate hydrochloride (0.50 g, 1.68 mmol) and phenylhydrazine hydrochloride (0.24 g, 1.68 mmol) were dissolved in 10 mL ethanol, and then acetate 2 drops were added. The reaction mixture was stirred at 120° C. for 1 hour and then concentrated under reduced pressure. The reaction mixture was recrystallized with ethanol and diethylether to obtain the title compound (0.25 g, 44%).

$^1$H NMR (600 MHz, DMSO-d6) δ 10.30(brs, 1H), 7.63(d, J=8.0 Hz, 2H), 7.60-7.51 (m, 2H), 7.50-7.44 (m, 3H), 7.41(t, J=7.7 Hz, 2H), 7.31-7.20 (m, 1H), 4.44 (s, 2H), 4.30-4.07 (m, 2H), 3.63 (dd, 1H), 3.25-3.19 (m, 1H), 2.84-2.60(m, 2H). MS Calcd.: 305.1; MS Found: 306.1([M+H]$^+$).

General Synthesis Process 4 (Synthetic Examples 34, 39 to 42, 45 to 52, 59 to 64, 71, 72, 75 to 81)

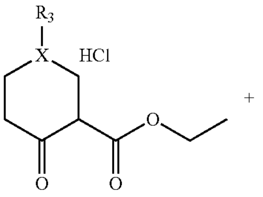

$X{=}CH$ or N

VI

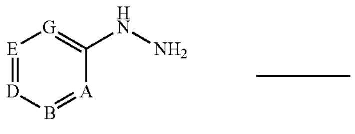

$A{=}CR_5$ or N, $B{=}CR_6$ or N, $D{=}CR_7$ or N, $E{=}CR_8$ or N, $G{=}CH_9$ or N

VII

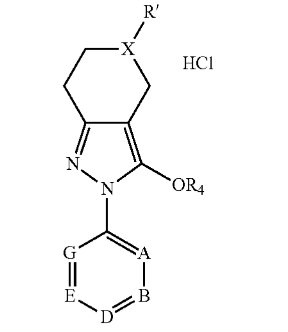

$R'{=}R_a{-}L{-}$, $R_a{-}L{-}CO$, $R_a{-}L{-}NHCO$, $R_a{-}L{-}SO_2$

VIII

Synthetic examples 34, 39 to 42, 45 to 52, 59 to 64, 71, 72, 75 to 81 are synthesized according to the above general reaction formula, and an example of the synthesis method which applies a specific compound is as below. Furthermore, the data of synthetic examples according to the synthesis method were described.

Synthetic Example 39. Preparation of 5-benzyl-2-(5-trifluoromethyl-pyridin-2-yl)-4,5,6,7-tetrahydro-2H-pyrazolo[4,3-c]pyridin-3-ol hydrochloride Ethyl 1-benzyl-4-oxo-3-piperidine-carboxylate hydrochloride (0.50 g, 1.68 mmol) and 2-hydrazinyl-5-(trifluoromethyl)pyridine (0.29 g, 1.68 mmol) were dissolved in 10 mL acetate and stirred at 65° C. for 12 hours. The reaction mixture was concentrated under reduced pressure and then recrystallized with ethanol to obtain the title compound (0.14 g, 21%).

$^1$H NMR (600 MHz, DMSO-d6) δ 10.99 (brs, 1H), 8.90-8.78 (m, 1H), 8.60-8.45 (m, 1H), 8.30 (d, J=9.8 Hz, 1H), 7.65-7.55 (m, 2H), 7.48-7.43 (m, 3H), 4.60-4.30 (m, 2H), 3.90-3.60 (m, 3H), 3.50-3.20(m, 1H), 3.10-2.80(m, 2H). MS Calcd.: 374.1; MS Found: 375.1([M+H]$^+$).

Synthetic Example 40. Preparation of 5-benzyl-2-phenyl-4,5,6,7-tetrahydro-2H-pyrazolo[4,3-c]pyridin-3-ol hydrochloride By using ethyl 1-benzyl-4-oxo-3-piperidine-carboxylate hydrochloride (1.02 g, 3.46 mmol) and phenylhydrazine hydrochloride (0.50 g, 3.46 mmol), the title compound (0.48 g, 41%) was obtained according to the preparation method of Synthetic example 38 above.

$^1$H NMR (600 MHz, DMSO-$d_6$) δ 10.94(brs, 1 Hz), 7.68-7.60 (m, 4H), 7.50-7.44 (m, 3H), 7.40(t, J=7.7 Hz, 2H), 7.22(t, J=7.3 Hz, 1H), 4.54-4.46 (m, 1H), 4.36(dd, J=12.6, 5.9 Hz, 1H), 4.06-3.87 (m, 2H), 3.72-3.66 (m, 1H), 3.38-3.28 (m, 1H), 3.08-2.96 (m, 1H), 2.90-2.81(m, 1H). MS Calcd.: 305.1; MS Found: 306.2([M+H]$^+$).

Synthetic Example 41. Preparation of 5-benzyl-2-(4-bromophenyl)-4,5,6,7-tetrahydro-2H-pyrazolo[4,3-c]pyridin-3-ol hydrochloride By using ethyl 1-benzyl-4-oxo-3-piperidine-carboxylate hydrochloride (0.50 g, 1.68 mmol) and 4-bromophenylhydrazine hydrochloride (0.38 g, 1.68 mmol), the title compound (0.17 g, 24%) was obtained according to the preparation method of Synthetic example 38 above.

$^1$H NMR (600 MHz, DMSO-$d_6$) δ 11.10(brs, 1H), 7.66-7.61 (m, 4H), 7.67-7.61 (m, 2H), 7.47-7.43 (m, 3H), 4.54-4.42 (m, 1H), 4.40-4.30 (m, 1H), 4.05-3.85 (m, 2H), 3.70-3.60 (m, 1H), 3.40-3.21 (m, 1H), 3.10-2.95(m, 1H), 2.90-2.80(m, 1H). MS Calcd.: 383.1; MS Found: 384.1([M+H]$^+$).

Synthetic Example 42. Preparation of 5-benzyl-2-(2-chlorophenyl)-4,5,6,7-tetrahydro-2H-pyrazolo[4,3-c]pyridin-3-ol hydrochloride By using ethyl 1-benzyl-4-oxo-3-piperidine-carboxylate hydrochloride (0.50 g, 1.68 mmol) and 2-chlorophenylhydrazine hydrochloride (0.30 g, 1.68 mmol), the title compound (0.23 g, 36%) was obtained according to the preparation method of Synthetic example 38 above.

$^1$H NMR (600 MHz, DMSO-$d_6$) δ 11.19(brs, 1H), 7.71-7.67 (m, 2H), 7.65-7.60 (m, 1H), 7.52-7.45 (m, 5H), 7.41 (d, J=7.3 Hz, 1H), 4.54 (dd, J=12.6, 3.5 Hz, 1H), 4.39 (dd, J=12.6, 6.3 Hz, 1H), 4.09-3.91 (m, 2H), 3.68 (t, J=13.6 Hz, 1H), 3.45-3.31 (m, 1H), 3.14-3.00 (m, 1H), 2.93-2.79 (m, 1H). MS Calcd.: 339.1; MS Found: 340.2([M+H]$^+$).

TABLE 1

Compounds of Synthetic examples 1 to 81

| | Structure | ESI-MS [M + H]$^+$ | Name |
|---|---|---|---|
| 1 | 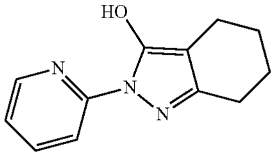 [SMILES: Oc1c2c(nn1-c1ccccn1)CCCC2] | 216.1 | 2-(pyridin-2-yl)-4,5,6,7-tetrahydro-2H-indazol-3-ol |
| 2 | 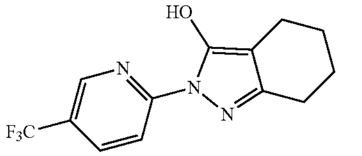 [SMILES: Oc1c2c(nn1-c1ccc(C(F)(F)F)cn1)CCCC2] | 284.1 | 2-(5-(trifluoromethyl)pyridin-2-yl)-4,5,6,7-tetrahydro-2H-indazol-3-ol |
| 3 | 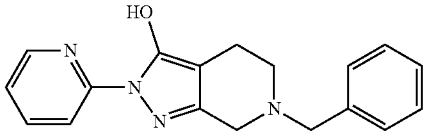 [SMILES: Oc1c2c(nn1-c1ccccn1)CN(Cc1ccccc1)CC2] | 307.2 | 6-benzyl-2-(pyridin-2-yl)-4,5,6,7-tetrahydro-2H-pyrazolo[3,4-c]pyridin-3-ol |
| 4 | 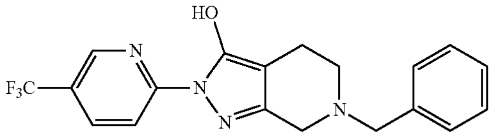 [SMILES: Oc1c2c(nn1-c1ccc(C(F)(F)F)cn1)CN(Cc1ccccc1)CC2] | 375.1 | 6-benzyl-2-(5-(trifluoromethyl)pyridin-2-yl)-4,5,6,7-tetrahydro-2H-pyrazolo[3,4-c]pyridin-3-ol |
| 5 | 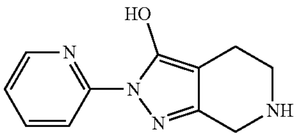 [SMILES: Oc1c2c(nn1-c1ccccn1)CNCC2] | 217.1 | 2-(pyridin-2-yl)-4,5,6,7-tetrahydro-2H-pyrazolo[3,4-c]pyridin-3-ol |
| 6 | 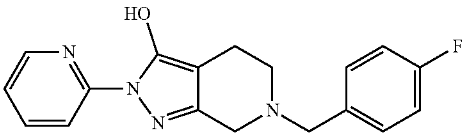 [SMILES: Oc1c2c(nn1-c1ccccn1)CN(Cc1ccc(F)cc1)CC2] | 325.1 | 6-(4-fluorobenzyl)-2-(pyridin-2-yl)-4,5,6,7-tetrahydro-2H-pyrazolo[3,4-c]pyridin-3-ol |

TABLE 1-continued

Compounds of Synthetic examples 1 to 81

| | Structure | ESI-MS $[M + H]^+$ | Name |
|---|---|---|---|
| 7 | 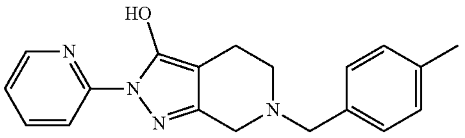 [SMILES: Cc1ccc(CN2CCc3c(nn(-c4ccccn4)c3O)C2)cc1] | 321.2 | 6-(4-methylbenzyl)-2-(pyridin-2-yl)-4,5,6,7-tetrahydro-2H-pyrazolo[3,4-c]pyridin-3-ol |
| 8 | 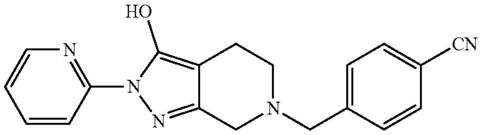 [SMILES: N#Cc1ccc(CN2CCc3c(nn(-c4ccccn4)c3O)C2)cc1] | 332.1 | 4-((3-hydroxy-2-(pyridin-2-yl)-2,4,5,7-tetrahydro-6H-pyrazolo[3,4-c]pyridin-6-yl)methyl)benzonitrile |
| 9 | 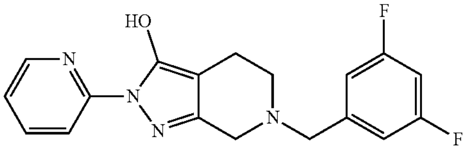 [SMILES: Oc1c2c(nn1-c1ccccn1)CN(Cc1cc(F)cc(F)c1)CC2] | 343.1 | 6-(3,5-difluorobenzyl)-2-(pyridin-2-yl)-4,5,6,7-tetrahydro-2H-pyrazolo[3,4-c]pyridin-3-ol |
| 10 | 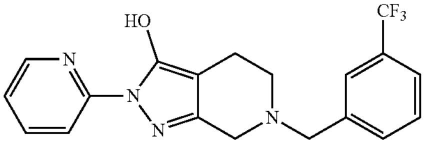 [SMILES: Oc1c2c(nn1-c1ccccn1)CN(Cc1cccc(C(F)(F)F)c1)CC2] | 375.1 | 2-(pyridin-2-yl)-6-(3-(trifluoromethyl)benzyl)-4,5,6,7-tetrahydro-2H-pyrazolo[3,4-c]pyridin-3-ol |
| 11 | 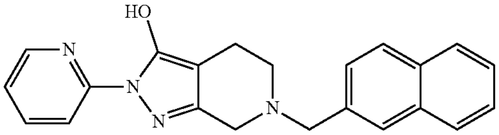 [SMILES: Oc1c2c(nn1-c1ccccn1)CN(Cc1ccc3ccccc3c1)CC2] | 357.2 | 6-(naphthalene-2-ylmethyl)-2-(pyridin-2-yl)-4,5,6,7-tetrahydro-2H-pyrazolo[3,4-c]pyridin-3-ol |
| 12 | 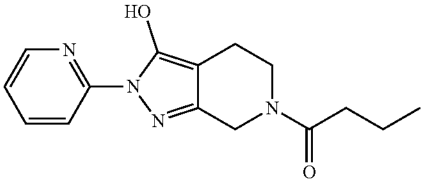 [SMILES: CCCC(=O)N1CCc2c(nn(-c3ccccn3)c2O)C1] | 287.1 | 1-(4,5-dihydro-3-hydroxy-2-(pyridin-2-yl)-2H-pyrazolo[3,4-c]pyridin-6(7H)-yl)butan-1-one |
| 13 | 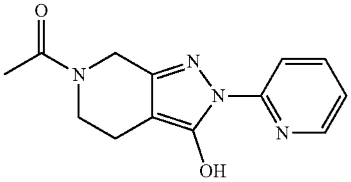 [SMILES: CC(=O)N1CCc2c(nn(-c3ccccn3)c2O)C1] | 259.1 | 1-(3-hydroxy-2-(pyridin-2-yl)-2,4,5,7-tetrahydro-6H-pyrazolo[3,4-c]pyridin-6-yl)ethan-1-one |
| 14 | 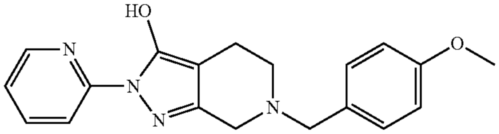 [SMILES: COc1ccc(CN2CCc3c(nn(-c4ccccn4)c3O)C2)cc1] | 337.2 | 6-(4-methoxybenzyl)-2-(pyridin-2-yl)-4,5,6,7-tetrahydro-2H-pyrazolo[3,4-c]pyridin-3-ol |
| 15 | 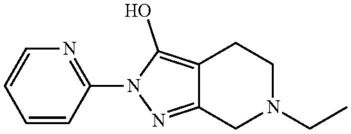 [SMILES: CCN1CCc2c(nn(-c3ccccn3)c2O)C1] | 245.1 | 6-ethyl-2-(pyridin-2-yl)-4,5,6,7-tetrahydro-2H-pyrazolo[3,4-c]pyridin-3-ol |

TABLE 1-continued

| Compounds of Synthetic examples 1 to 81 | | | |
|---|---|---|---|
| | Structure | ESI-MS $[M + H]^+$ | Name |
| 16 | 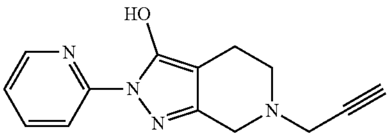 [SMILES: C#CCN1CCc2c(nn(-c3ccccn3)c2O)C1] | 255.1 | 6-(prop-2-yn-1-yl)-2(pyridin-2-yl)-4,5,6,7-tetrahydro-2H-pyrazolo[3,4-c]pyridin-3-ol |
| 17 | 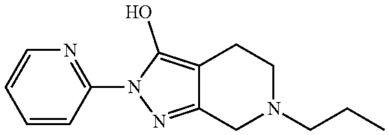 [SMILES: CCCN1CCc2c(nn(-c3ccccn3)c2O)C1] | 259.2 | 6-propyl-2-(pyridin-2-yl)-4,5,6,7-tetrahydro-2H-pyrazolo[3,4-c]pyridin-3-ol |
| 18 | 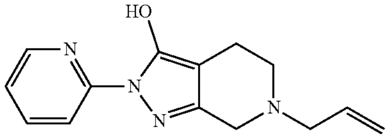 [SMILES: C=CCN1CCc2c(nn(-c3ccccn3)c2O)C1] | 257.1 | 6-allyl-2-(pyridin-2-yl)-4,5,6,7-tetrahydro-2H-pyrazolo[3,4-c]pyridin-3-ol |
| 19 | 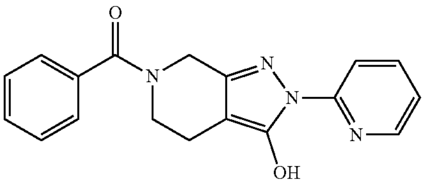 [SMILES: O=C(c1ccccc1)N1CCc2c(nn(-c3ccccn3)c2O)C1] | 321.1 | (3-hydroxy-2-(pyridin-2-yl)-2,4,5,7-tetrahydro-6H-pyrazolo[3,4-c]pyridin-6-yl)(phenyl)methanone |
| 20 | 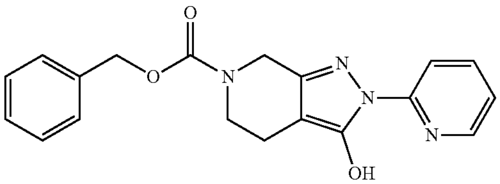 [SMILES: O=C(OCc1ccccc1)N1CCc2c(nn(-c3ccccn3)c2O)C1] | 351.1 | benzyl 3-hydroxy-2-(pyridin-2-yl)-2,4,5,7-tetrahydro-6H-pyrazolo[3,4-c]pyridin-6-carboxylate |
| 21 | 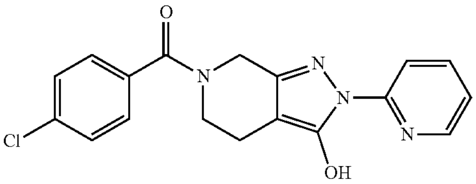 [SMILES: O=C(c1ccc(Cl)cc1)N1CCc2c(nn(-c3ccccn3)c2O)C1] | 355.1 | (4-chlorophenyl)(3-hydroxy-2-(pyridin-2-yl)-2,4,5,7-tetrahydro-6H-pyrazolo[3,4-c]pyridin-5-yl)methanone |
| 22 | 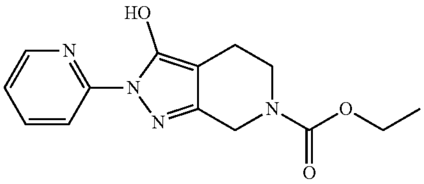 [SMILES: CCOC(=O)N1CCc2c(nn(-c3ccccn3)c2O)C1] | 289.1 | ethyl 3-hydroxy-2-(pyridin-2-yl)-2,4,5,7-tetrahydro-6H-pyrazolo[3,4-c]pyridin-6-carboxylate |
| 23 | 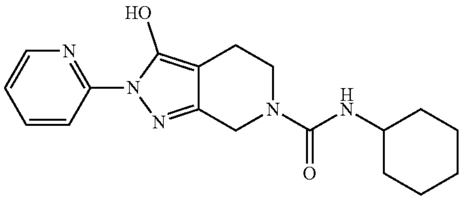 [SMILES: O=C(NC1CCCCC1)N1CCc2c(nn(-c3ccccn3)c2O)C1] | 342.2 | N-cyclohexyl-3-hydroxy-2-(pyridin-2-yl)-2,4,5,7-tetrahydro-6H-pyrazolo[3,4-c]pyridin-6-carboxamide |

TABLE 1-continued

| Compounds of Synthetic examples 1 to 81 | | | |
|---|---|---|---|
| | Structure | ESI-MS $[M + H]^+$ | Name |
| 24 | 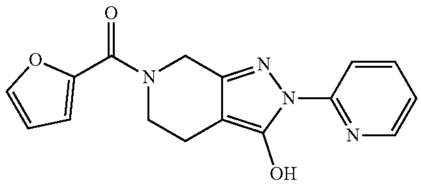 [SMILES: O=C(c1ccco1)N1CCc2c(nn(-c3ccccn3)c2O)C1] | 311.1 | furan-2-yl(3-hydroxy-2-(pyridin-2-yl)-2,4,5,7-tetrahydro-6H-pyrazolo[3,4-c]pyridin-6-yl)methanone |
| 25 | 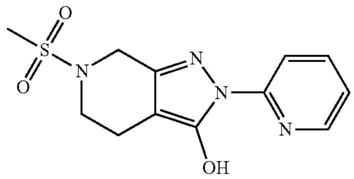 [SMILES: CS(=O)(=O)N1CCc2c(nn(-c3ccccn3)c2O)C1] | 295.1 | 6-(methylsulfonyl)-2-(pyridin-2-yl)-4,5,6,7-tetrahydro-2H-pyrazolo[3,4-c]pyridin-3-ol |
| 26 | 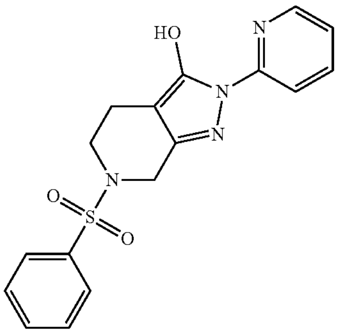 [SMILES: O=S(=O)(c1ccccc1)N1CCc2c(nn(-c3ccccn3)c2O)C1] | 357.1 | 6-(phenylsulfonyl)-2-(pyridin-2-yl)-4,5,6,7-tetrahydro-2H-pyrazolo[3,4-c]pyridin-3-ol |
| 27 | 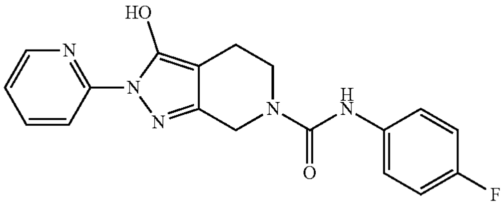 [SMILES: O=C(Nc1ccc(F)cc1)N1CCc2c(nn(-c3ccccn3)c2O)C1] | 354.1 | N-(4-fluorophenyl)-3-hydroxy-2-(pyridin-2-yl)-2,4,5,7-tetrahydro-6H-pyrazolo[3,4-c]pyridin-6-carboxamide |
| 28 | 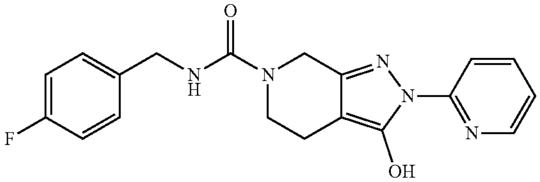 [SMILES: O=C(NCc1ccc(F)cc1)N1CCc2c(nn(-c3ccccn3)c2O)C1] | 368.1 | N-(4-fluorobenzyl)-3-hydroxy-2-(pyridin-2-yl)-2,4,5,7-tetrahydro-6H-pyrazolo[3,4-c]pyridin-6-carboxamide |
| 29 | 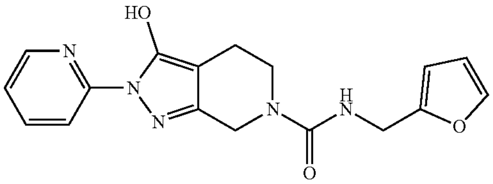 [SMILES: O=C(NCc1ccco1)N1CCc2c(nn(-c3ccccn3)c2O)C1] | 340.1 | N-(furan-2-ylmethyl)-3-hydroxy-2-(pyridin-2-yl)-2,4,5,7-tetrahydro-6H-pyrazolo[3,4-c]pyridin-6-carboxamide |
| 30 | 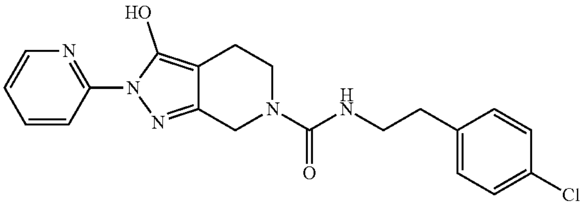 [SMILES: O=C(NCCc1ccc(Cl)cc1)N1CCc2c(nn(-c3ccccn3)c2O)C1] | 398.1 | N-(4-chlorophenethyl)-3-hydroxy-2-(pyridin-2-yl)-2,4,5,7-tetrahydro-6H-pyrazolo[3,4-c]pyridin-6-carboxamide |

TABLE 1-continued

| Compounds of Synthetic examples 1 to 81 | | | |
|---|---|---|---|
| | Structure | ESI-MS $[M + H]^+$ | Name |
| 31 | 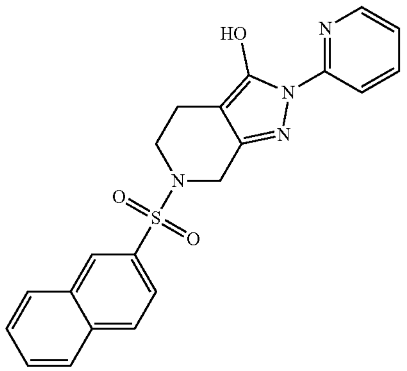 [SMILES: O=S(=O)(c1ccc2ccccc2c1)N1CCc2c(nn(-c3ccccn3)c2O)C1] | 407.1 | 6-(naphthalene-2-ylsulfonyl)-2-(pyridin-2-yl)-4,5,6,7-tetrahydro-2H-pyrazolo[3,4-c]pyridin-3-ol |
| 32 | 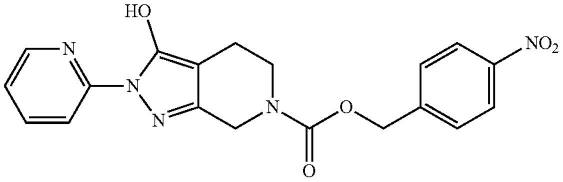 [SMILES: O=C(OCc1ccc([N+](=O)[O-])cc1)N1CCc2c(nn(-c3ccccn3)c2O)C1] | 396.1 | 4-nitrobenzyl 3-hydroxy-2-(pyridin-2-yl)-2,4,5,7-tetrahydro-6H-pyrazolo[3,4-c]pyridin-6-carboxylate |
| 33 | 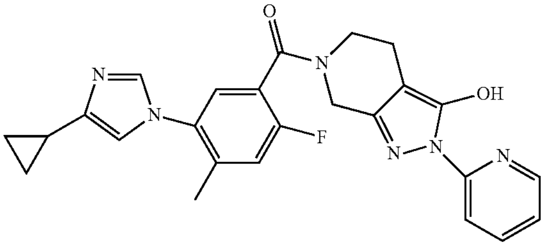 [SMILES: Cc1cc(F)c(C(=O)N2CCc3c(nn(-c4ccccn4)c3O)C2)cc1-n1cnc(C2CC2)c1] | 459.2 | (5-(4-cyclopropyl-1H-imidazol-1-yl)-2-fluoro-4-methylphenyl)(3-hydroxy-2-(pyridin-2-yl)-2,4,5,7-tetrahydro-6H-pyrazolo[3,4-c]pyridin-6-yl)methanone |
| 34 | 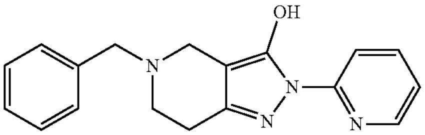 [SMILES: Oc1c2c(nn1-c1ccccn1)CCN(Cc1ccccc1)C2] | 307.2 | 5-benzyl-2-(pyridin-2-yl)-4,5,6,7-tetrahydro-2H-pyrazolo[4,3-c]pyridin-3-ol |
| 35 | 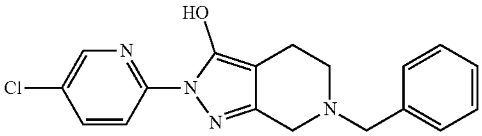 [SMILES: Oc1c2c(nn1-c1ccc(Cl)cn1)CN(Cc1ccccc1)CC2] | 341.1 | 6-benzyl-2-(5-chloropyridin-2-yl)-4,5,6,7-tetrahydro-2H-pyrazolo[3,4-c]pyridin-3-ol |
| 36 | 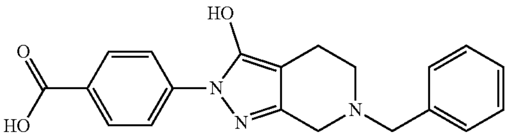 [SMILES: O=C(O)c1ccc(-n2nc3c(c2O)CCN(Cc2ccccc2)C3)cc1] | 350.1 | 4-(6-benzyl-3-hydroxy-4,5,6,7-tetrahydro-2H-pyrazolo[3,4-c]pyridin-2-yl)benzoic acid |
| 37 | 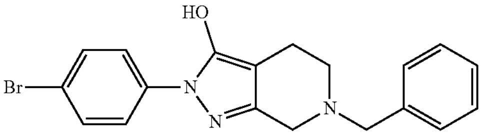 | 384.1 | 6-benzyl-2-(4-bromophenyl)-4,5,6,7-tetrahydro-2H-pyrazolo[3,4-c]pyridin-3-ol |

TABLE 1-continued

Compounds of Synthetic examples 1 to 81

| | Structure | ESI-MS $[M + H]^+$ | Name |
|---|---|---|---|
| 38 | 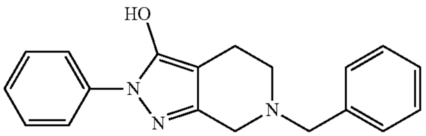 | 306.2 | 6-benzyl-2-phenyl-4,5,6,7-tetrahydro-2H-pyrazolo[3,4-c]pyridin-3-ol |
| 39 | 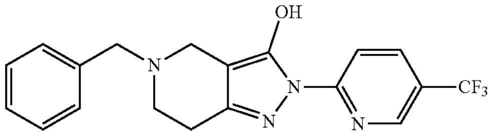 [SMILES: Oc1c2c(nn1-c1ccc(C(F)(F)F)cn1)CCN(Cc1ccccc1)C2] | 375.1 | 5-benzyl-2-(5-trifluoromethyl)pyridin-2-yl)-4,5,6,7-tetrahydro-2H-pyrazolo[4,3-c]pyridin-3-ol |
| 40 | 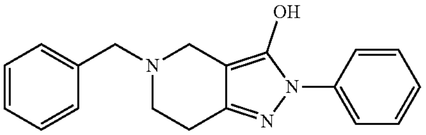 [SMILES: Oc1c2c(nn1-c1ccccc1)CCN(Cc1ccccc1)C2] | 306.2 | 5-benzyl-2-phenyl-4,5,6,7-tetrahydro-2H-pyrazolo[4,3-c]pyridin-3-ol |
| 41 | 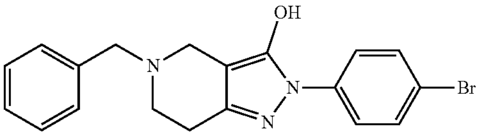 [SMILES: Oc1c2c(nn1-c1ccc(Br)cc1)CCN(Cc1ccccc1)C2] | 384.1 | 5-benzyl-2-(4-bromophenyl)-4,5,6,7-tetrahydro-2H-pyrazolo[4,3-c]pyridin-3-ol |
| 42 | 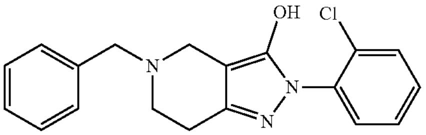 [SMILES: Oc1c2c(nn1-c1ccccc1Cl)CCN(Cc1ccccc1)C2] | 340.1 | 5-benzyl-2-(2-chlorophenyl)-4,5,6,7-tetrahydro-2H-pyrazolo[4,3-c]pyridin-3-ol |
| 43 | 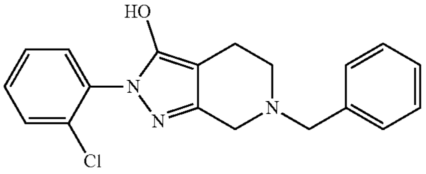 [SMILES: Oc1c2c(nn1-c1ccccc1Cl)CN(Cc1ccccc1)CC2] | 340.1 | 6-benzyl-2-(2-chlorophenyl)-4,5,6,7-tetrahydro-2H-pyrazolo[3,4-c]pyridin-3-ol |
| 44 | 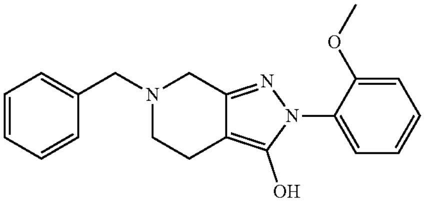 [SMILES: COc1ccccc1-n1nc2c(c1O)CCN(Cc1ccccc1)C2] | 336.2 | 6-benzyl-2-(2-methoxyphenyl)-4,5,6,7-tetrahydro-2H-pyrazolo[3,4-c]pyridin-3-ol |
| 45 | 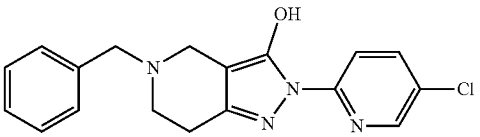 [SMILES: Oc1c2c(nn1-c1ccc(Cl)cn1)CCN(Cc1ccccc1)C2] | 341.1 | 5-benzyl-2-(5-chloropyridin-2-yl)-4,5,6,7-tetrahydro-2H-pyrazolo[4,3-c]pyridin-3-ol |
| 46 | 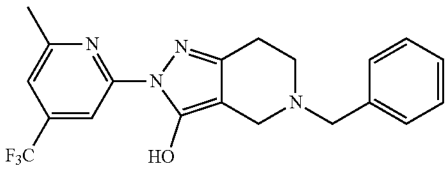 [SMILES: Cc1cc(C(F)(F)F)cc(-n2nc3c(c2O)CN(Cc2ccccc2)CC3)n1] | 389.2 | 5-benzyl-2-(6-methyl-4-(trifluoromethyl)pyridin-2-yl)-4,5,6,7-tetrahydro-2H-pyrazolo[4,3-c]pyridin-3-ol |

TABLE 1-continued

| Compounds of Synthetic examples 1 to 81 | | | |
|---|---|---|---|
| | Structure | ESI-MS $[M + H]^+$ | Name |
| 47 | 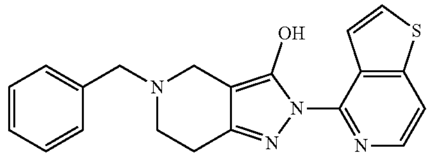 [SMILES: Oc1c2c(nn1-c1nccc3sccc13)CCN(Cc1ccccc1)C2] | 363.1 | 5-benzyl-2-(thieno[3,2-c]pyridin-4-yl)-4,5,6,7-tetrahydro-2H-pyrazolo[4,3-c]pyridin-3-ol |
| 48 | 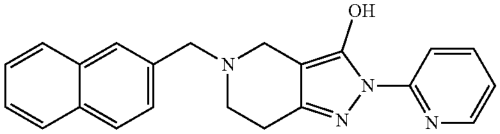 [SMILES: Oc1c2c(nn1-c1ccccn1)CCN(Cc1ccc3ccccc3c1)C2] | 357.2 | 5-(naphthalene-2-ylmethyl)-2-(pyridin-2-yl)-4,5,6,7-tetrahydro-2H-pyrazolo[4,3-c]pyridin-3-ol |
| 49 | 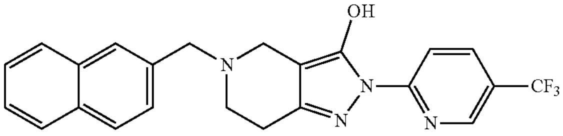 [SMILES: Oc1c2c(nn1-c1ccc(C(F)(F)F)cn1)CCN(Cc1ccc3ccccc3c1)C2] | 425.1 | 5-(naphthalene-2-ylmethyl)-2-(5-(trifluoromethyl)pyridin-2-yl)-4,5,6,7-tetrahydro-2H-pyrazolo[4,3-c]pyridin-3-ol |
| 50 | 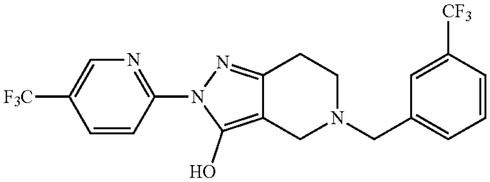 [SMILES: Oc1c2c(nn1-c1ccc(C(F)(F)F)cn1)CCN(Cc1cccc(C(F)(F)F)c1)C2] | 443.1 | 5-(3-(trifluoromethyl)benzyl)-2-(5-(trifluoromethyl)pyridin-2-yl)-4,5,6,7-tetrahydro-2H-pyrazolo[4,3-c]pyridin-3-ol |
| 51 | 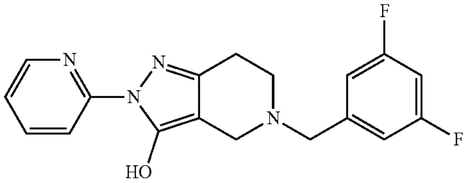 [SMILES: Oc1c2c(nn1-c1ccccn1)CCN(Cc1cc(F)cc(F)c1)C2] | 343.1 | 5-(3,5-difluorobenzyl)-2-(pyridin-2-yl)-4,5,6,7-tetrahydro-2H-pyrazolo[4,3-c]pyridin-3-ol |
| 52 | 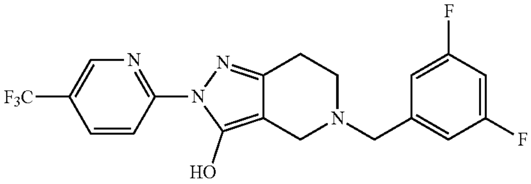 [SMILES: Oc1c2c(nn1-c1ccc(C(F)(F)F)cn1)CCN(Cc1cc(F)cc(F)c1)C2] | 411.1 | 5-(3,5-difluorobenzyl)-2-(5-trifluoromethyl)pyridin-2-yl)-4,5,6,7-tetrahydro-2H-pyrazolo[4,3-c]pyridin-3-ol |
| 53 | 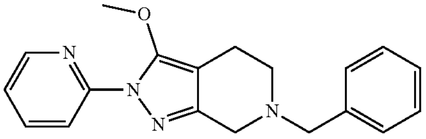 [SMILES: COc1c2c(nn1-c1ccccn1)CN(Cc1ccccc1)CC2] | 321.2 | 6-benzyl-3-methoxy-2-(pyridin-2-yl)-4,5,6,7-tetrahydro-2H-pyrazolo[3,4-c]pyridine |
| 54 | 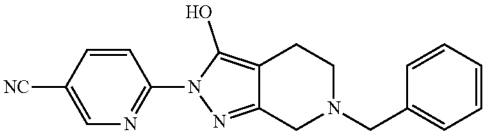 [SMILES: N#Cc1ccc(-n2nc3c(c2O)CCN(Cc2ccccc2)C3)nc1] | 332.1 | 6-(6-benzyl-3-hydroxy-4,5,6,7-tetrahydro-2H-pyrazolo[3,4-c]pyridin-2-yl)nicotinonitrile |
| 55 | 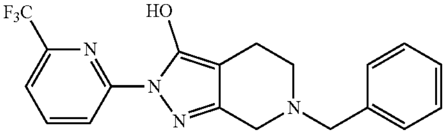 [SMILES: Oc1c2c(nn1-c1cccc(C(F)(F)F)n1)CN(Cc1ccccc1)CC2] | 375.1 | 6-benzyl-2-(6-(trifluoromethyl)pyridin-2-yl)-4,5,6,7-tetrahydro-2H-pyrazolo[3,4-c]pyridin-3-ol |

TABLE 1-continued

Compounds of Synthetic examples 1 to 81

| | Structure | ESI-MS [M + H]+ | Name |
|---|---|---|---|
| 56 | 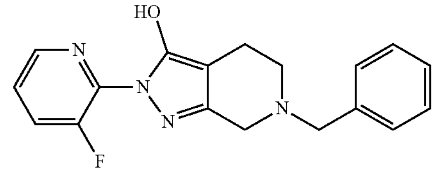 [SMILES: Oc1c2c(nn1-c1ncccc1F)CN(Cc1ccccc1)CC2] | 325.1 | 6-benzyl-2-(3-fluoropyridin-2-yl)-4,5,6,7-tetrahydro-2H-pyrazolo[3,4-c]pyridin-3-ol |
| 57 | 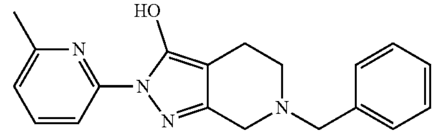 [SMILES: Cc1cccc(-n2nc3c(c2O)CCN(Cc2ccccc2)C3)n1] | 321.2 | 6-benzyl-2-(6-methylpyridin-2-yl)-4,5,6,7-tetrahydro-2H-pyrazolo[3,4-c]pyridin-3-ol |
| 58 | 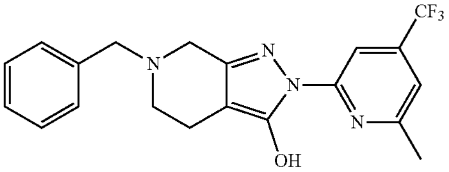 [SMILES: Cc1cc(C(F)(F)F)cc(-n2nc3c(c2O)CCN(Cc2ccccc2)C3)n1] | 389.2 | 6-benzyl-2-(6-methyl-4-(trifluoromethyl)pyridin-2-yl)-4,5,6,7-tetrahydro-2H-pyrazolo[3,4-c]pyridin-3-ol |
| 59 | 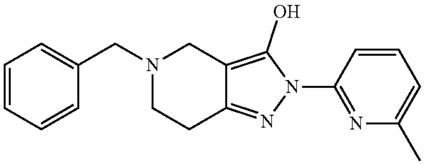 [SMILES: Cc1cccc(-n2nc3c(c2O)CN(Cc2ccccc2)CC3)n1] | 321.2 | 5-benzyl-2-(6-methylpyridin-2-yl)-4,5,6,7-tetrahydro-2H-pyrazolo[4,3-c]pyridin-3-ol |
| 60 | 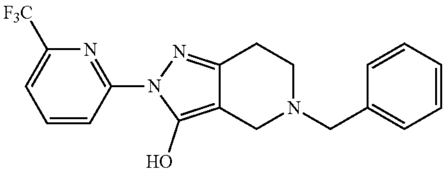 [SMILES: Oc1c2c(nn1-c1cccc(C(F)(F)F)n1)CCN(Cc1ccccc1)C2] | 375.1 | 5-benzyl-2-(6-trifluoromethyl)pyridin-2-yl)-4,5,6,7-tetrahydro-2H-pyrazolo[4,3-c]pyridin-3-ol |
| 61 | 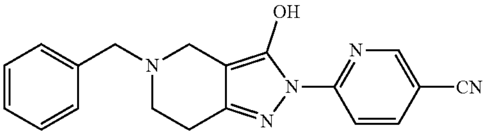 [SMILES: N#Cc1ccc(-n2nc3c(c2O)CN(Cc2ccccc2)CC3)nc1] | 332.1 | 6-(5-benzyl-3-hydroxy-4,5,6,7-tetrahydro-2H-pyrazolo[4,3-c]pyridin-2-yl)nicotinonitrile |
| 62 | 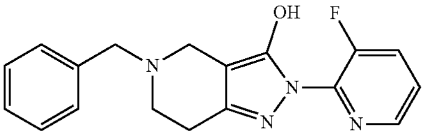 | 325.1 | 5-benzyl-2-(3-fluoropyridin-2-yl)-4,5,6,7-tetrahydro-2H-pyrazolo[4,3-c]pyridin-3-ol |
| 63 | 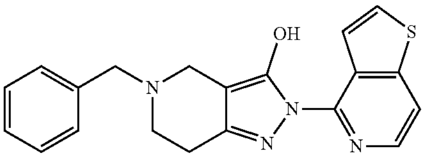 [SMILES: Oc1c2c(nn1-c1nccc3sccc13)CCN(Cc1ccccc1)C2] | 363.1 | 5-benzyl-2-(thieno[3,2-c]pyridin-4-yl)-4,5,6,7-tetrahydro-2H-pyrazolo[4,3-c]pyridin-3-ol |
| 64 | 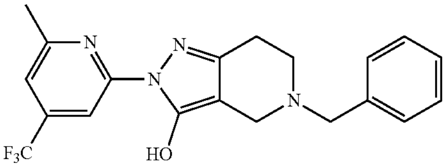 [SMILES: Cc1cc(C(F)(F)F)cc(-n2nc3c(c2O)CN(Cc2ccccc2)CC3)n1] | 389.2 | 5-benzyl-2-(6-methyl-4-(trifluoromethyl)pyridin-2-yl)-4,5,6,7-tetrahydro-2H-pyrazolo[4,3-c]pyridin-3-ol |

TABLE 1-continued

| Compounds of Synthetic examples 1 to 81 | | | |
|---|---|---|---|
| | Structure | ESI-MS [M + H]+ | Name |
| 65 | 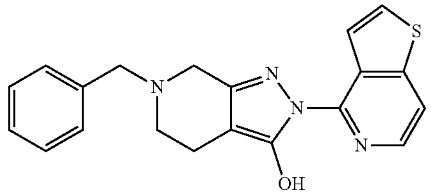 [SMILES: Oc1c2c(nn1-c1nccc3sccc13)CN(Cc1ccccc1)CC2] | 363.1 | 6-benzyl-2-(thieno[3,2-c]pyridin-4-yl)-4,5,6,7-tetrahydro-2H-pyrazolo[3,4-c]pyridin-3-ol |
| 66 | 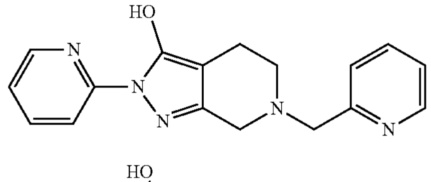 | 308.1 | 2-(pyridin-2-yl)-6-(pyridin-2-ylmethyl)-4,5,6,7-tetrahydro-2H-pyrazolo[3,4-c]pyridin-3-ol |
| 67 | 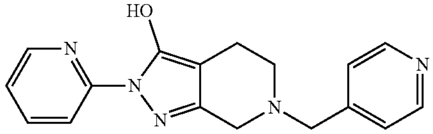 [SMILES: Oc1c2c(nn1-c1ccccn1)CN(Cc1ccncc1)CC2] | 308.1 | 2-(pyridin-2-yl)-6-(pyridin-4-ylmethyl)-4,5,6,7-tetrahydro-2H-pyrazolo[3,4-c]pyridin-3-ol |
| 68 | 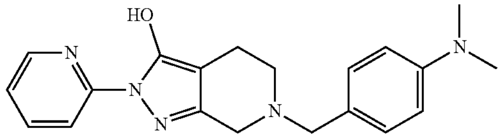 [SMILES: CN(C)c1ccc(CN2CCc3c(nn(-c4ccccn4)c3O)C2)cc1] | 350.2 | 6-(4-(dimethylamino)benzyl)-2-(pyridin-2-yl)-4,5,6,7-tetrahydro-2H-pyrazolo[3,4-c]pyridin-3-ol |
| 69 | 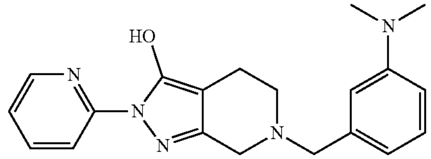 [SMILES: CN(C)c1cccc(CN2CCc3c(nn(-c4ccccn4)c3O)C2)c1] | 350.2 | 6-(3-(dimethylamino)benzyl)-2-(pyridin-2-yl)-4,5,6,7-tetrahydro-2H-pyrazolo[3,4-c]pyridin-3-ol |
| 70 | 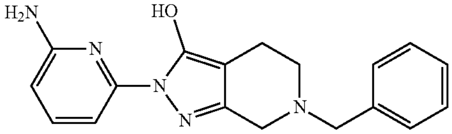 [SMILES: Nc1cccc(-n2nc3c(c2O)CCN(Cc2ccccc2)C3)n1] | 322.2 | 2-(6-aminopyridin-2-yl)-6-benzyl-4,5,6,7-tetrahydro-2H-pyrazolo[3,4-c]pyridin-3-ol |
| 71 | 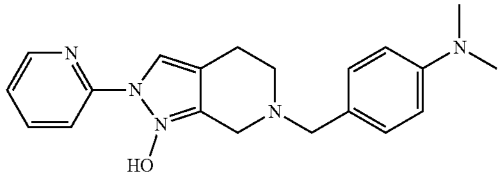 | 350.2 | 5-(4-(dimethylamino)benzyl)-2-(pyridin-2-yl)-4,5,6,7-tetrahydro-2H-pyrazolo[4,3-c]pyridin-3-ol |
| 72 | 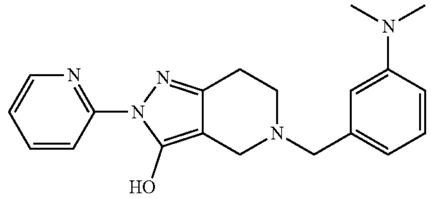 [SMILES: CN(C)c1cccc(CN2CCc3nn(-c4ccccn4)c(O)c3C2)c1] | 350.2 | 5-(3-(dimethylamino)benzyl)-2-(pyridin-2-yl)-4,5,6,7-tetrahydro-2H-pyrazolo[4,3-c]pyridin-3-ol |
| 73 | 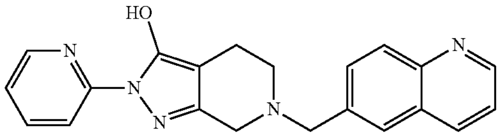 [SMILES: Oc1c2c(nn1-c1ccccn1)CN(Cc1ccc3ncccc3c1)CC2] | 358.2 | 2-(pyridin-2-yl)-6-(quinolin-6-ylmethyl)-4,5,6,7-tetrahydro-2H-pyrazolo[3,4-c]pyridin-3-ol |

TABLE 1-continued

Compounds of Synthetic examples 1 to 81

| | Structure | ESI-MS [M + H]+ | Name |
|---|---|---|---|
| 74 | 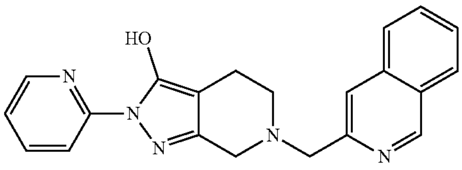 [SMILES: Oc1c2c(nn1-c1ccccn1)CN(Cc1cc3ccccc3cn1)CC2] | 358.2 | 6-(isoquinolin-3-ylmethyl)-2-(pyridin-2-yl)-4,5,6,7-tetrahydro-2H-pyrazolo[3,4-c]pyridin-3-ol |
| 75 | 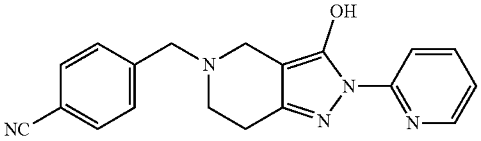 [SMILES: N#Cc1ccc(CN2CCc3nn(-c4ccccn4)c(O)c3C2)cc1] | 332.1 | 4-((3-hydroxy-2-(pyridin-2-yl)-2,4,6,7-tetrahydro-5H-pyrazolo[4,3-c]pyridin-5-yl)methyl)benzonitrile |
| 76 | 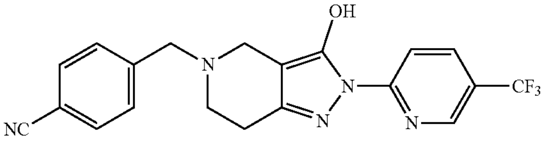 [SMILES: N#Cc1ccc(CN2CCc3nn(-c4ccc(C(F)(F)F)cn4)c(O)c3C2)cc1] | 400.1 | 4-((3-hydroxy-2-(5-(trifluoromethyl)pyridin-2-yl)-2,4,6,7-tetrahydro-5H-pyrazolo[4,3-c]pyridin-5-yl)methyl)benzonitrile |
| 77 | 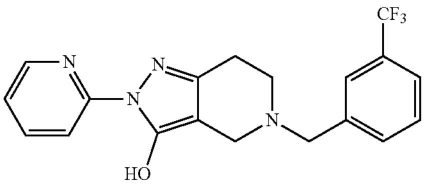 [SMILES: Oc1c2c(nn1-c1ccccn1)CCN(Cc1cccc(C(F)(F)F)c1)C2] | 375.1 | 2-(pyridin-2-yl)-5-(3-(trifluoromethyl)benzyl)-4,5,6,7-tetrahydro-2H-pyrazolo[4,3-c]pyridin-3-ol |
| 78 | 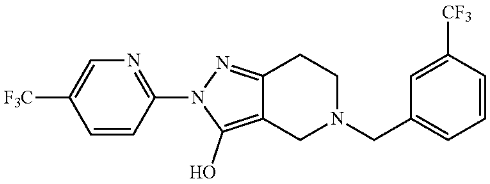 [SMILES: Oc1c2c(nn1-c1ccc(C(F)(F)F)cn1)CCN(Cc1cccc(C(F)(F)F)c1)C2] | 443.1 | 5-(3-(trifluoromethyl)benzyl)-2-(5-(trifluoromethyl)pyridin-2-yl)-4,5,6,7-tetrahydro-2H-pyrazolo[4,3-c]pyridin-3-ol |
| 79 | 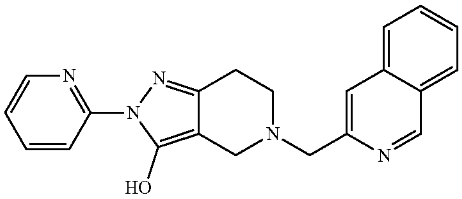 [SMILES: Oc1c2c(nn1-c1ccccn1)CCN(Cc1cc3ccccc3cn1)C2] | 358.2 | 5-(isoquinolin-3-ylmethyl)-2-(pyridin-2-yl)-4,5,6,7-tetrahydro-2H-pyrazolo[4,3-c]pyridin-3-ol |
| 80 | 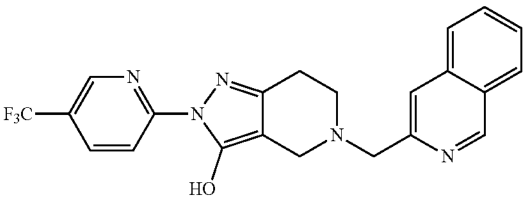 [SMILES: Oc1c2c(nn1-c1ccc(C(F)(F)F)cn1)CCN(Cc1cc3ccccc3cn1)C2] | 426.2 | 5-(isoquinolin-3-ylmethyl)-2-(5-(trifluoromethyl)pyridin-2-yl)-4,5,6,7-tetrahydro-2H-pyrazolo[4,3-c]pyridin-3-ol |
| 81 | 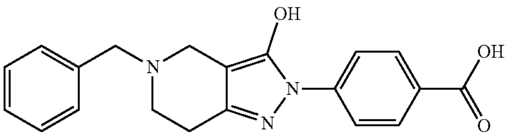 [SMILES: O=C(O)c1ccc(-n2nc3c(c2O)CN(Cc2ccccc2)CC3)cc1] | 350.1 | 4-(5-benzyl-3-hydroxy-4,5,6,7-tetrahydro-2H-pyrazolo[4,3-c]pyridin-2-yl)benzoic acid |

Example 1

In order to confirm an effect of the synthetic example compounds on ROS production from fibroblasts and specific substrate cells, ROS production was induced by stimulation of PMA (phorbol 12-myristate 13-acetate), TGF-β1, palmitate or high concentration-glucose, or the like for HL-60 cells (Korean Cell Line Bank), NHLF(normal human lung fibroblast, Lonza), LX-2 (human hepatic stellate cells, Sigma), ARPE19 (human retinal pigment epithelial cell, ATCC), KEL-FIB (Keloid fibroblast, ATCC) cells differentiated into neutrophil cells by treatment of DMSO, and the inhibitory effect of ROS production of the synthetic example compounds was observed under this condition.

HL-60 cells (human leukemia cells, ATCC) was suspended in a medium comprising 1.25% DMSO (RPMI+10% FBS) and cultured under the condition of 5% $CO_2$, 37° C. for 6 days to induce differentiation into neutrophil cells. The HL-60 cells differentiated into neutrophil cells were aliquoted in a 96 well plate at a concentration of $2\times10^4$ cells/well, and the synthetic example compound was treated at a concentration of 0.5 mM for 30 minutes. Then, PMA of 200 mM was treated in each well comprising cells and a drug to induce production of ROS, and this ROS production was measured by observing the level of luminescence of each well using 100 μM L-012.

NHLF (normal human lung fibroblast, Lonza), LX-2 (human hepatic stellate cells, Sigma), ARPE19 (human retinal pigment epithelial cell, ATCC), KEL-FIB (keloid fibroblast, ATCC) cells were suspended in a culture medium comprising 10% FBS and aliquoted in a 96 well plate, and then cultured under the condition of 5% $CO_2$, 37° C. for 24 hours. The synthetic example compound was pretreated from 30 minutes to 1 hour, and then a ROS stimulus was treated to each well comprising cells and a drug. After additional culturing for 48 hours, the level of ROS production was confirmed by using L-012 or DCF-DA.

As the result of the experiment, the synthetic example compounds inhibited ROS production by the ROS stimulus in all the NHLF, LX-2, ARPE19, KEL-FIB cells. The result of Table 2 shows the result that the synthetic example compounds (0.5 uM) inhibited ROS production induced by PMA in HL-60 cells induced into neutrophils, and FIG. 1 shows the result that both Synthetic example 3 and Synthetic example 34 inhibited ROS production induced by PMA in LX-2 and NHLF cells.

Therefore, it was confirmed that the production of ROS was effectively inhibited, when the synthetic example compound was treated to differentiated HL-60 cells or various fibroblasts or specific substrate cells in which ROS production was induced.

TABLE 2

| ROS production inhibitory effect in differentiated HL-60 cells | |
|---|---|
| Synthetic example number | ROS production inhibitory effect |
| 1 | * |
| 2 | * |
| 3 | *** |
| 4 | ** |
| 6 | ** |
| 7 | ** |
| 8 | *** |
| 9 | *** |
| 10 | ** |

TABLE 2-continued

| ROS production inhibitory effect in differentiated HL-60 cells | |
|---|---|
| Synthetic example number | ROS production inhibitory effect |
| 15 | * |
| 16 | * |
| 23 | * |
| 26 | *** |
| 32 | ** |
| 34 | ** |
| 35 | *** |
| 36 | **** |
| 37 | **** |
| 38 | **** |
| 39 | * |
| 40 | *** |
| 41 | *** |
| 42 | * |
| 50 | ** |
| 75 | *** |
| 76 | ** |
| 77 | ** |
| 78 | *** |
| 79 | *** |
| 80 | *** |
| 81 | **** |

<*: <30%,
**: 30 < <50%,
***: 50 < <70%,
****: >70%>

<Example 2> Analysis of Change in Expression of αSMA Induced by TGF-β1

It has been reported that fibroblasts are differentiated into myofibroblasts to form cancer associated fibroblasts (CAFs) or induce fibrosis of various tissues.

In order to confirm whether the synthetic example compound of the present invention affects differentiation of fibroblasts into myofibroblasts, the inhibitory effect of the synthetic example compound for increasing expression of αSMA (a biomarker for confirming differentiation into myofibroblasts) induced by TGF-β1 for HL-60 cells (Korean Cell Line Bank), HFF-1 (human foreskin fibroblast, ATCC), NHLF (normal human lung fibroblast, Lonza), LX-2 (human hepatic stellate cells, Sigma), ARPE19 (human retinal pigment epithelial cell, ATCC), KEL-FIB (Keloid fibroblast, ATCC) cells was to be observed.

Each cell was suspended in a DMEM medium comprising 10% FBS and aliquoted on a 4-well chamber slide (Nunc) at a concentration of $1\times10^4$ cells/well, and the synthetic example compound and TGF-β1(TGF 131, TGF-β are all same meanings) were treated to prepare cells to be used for confirmation of αSMA expression. The confirmation of αSMA expression in the prepared cells was performed by immunocytochemistry as follows. After performing fixation with 4% paraformaldehyde for 10 minutes and permeabilization using 0.1% Triton x-100 for the cells, the process of treating a primary antibody (anti-αSMA Ab, 1:200, at 4° C. for 16 hours) and a secondary antibody (Alexa-594 conjugated Ab, 1:800, at a room temperature for 1 hour) against αSMA was progressed sequentially, and then the level of expression of αSMA was observed by using a fluorescence microscope.

FIG. 2 is observing the effect of treating various synthetic example compounds (5 μM) after inducing αSMA expression by treatment of TGF-β1 (5 μM) to ARPE19 cells. All of the Synthetic examples 3, 8, 9, 26 compounds showed an effect of inhibiting αSMA expression of 35%-70% or more, although there was a difference in the degree.

In addition, also in the HFF-1, LX-2, NHLF, ARPE19, KEL-FIB cells, as could be confirmed in FIG. 3*a* and FIG. 3*b*, it was observed that the increase of expression of αSMA induced by TGF-β1 (10 ng/ml) was significantly inhibited by treatment of the 5 μM Synthetic example 3 compound.

<Example 3> Analysis of ROS Production Change for Dopaminergic Nerve Cells

The high ROS level in nerve cells induces oxidized lipids, and this is known as an important element for nerve cell death. In order to confirm the effect of the synthetic example compound on ROS production from dopaminergic nerve cells, ROS production was induced by stimulation of MPP+ (1-methyl-4-phenylptridinium) for N27 (rat dopaminergic neural cell, Sigma) cells, and the inhibitory effect of ROS production of the synthetic example compound was observed under this condition.

N27 cells were cultured in a RPMI medium comprising 10% FBS, 1 μM angiotensin II, and the cultured cells were aliquoted in a 6 well plate at a concentration of $5\times10^3$~$6\times10^3$ cells/well. The ROS production stimuli, MPP+ (1-methyl-4-phenylptridinium) and Synthetic example compound 3 (1 μM) were treated into the cells. In 24 hours after treating the synthetic example compound, by measuring fluorescence of each well using DCF-DA, the ROS production level was confirmed.

As the result of the experiment, as could be confirmed in FIG. 4, it was confirmed that the ROS production induced by MPP+ was effectively inhibited by treatment of the synthetic example compound.

<Example 4> Analysis of CTGF and COL1A1 Gene Expression Change for Keloid Fibroblasts In order to confirm the effect on the process of producing extracellular matrix from keloid fibroblasts of the synthetic example compound, the expression change of an extracellular matrix formation promoting factor, CTGF and a representative extracellular matrix, collagen type I according to treatment of the Synthetic example 3 compound for KEL-FIB (keloid fibroblast) cells was analyzed at a gene level.

The KEL-FIB cell line was adapted in a DMEM comprising 2% FBS for 24 hours and then the Synthetic example 3 compound at a concentration of 후 5 μM or 10 μM was pretreated for 1 hour. For inducing expression of CTGF and collagen type I genes, 2 ng/ml TGF-β1 was treated and mRNA was extracted from the cells after 24 or 48 hours. The presence of mRNA and expression level of CTGF and collagen type 1 genes were confirmed by qRT-PCR (Quantitative real-time PCR).

As the result of the experiment, it was confirmed that the expression of the CTGF gene and collagen type I gene was increased by 26 times and 2.3 times, respectively, by treatment of 2 ng/ml TGF-β1, and then, the expression of the two genes was inhibited by 76% and 75% by treatment of 5 μM or 10 μM Synthetic example 3 compound.

<Example 5> Analysis of Expression Change of IL-1β Induced by LPS

In order to confirm the effect on inflammation reaction of the Synthetic example compounds of the present invention in human-derived fibroblasts, whether the expression of IL-1b increased by LPS treatment was inhibited was observed in fibroblasts derived from various tissues.

After inoculating a $2\times10^5$ number of cells in a 6 well plate and culturing for 24 hours and then further culturing in a culture solution without serum for 16 hours, the Synthetic example 3 compound was pretreated according to each condition for 30 minutes and inflammation reaction was induced by LPS for 6 hours. The expression of IL-1β was confirmed by using RT-PCR. The total RNA was separated from the cells by using RNeasy mini kit (Qiagen) and from the separated RNA 2 ug, cDNA was synthesized by using PrimeScript™ II $1^{st}$ strand cDNA synthesis kit (TaKaRa) and then PCR was performed by AccuPower® PCR PreMix (Bioneer) to amplify genes. The sequence for target primers is as follows. IL-1β (forward: 5'-CCACAGACCTTCCAGGAGAATG-3', reverse: 5'-GTGCAGTTCAGTGATCGTACAGG-3'); GAPDH (forward: 5'-GTGGCTGGCTCAGAAAAAGG-3', reverse: 5'-GGTGGTCCAGGGGTCTTACT-3'); β-actin (forward: 5'-CACCATTGGCAATGAGCGGTTC-3', reverse: 5'-AGGTCTTTGCGGATGTCCACGT-3'). The PCR product was confirmed by electrophoresis in 1.5% agarose gel.

As the result of the experiment, as could be confirmed in FIG. 5, it was observed that the IL-1β induced by LPS was effectively inhibited in a concentration-dependent manner by treatment of the Synthetic example 3 compound.

<Example 7> Confirmation of Inhibitory Effect of Pulmonary Fibrosis in Bleomycin-Induced Pulmonary Fibrosis Mouse Model As a bleomycin-induced pulmonary fibrosis mouse model, 5-week-old, C57BL/6J male mice weighing 20 g before and after were used. The experiment was progressed by dividing the experimental animals into a control group in which distilled water was orally administered (Control), a group in which pulmonary fibrosis was caused by bleomycin (BLM), an experimental group in which bleomycin was administered and in 3 weeks, as a positive control group, nintedanib of 100 mg/kg was orally administered daily (BLM+NIN), and an experimental group in which bleomycin was administered and in 3 weeks, the synthetic example compound of the present invention of 3 mg/kg was orally administered daily (BLM+Synthetic example) as 7 mice per group.

The nintedanib and synthetic example compound was orally administered once a day for 28 days. Next day of the last administration of the nintedanib or synthetic example compound, each animal was anesthetized and then blood was drawn by cardiac puncture and then sacrificed, and BALF (broncho-alveolar lavage fluid) and lung tissue were separated and used for a further test. Hematoxylin & Eosin (H&E) staining which is cell staining, and Masson's trichrome (MT) for confirming fibrosis were conducted, and the expression rate of αSMA and Collagen I in the pulmonary tissue was confirmed.

Comprehensively, based on the above histological and immunological results, by quantifying with improved Ashcroft scores (modified Ashcroft scale) widely used in the pulmonary fibrosis tissue analysis field, the severity of pulmonary fibrosis of each of the synthetic example compound administration groups (BLM+Synthetic example) compared to the negative control group (control), experimental group (BLM), positive control group was evaluated. Histopathological examination of the prepared tissue slides was confirmed using an optical microscope (Carl Zeiss, Oberkochen, Germany). For the experimental result, the mean and standard deviation were calculated using SPSS ver. 22.0 statistical program (SPSS Inc., Chicago, Ill., USA) and the significance of the difference between experimental groups was verified at a level of $p<0.05$ by student t-test.

As the result of the experiment, as could be confirmed in FIG. 6, as the result of histological analysis by H&E staining and MT staining, it was confirmed that the degree of infiltration of inflammatory cells into the alveolar and bronchiole was significantly lower in the experimental group in which pulmonary fibrosis was caused (BLM+vehicle), positive control group (BLM+NIN), and Synthetic example compound administration group (BLM+Synthetic example) than the experimental group and positive control group, and it was confirmed that epithelial cell hypertrophy was reduced, and lung structural deformation was reduced and abnormal tissue deposition sites were reduced.

In addition, it was confirmed that the size of the fibrosis area and collagen deposition due to fibrosis were significantly reduced in the synthetic example compound administration group (BLM+Synthetic example) compared to the experimental group and positive control group, and it was confirmed that the αSMA expression was significantly inhibited to the level of the normal group. Therefore, it was confirmed that the synthetic example compound effectively improved pulmonary fibrosis.

Comprehensively, based on the above histological and immunological results, as the result of evaluating the severity of pulmonary fibrosis of each of the synthetic example compound administration groups (BLM+Synthetic example) compared to the negative control group (control), experimental group (BLM), positive control group by quantifying with improved Ashcroft scores (modified Ashcroft scale) widely used in the pulmonary fibrosis tissue analysis field, the score in the negative control group (PBS) showing normal findings was 0.4±0.55, and the experimental group in which pulmonary fibrosis was caused by bleomycin (BLM) was 5.4±0.5. The improved Ashcroft score of the positive control group (BLM+NIN) was reduced to 5.0±0, and the improved Ashcroft score of the experimental group in which the synthetic example compound was administered (BLM+Synthetic example) was 3.44±0.88, and thus it was confirmed that the compound of the present invention effectively improved pulmonary fibrosis compared to nintedanib used as a conventional therapeutic agent of idiopathic pulmonary fibrosis.

<Example 8> Confirmation of Therapeutic Effect for Non-Alcoholic Steatohepatitis and Liver Fibrosis in STAM Mouse Model In order to confirm the therapeutic effect for non-alcoholic steatohepatitis and liver fibrosis of the synthetic example compound of the present invention, non-alcoholic steatohepatitis and liver fibrosis-induced STAM mice (6-week-old, female, SMC laborlabories Inc, Japan) were used. All the mice were maintained under a standard condition. The experiment was progressed by dividing the experimental animals into a normal control group in which distilled water was orally administered (negative control), STAM group in which non-alcoholic steatohepatitis and fibrosis were induced (vehicle control), an experimental group in which telmisartane of 10 mg/kg was orally administered daily as a STAM positive control group (STAM+TEL), and an experimental group in which the synthetic example compound of 3 or 10 mg/kg was orally administered daily (STAM+Synthetic example) as 7 mice per group. The telmisartane and synthetic example compound were orally administered once a day for 28 days.

After completing the test, the animals were anesthetized and liver tissue was extracted for each individual, and blood was taken for examination. The weight of the liver tissue was measured and it was photographed. The tissue was fixed in 10% buffered neutral formalin solution. After cutting the fixed tissues to a certain thickness, it was embedded in paraffin through a general tissue treatment process to prepare tissue sections of 4~5 μm, and then Hematoxylin & Eosin (H&E stain) staining which is a general staining method, Sirius red staining for confirming fibrosis and Oil red O working solution staining for confirming the degree of formation of lipids were performed to observe histopathological findings.

Comprehensively, based on the above histological and immunological results, as the result of evaluating the severity of hepatitis and liver fibrosis of each of the synthetic example compound administration groups (STAM+Synthetic example) compared to the negative control group (control), experimental group (STAM), positive control group (STAM+TEL) by quantifying with improved NAS (Nonalcoholic Fatty Liver Disease Activity Dcore) scores widely used in the hepatitis and fibrosis tissue analysis field, the score was 0.0±0.0 in the normal control group showing normal findings (normal control) and it was 4.8±0.7 in the STAM experimental group (STAM+vehicle). The improved NAS score of the positive control group (STAM+TEL) was reduced to 2.8±0.7, and the improved NAS score in the experimental group in which the synthetic example compound was administered (STAM+Synthetic example) was confirmed as 2.6±0.7.

In addition, according to the result of Sirius red staining for confirming the degree of liver fibrosis, the liver fibrosis area was 0.29±0.06 in the normal control group showing normal findings (normal control), and it was 0.93±0.36 in the STAM experimental group (STAM+vehicle). It was confirmed that the improved fibrosis area of the positive control group (STAM+TEL) was reduced to 0.44±0.15 and the improved fibrosis area of the experimental group in which the synthetic example compound was administered (STAM+Synthetic example) was reduced to 0.49±0.16.

It was confirmed that the synthetic example compound of the present invention effectively improved non-alcoholic hepatitis and liver fibrosis.

<Example 9> Confirmation of Brain Injury Treatment Effect

In order to test the effect of preventing or treating brain disease or illness of the synthetic example compounds, a Parkinson's disease mouse (alpha-Synuclein A53T mutant transgenic mouse) model was established.

All the mice were maintained under a standard condition. The experiment was performed by dividing experimental animals into a normal control group in which distilled water was orally administered (negative control), a Parkinson's disease induced group (vehicle control) and an experimental group in which the Synthetic example compound of 25 mg/kg was orally administered daily (Synthetic example) as 8 mice per group. The normal control group was administered with physiological saline and the synthetic example compound was orally administered once a day for 2 weeks, and then a behavioral change experiment and a histopathological experiment were performed.

The behavioral change was analyzed by Rota rod, a pole test and hindlimb clasping, and the average value of three experiments was measured for each animal.

After completing the test, the animals were anesthetized to extract brain tissues for each individual, and the tissues were fixed in 4% buffered neutral formalin. After cutting the fixed tissues to a certain thickness, it was embedded in paraffin through a general tissue treatment process to prepare tissue sections of 4~5 μm. Then, in order to confirm whether the Parkinson's disease pathology index was improved according to the level of protein aggregation in the striatum, it was first labeled with phosphorylated-Serin-129 alpha-synuclein and then Thioflavin-T staining was performed to observe histopathological findings.

As the result of the experiment, as the result of behavioral change analysis of the Rota rod, pole test and hindlimb clasping in the synthetic example compound administration group, it was confirmed that Parkinson-like behavioral symptoms were improved by 50% or more, and aggregation and accumulation of a-synuclein, an important pathological indicator, were improved by 50% or more.

In conclusion, it was confirmed that the synthetic example compounds of the present invention effectively improved Parkinson's disease.

The invention claimed is:

1. A compound represented by Chemical formula I-1 below, or a stereoisomer or a pharmaceutically acceptable salt thereof, <Chemical formula I-1>

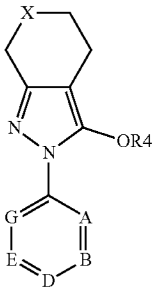

wherein,

X is NR3, and

R3 is selected from Ra-L-, Ra-L-CO—, Ra-L-NHCO—, Ra-L-OCO—, Ra-L-$SO_2$—; and

Ra is selected from hydrogen, heavy hydrogen, cyan, halogen, nitro, haloalkyl, substituted or non-substituted C1-C10 linear or branched alkyl, substituted or non-substituted C3-C8 cycloalkyl, substituted or non-substituted C5-C20 aryl, or substituted or non-substituted C5-C20 heteroaryl, and the heteroaryl comprises 1, 2 or 3 heteroatoms among O, N and S; and L is selected from direct boding and C1-C3 alkylene; and R4 is selected from hydrogen or substituted or non-substituted C1-C10 alkyl; and A is CR5 or N, B, and CR6 or N, D is CR7 or N, and E is CR8 or N, and G is CR9 or N; and N in A, B, C, D, E, G is 0 or 1, and R5 to R9 are same or different, and are each independently selected from hydrogen, heavy hydrogen, cyan, halogen, haloalkyl, carbonyl, nitro, carboxyl, C1-C5 alkoxy, substituted or non-substituted C1-C10 linear or branched alkyl, substituted or non-substituted C3-C8 cycloalkyl, substituted or non-substituted amine, substituted or non-substituted C5-C20 aryl, or substituted or non-substituted C5-C20 heteroaryl, and two or more groups adjacent to each other may combine with each other to form a substituted or non-substituted aromatic hydrocarbon ring, wherein the aromatic hydrocarbon ring may form a C5-C10 heteroaryl ring comprising 1, 2 or 3 heteroatoms selected from N, O and S, or C5-C10 aryl ring; and the substituted C1-C10 linear or branched alkyl may be optionally partially unsaturated, and is independently substituted to one or more substituents selected from heavy hydrogen, halogen, cyan, nitro, carboxyl, substituted or non-substituted amine, substituted or non-substituted C5-C20 aryl or C5-C20 heteroaryl, substituted or non-substituted C3-C8 cycloalkyl; and the substituted C3-C8 cycloalkyl may be substituted independently as one or more substituents selected from heavy hydrogen, halogen, cyan, nitro, carboxyl, substituted or non-substituted amine, substituted or non-substituted C5-C20 aryl or C5-C20 heteroaryl, C1-C5 alkoxy and C1-C5 haloalkyl or same or different 2 or more substituents are linked; and the substituted C5-C20 aryl or substituted C5-C20 heteroaryl is substituted independently as one or more substituents selected from heavy hydrogen, halogen, cyan, nitro, carboxyl, substituted or non-substituted amine, C1-C5 alkoxy, C1-C5 haloalkyl, C1-C10 alkyl, C3-C8 cycloalkyl C1-C10 alkyl, and C5-C20 aryl C1-C10 alkyl or same or different 2 or more substituents are linked;

the substituted amine is substituted to one or two of C1-C5 alkyl groups; and the substituted C5-C10 arylene is substituted to one or more substituents selected from C1-C3 alkyl, halogen, cyan, amine, nitro and heavy chain or same or different 2 or more substituents are linked.

2. The compound, stereoisomer or pharmaceutically acceptable salt according to claim 1, wherein R3 is Ra-L, and L is selected from direct bonding and C1-C3 alkylene, and N in A, B, D, E, G is 0 or 1, and the R5 to R9 are same or different, and are each independently selected from hydrogen, heavy hydrogen, cyan, halogen, haloalkyl, carbonyl, nitro, carboxyl, C1-C5 alkoxy, C1-C5 alkyl, C1-C5 haloalkyl in which one or more halogens are substituted, substituted or non-substituted C3-C8 cycloalkyl, substituted or non-substituted amine, substituted or non-substituted C5-C10 aryl, or substituted or non-substituted C5-C10 heteroaryl, and two or more groups adjacent to each other combine with each other to form a substituted or non-substituted aromatic hydrocarbon ring, wherein the aromatic hydrocarbon ring may form a C5-C10 heteroaryl ring comprising 0, 1, 2 or 3 heteroatoms selected from N, O and S, or C5-C10 aryl ring; and R4 is selected from hydrogen or substituted or non-substituted C1-C5 alkyl.

3. The compound, stereoisomer or pharmaceutically acceptable salt according to claim 1, wherein R3 is Ra-L-CO—; and L is selected from direct bonding and C1-C3 alkylene, and N in A, B, D, E, G is 0 or 1; and the R5 to R9 are same or different, and are each independently selected from hydrogen, heavy hydrogen, cyan, halogen, haloalkyl, carbonyl, nitro, carboxyl, C1-C5 alkoxy, C1-C5 alkyl, C1-C5 haloalkyl in which one or more halogens are substituted, substituted or non-substituted C3-C8 cycloalkyl, substituted or non-substituted amine, substituted or non-substituted C5-C10 aryl, or substituted or non-substituted C5-C10 heteroaryl, and two or more groups adjacent to each other may combine with each other to form a substituted or non-substituted aromatic hydrocarbon ring, wherein the aromatic hydrocarbon ring may form a C5-C10 heteroaryl ring comprising 1, 2 or 3 heteroatoms selected from N, O and S or C5-C10 aryl ring; and R4 is selected from hydrogen or substituted or non-substituted C1-C5 alkyl.

4. The compound stereoisomer or pharmaceutically acceptable salt according to claim 1, wherein the R3 is Ra-L-NHCO—, and L is selected from direct bonding and C1-C3 alkylene, and N in A, B, D, E, G is 0 or 1; and the R5 to R9 are same or different, and are each independently selected from hydrogen, heavy hydrogen, cyan, halogen, haloalkyl, carbonyl, nitro, carboxyl, C1-C5 alkoxy, C1-C5 alkyl, C1-C5 haloalkyl in which one or more halogens are substituted, substituted or non-substituted C3-C8 cycloalkyl, substituted or non-substituted amine, substituted or non-substituted C5-C10 aryl, or substituted or non-substituted C5-C10 heteroaryl, and two or more groups adjacent to each other may combine with each other to form a substituted or non-substituted aromatic hydrocarbon ring, wherein the aromatic hydrocarbon ring may form a C5-C10 heteroaryl ring comprising 1, 2 or 3 heteroatoms selected from N, O and S or C5-C10 aryl ring; and R4 is selected from hydrogen or substituted or non-substituted C1-C5 alkyl.

5. The compound, stereoisomer or pharmaceutically acceptable salt according to claim 1, wherein the R3 is Ra-L-OCO—; and L is selected from direct bonding and C1-C3 alkylene, and N in A, B, D, E, G is 0 or 1; and the R5 to R9 are same or different, and are each independently selected from hydrogen, heavy hydrogen, cyan, halogen, haloalkyl, carbonyl, nitro, carboxyl, C1-C5 alkoxy, C1-C5 alkyl, C1-C5 haloalkyl in which one or more halogens are substituted, substituted or non-substituted C3-C8 cycloalkyl, substituted or non-substituted amine, substituted or non-substituted C5-C10 aryl, or substituted or non-substituted C5-C10 heteroaryl, and two or more groups adjacent to each other may combine with each other to form a substituted or non-substituted aromatic hydrocarbon ring, wherein the aromatic hydrocarbon ring may form a C5-C10 heteroaryl ring comprising 1, 2 or 3 heteroatoms selected from N, O and S or C5-C10 aryl ring; and R4 is selected from hydrogen or substituted or non-substituted C1-C5 alkyl.

6. The compound, stereoisomer or pharmaceutically acceptable salt according to claim 1, wherein the R3 is Ra-L-$SO_2$—; and L is selected from direct bonding and C1-C3 alkylene, and N in A, B, D, E, G is 0 or 1; and the R5 to R9 are same or different, and are each independently selected from hydrogen, heavy hydrogen, cyan, halogen, haloalkyl, carbonyl, nitro, carboxyl, C1-C5 alkoxy, C1-C5 alkyl, C1-C5 haloalkyl in which one or more halogens are substituted, substituted or non-substituted C3-C8 cycloalkyl, substituted or non-substituted amine, substituted or non-substituted C5-C10 aryl, or substituted or non-substituted C5-C10 heteroaryl, and two or more groups adjacent to each other may combine with each other to form a substituted or non-substituted aromatic hydrocarbon ring, wherein the aromatic hydrocarbon ring may form a C5-C10 heteroaryl ring comprising 1, 2 or 3 heteroatoms selected from N, O and S or C5-C10aryl ring; and R4 is selected from hydrogen or substituted or non-substituted C1-C5 alkyl.

7. The compound represented by Chemical formula I or salt thereof according to claim 1, wherein the compound represented by the Chemical formula I-1 is selected from the following compounds, 6-benzyl-2-(pyridin-2-yl)-4,5,6,7-tetrahydro-2H-pyrazolo[3,4-c]pyridin-3-ol;

6-benzyl-2-(pyridin-2-yl)-4,5,6,7-tetrahydro-2H-pyrazolo[3,4-c]pyridin-3-ol;

6-benzyl-2-(5-(trifluoromethyl)pyridin-2-yl)-4,5,6,7-tetrahydro-2H-pyrazolo[3,4-c]pyridin-3-ol;

6-(4-fluorobenzyl)-2-(pyridin-2-yl)-4,5,6,7-tetrahydro-2H-pyrazolo[3,4-c]pyridin-3-ol;

6-(4-methylbenzyl)-2-(pyridin-2-yl)-4,5,6,7-tetrahydro-2H-pyrazolo[3,4-c]pyridin-3-ol;

4-((3-hydroxy-2-(pyridin-2-yl)-2,4,5,7-tetrahydro-6H-pyrazolo[3,4-c]pyridin-6-yl)methyl)benzonitrile;

6-(3,5-difluorobenzyl)-2-(pyridin-2-yl)-4,5,6,7-tetrahydro-2H-pyrazolo[3,4-c]pyridin-3-ol;

2-(pyridin-2-yl)-6-(3-(trifluoromethyl)benzyl)-4,5,6,7-tetrahydro-2H-pyrazolo[3,4-c]pyridin-3-ol;

6-(naphthalene-2-ylmethyl)-2-(pyridin-2-yl)-4,5,6,7-tetrahydro-2H-pyrazolo[3,4-c]pyridin-3-ol;

1-(4,5-dihydro-3-hydroxy-2-(pyridin-2-yl)-2H-pyrazolo[3,4-c]pyridin-6(7H)-yl)butan-1-one;

1-(3-hydroxy-2-(pyridin-2-yl)-2,4,5,7-tetrahydro-6H-pyrazolo[3,4-c]pyridin-6-yl)ethan-1-one;

6-(4-methoxybenzyl)-2-(pyridin-2-yl)-4,5,6,7-tetrahydro-2H-pyrazolo[3,4-c]pyridin-3-ol;

6-ethyl-2-(pyridin-2-yl)-4,5,6,7-tetrahydro-2H-pyrazolo[3,4-c]pyridin-3-ol;

6-(prop-2-yn-1-yl)-2-(pyridin-2-yl)-4,5,6,7-tetrahydro-2H-pyrazolo[3,4-c]pyridin-3-ol;

6-propyl-2-(pyridin-2-yl)-4,5,6,7-tetrahydro-2H-pyrazolo[3,4-c]pyridin-3-ol;

6-allyl-2-(pyridin-2-yl)-4,5,6,7-tetrahydro-2H-pyrazolo[3,4-c]pyridin-3-ol;

(3-hydroxy-2-(pyridin-2-yl)-2,4,5,7-tetrahydro-6H-pyrazolo[3,4-c]pyridin-6-yl)(phenyl)methanone;

benzyl 3-hydroxy-2-(pyridin-2-yl)-2,4,5,7-tetrahydro-6H-pyrazolo[3,4-c]pyridin-6-carboxylate;

(4-chlorophenyl)(3-hydroxy-2-(pyridin-2-yl)-2,4,5,7-tetrahydro-6H-pyrazolo[3,4-c]pyridin-5-yl)methanone;

ethyl 3-hydroxy-2-(pyridin-2-yl)-2,4,5,7-tetrahydro-6H-pyrazolo[3,4-c]pyridin carboxylate;

N-cyclohexyl-3-hydroxy-2-(pyridin-2-yl)-2,4,5,7-tetrahydro-6H-pyrazolo[3,4-c]pyridin-6-carboxamide;

furan-2-yl(3-hydroxy-2-(pyridin-2-yl)-2,4,5,7-tetrahydro-6H-pyrazolo[3,4-c]pyridin-6-yl)methanone;

6-(methylsulfonyl)-2-(pyridin-2-yl)-4,5,6,7-tetrahydro-2H-pyrazolo[3,4-c]pyridin-3-ol;

6-(phenylsulfonyl)-2-(pyridin-2-yl)-4,5,6,7-tetrahydro-2H-pyrazolo[3,4-c]pyridin-3-ol;

N-(4-fluorophenyl)-3-hydroxy-2-(pyridin-2-yl)-2,4,5,7-tetrahydro-6H-pyrazolo[3,4-c]pyridin-6-carboxamide;

N-(4-fluorobenzyl)-3-hydroxy-2-(pyridin-2-yl)-2,4,5,7-tetrahydro-6H-pyrazolo[3,4-c]pyridin-6-carboxamide;

N-(furan-2-ylmethyl)-3-hydroxy-2-(pyridin-2-yl)-2,4,5,7-tetrahydro-6H-pyrazolo[3,4-c]pyridin-6-carboxamide;

N-(4-chlorophenethyl)-3-hydroxy-2-(pyridin-2-yl)-2,4,5,7-tetrahydro-6H-pyrazolo[3,4-c]pyridin-6-carboxamide;

6-(naphthalene-2-ylsulfonyl)-2-(pyridin-2-yl)-4,5,6,7-tetrahydro-2H-pyrazolo[3,4-c]pyridin-3-ol;

4-nitrobenzyl 3-hydroxy-2-(pyridin-2-yl)-2,4,5,7-tetrahydro-6H-pyrazolo[3,4-c]pyridin-6-carboxylate;

(5-(4-cyclopropyl-1H-imidazol-1-yl)-2-fluoro-4-methylphenyl)(3-hydroxy (pyridin-2-yl)-2,4,5,7-tetrahydro-6H-pyrazolo[3,4-c]pyridin-6-yl)methanone;

6-benzyl-2-(5-chloropyridin-2-yl)-4,5,6,7-tetrahydro-2H-pyrazolo[3,4-c]pyridin-3-ol;

4-(6-benzyl-3-hydroxy-4,5,6,7-tetrahydro-2H-pyrazolo[3,4-c]pyridin-2-yl)benzoic acid;

6-benzyl-2-(4-bromophenyl)-4,5,6,7-tetrahydro-2H-pyrazolo[3,4-c]pyridin-3-ol;

6-benzyl-2-phenyl-4,5,6,7-tetrahydro-2H-pyrazolo[3,4-c]pyridin-3-ol;

6-benzyl-2-(2-chlorophenyl)-4,5,6,7-tetrahydro-2H-pyrazolo[3,4-c]pyridin-3-ol;

6-benzyl-2-(2-methoxyphenyl)-4,5,6,7-tetrahydro-2H-pyrazolo[3,4-c]pyridin-3-ol;

6-benzyl-2-(thieno[3,2-c]pyridin-4-yl)-4,5,6,7-tetrahydro-2H-pyrazolo[3,4-c]pyridin-3-ol;

2-(pyridin-2-yl)-6-(pyridin-2-ylmethyl)-4,5,6,7-tetrahydro-2H-pyrazolo[3,4-c]pyridin-3-ol;

2-(pyridin-2-yl)-6-(pyridin-4-ylmethyl)-4,5,6,7-tetrahydro-2H-pyrazolo[3,4-c]pyridin-3-ol;

6-(4-(dimethylamino)benzyl)-2-(pyridin-2-yl)-4,5,6,7-tetrahydro-2H-pyrazolo[3,4-c]pyridin-3-ol;

6-(3-(dimethylamino)benzyl)-2-(pyridin-2-yl)-4,5,6,7-tetrahydro-2H-pyrazolo[3,4-c]pyridin-3-ol;

2-(6-aminopyridin-2-yl)-6-benzyl-4,5,6,7-tetrahydro-2H-pyrazolo[3,4-c]pyridin-3-ol;

2-(pyridin-2-yl)-6-(quinolin-6-ylmethyl)-4,5,6,7-tetrahydro-2H-pyrazolo[3,4-c]pyridin-3-ol;

6-(isoquinolin-3-ylmethyl)-2-(pyridin-2-yl)-4,5,6,7-tetrahydro-2H-pyrazolo[3,4-c]pyridin-3-ol.

8. The compound or salt thereof according to claim 1, wherein the salt is in a form of a salt induced by one or more kinds of acids selected from the group consisting of hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, benzoic acid, hydroxybenzoic acid, phenylacetic acid, cinnamic acid, salicylic acid, methanesulfonic acid, ethanesulfonic acid, benzenesulfonic acid, and toluenesulfonic acid.

9. A method of treating oxidative stress-related disease in a subject comprising administering to the subiect the compound of claim 1 or a pharmaceutically acceptable salt thereof as active ingredient and a pharmaceutically acceptable carrier, wherein the oxidative stress-related disease is selected from cancer hepatic fibrosis, lung fibrosis and Parkinson's disease.

10. The method according to claim 9 wherein the pharmaceutically acceptable carrier is one or more kinds selected from the group consisting of excipients, diluents, disintegrants, binders, lubricants, surfactants, emulsifiers, suspending agents and diluents.

* * * * *